US012623040B2

(12) United States Patent
 Spear et al.

(10) Patent No.: US 12,623,040 B2
(45) Date of Patent: May 12, 2026

(54) NASAL SEAL FOR A RESPIRATORY PATIENT INTERFACE

(71) Applicant: Fisher & Paykel Healthcare Limited, Auckland (NZ)

(72) Inventors: Tony William Spear, Auckland (NZ); Matthew Roger Stephenson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 848 days.

(21) Appl. No.: 17/250,823

(22) PCT Filed: Sep. 12, 2019

(86) PCT No.: PCT/IB2019/057677
§ 371 (c)(1),
(2) Date: Mar. 5, 2021

(87) PCT Pub. No.: WO2020/053794
PCT Pub. Date: Mar. 19, 2020

(65) Prior Publication Data
US 2021/0213227 A1    Jul. 15, 2021

Related U.S. Application Data

(60) Provisional application No. 62/730,481, filed on Sep. 12, 2018.

(51) Int. Cl.
*A61M 16/06*         (2006.01)
(52) U.S. Cl.
CPC . *A61M 16/0616* (2014.02); *A61M 2210/0618* (2013.01)

(58) Field of Classification Search
CPC ...... A61M 16/0616; A61M 2210/0618; A61M 16/0816; A61M 2205/42;
(Continued)

(56) References Cited

U.S. PATENT DOCUMENTS 2,939,458 A    6/1960  Lundquist
4,782,832 A    11/1988  Trimble et al.
(Continued)

FOREIGN PATENT DOCUMENTS

CN      106029144      10/2016
JP      H1082445       3/1998
(Continued)

OTHER PUBLICATIONS

Patent Cooperation Treaty, International Search Report and Written Opinion, Application No. PCT/IB2019/057677, dated Dec. 24, 2019, in 33 pages.

*Primary Examiner* — Justine R Yu
*Assistant Examiner* — Matthew R Moon
(74) *Attorney, Agent, or Firm* — VIA LLP

(57)                 ABSTRACT

A nasal seal for a respiratory therapy mask for contacting the face of a user. The nasal seal has a main body defining a cavity and a fluid inlet, and has two nasal prongs projecting from the main body for the delivery of fluid to the user's nares. A transition fillet is provided around a base of each prong, between the nasal prong and the main body, with each transition fillet having a constant chord length.

21 Claims, 41 Drawing Sheets

(58) Field of Classification Search
    CPC ...... A61M 2205/582; A61M 2205/583; A61M
                2205/7527; A61M 2205/7536; A61M
                16/0666; A61M 16/0605; A61M 16/0683;
                        A61M 16/0875; A61M 2206/10
    See application file for complete search history.

(56)                References Cited

U.S. PATENT DOCUMENTS

| | | | |
|---|---|---|---|
| 4,907,584 A | 3/1990 | McGinnis | |
| 5,243,971 A | 9/1993 | Sullivan et al. | |
| 5,477,852 A | 12/1995 | Landis et al. | |
| 5,540,223 A | 7/1996 | Starr et al. | |
| 5,687,715 A | 11/1997 | Landis et al. | |
| 5,724,965 A * | 3/1998 | Handke | A61M 16/0605 |
| | | | 128/207.18 |
| 6,044,844 A | 4/2000 | Kwok et al. | |
| 6,119,694 A | 9/2000 | Correa et al. | |
| 6,412,488 B1 | 7/2002 | Barnett et al. | |
| 6,431,172 B1 | 8/2002 | Bordewick | |
| 6,467,483 B1 | 10/2002 | Kopacko et al. | |
| 6,478,026 B1 | 11/2002 | Wood | |
| 6,644,315 B2 | 11/2003 | Ziaee | |
| 7,357,136 B2 | 4/2008 | Ho et al. | |
| 8,136,525 B2 | 3/2012 | Lubke et al. | |
| 8,997,747 B2 | 4/2015 | Hobson | |
| 9,072,855 B2 | 7/2015 | McAuley et al. | |
| 9,480,809 B2 | 11/2016 | Guney et al. | |
| 9,526,857 B2 | 12/2016 | Rummery et al. | |
| 9,943,660 B2 * | 4/2018 | Selvarajan | A61M 16/0683 |
| 2002/0092527 A1 | 7/2002 | Wood | |
| 2003/0221691 A1 | 12/2003 | Biener et al. | |
| 2004/0226566 A1 * | 11/2004 | Gunaratnam | A61M 16/0825 |
| | | | 128/207.18 |
| 2005/0028822 A1 * | 2/2005 | Sleeper | A61M 16/0833 |
| | | | 128/207.18 |

| | | | |
|---|---|---|---|
| 2005/0066976 A1 | 3/2005 | Wondka | |
| 2006/0266361 A1 * | 11/2006 | Hernandez | A61M 16/06 |
| | | | 128/207.18 |
| 2006/0283461 A1 | 12/2006 | Lubke et al. | |
| 2007/0137653 A1 | 6/2007 | Wood | |
| 2009/0145429 A1 | 6/2009 | Ging et al. | |
| 2009/0320851 A1 * | 12/2009 | Selvarajan | A61M 16/0683 |
| | | | 128/207.13 |
| 2011/0146685 A1 | 6/2011 | Allan et al. | |
| 2012/0204870 A1 * | 8/2012 | McAuley | A61M 16/0816 |
| | | | 128/207.18 |
| 2013/0186404 A1 | 7/2013 | Chien | |
| 2015/0136139 A1 * | 5/2015 | Franzen | A61M 16/0605 |
| | | | 128/205.25 |
| 2016/0151596 A1 * | 6/2016 | Slight | A61M 16/0622 |
| | | | 128/207.18 |
| 2016/0256653 A1 * | 9/2016 | McAuley | A61M 16/0875 |

FOREIGN PATENT DOCUMENTS

| | | |
|---|---|---|
| WO | WO 2004/073778 | 9/2004 |
| WO | WO 2008/007985 A1 | 1/2008 |
| WO | WO 2009/052560 | 4/2009 |
| WO | WO 2009/139647 A1 | 11/2009 |
| WO | WO 2009/151344 | 12/2009 |
| WO | WO 2010/041966 A1 | 4/2010 |
| WO | WO 2010/131189 A1 | 5/2010 |
| WO | WO 2010/135785 | 12/2010 |
| WO | WO 2011/059346 A1 | 5/2011 |
| WO | WO 2013/168134 | 11/2013 |
| WO | 2014021722 | 2/2014 |
| WO | 2014091362 | 6/2014 |
| WO | WO 2015/009172 A1 | 1/2015 |
| WO | WO 2017/160166 | 9/2017 |
| WO | 2018150889 | 8/2018 |

* cited by examiner

NASAL SEAL FOR A RESPIRATORY PATIENT INTERFACE

BACKGROUND

Field of the Invention

The present disclosure generally relates to a respiratory patient interface, in particular to a nasal pillow type mask.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnoea (OSA), a condition in which a patient's airway intermittently collapses during sleep, preventing the patient from breathing for a period of time. The cessation of breathing, or apnoea, results in the patient awakening. Repetitive and frequent apnoeas may result in the patient rarely achieving a full and restorative night's sleep.

CPAP therapy involves the delivery of a supply of continuous positive air pressure to the airway of the patient via a respiratory mask. The continuous positive pressure acts to keep the airway in an open position so the patient's breathing and sleep are not interrupted.

CPAP therapy requires the user to wear a respiratory interface which seals against a user's face, around their nose and/or mouth via a seal/cushion to deliver respiratory gas or gases such as air to a user under positive pressure. Respiratory masks are available in a range of styles including full-face, nasal, direct nasal and oral masks. The seal/cushion is held in place on the user's face by headgear which provides support to the respiratory interface such that it is held in a stable position relative to the user's face during use. Such respiratory masks may also be used to deliver NIV and other therapies.

Patients may be deterred from using CPAP therapy if they find the respiratory interface uncomfortable or invasive or if they find the appearance of the interface unattractive. There is a desire for more discrete, compact user interfaces. During the treatment of OSA, a patient wears the mask while they sleep, so the mask must fit with enough stability to not be dislodged as the patient turns in their sleep.

CPAP therapy is commonly used in a home environment, on occasion it is necessary to change the seal of the respiratory interface, either for replacement or cleaning. For users with impaired motor function, changing a seal, or refitting the seal if it becomes separated from the supporting frame, can be difficult. Often this requires precision handling, and may involve non-intuitive assembly steps and/or the use of separate connector components.

Handling the seal in this manner, or indeed day to day handling, can cause portions of the seal to become inverted or rolled over on themselves, for example nasal prongs in a nasal seal may roll or 'pop' inwards. This same inversion of components may occur during use of the mask, for example by incorrectly fitting the mask, or through movement of the mask. Righting these inverted components can be challenging for some users, particularly for those users with impaired motor skills or vision.

In this specification where reference has been made to patent specifications, other external documents, or other sources of information, this is generally to provide a context for discussing features of the invention. Unless specifically stated otherwise, reference to such external documents or sources of information is not to be construed as an admission that such documents or such sources of information, in any jurisdiction, are prior art or form part of the common general knowledge in the art.

SUMMARY OF THE INVENTION

In a first aspect, the present disclosure relates to a nasal seal for a respiratory therapy mask for contacting the face of a user. The nasal seal has a main body defining at least a portion of a cavity and a fluid inlet, two nasal prongs projecting from the main body for the delivery of fluid to the user's nares, and a transition fillet around a base of each prong, between the nasal prong and the main body. The cavity forms a breathing chamber. Each transition fillet has a constant chord length.

In an embodiment, the nasal seal comprises a resilient material. For example, the nasal seal may include an elastomer such as silicone. In one embodiment, the nasal seal comprises a single-durometer silicone.

In an embodiment, a terminal region of each nasal prong has a wall thickness that tapers towards a tip of the nasal prong. The wall thickness at the nasal prongs' tips may be less than 20% of the wall thickness of the nasal prong wall in a major part of the nasal prong.

In an embodiment, the nasal prong wall thickness gradually decreases over a length of about 2 mm. That is, the terminal region of the prong is 2 mm in length. In alternative embodiments the terminal region may be longer or slightly shorter, and is preferably in the range of about 1.2 mm to about 4 mm, more preferably about 1.6 mm to about 3 mm, and most preferably in the range of about 1.8 mm to about 2.5 mm.

The taper in the terminal regions may be a non-linear taper. That is an interior or exterior surface of the taper has a curved surface, such that the gradient of the taper changes along the length of the taper. In one embodiment, the taper has a varying chord length and a varying radius of curvature.

The taper may be an external taper. That is, the contour providing the reduction in wall thickness is on the external surface of the prong. In an embodiment, the external surface of the prong in at least in the terminal region is a curved surface and the internal surface of the prong in at least in the terminal regional is substantially linear when viewed in cross-section through the prong wall.

Each nasal prong defines a prong cavity wherein the cross-sectional area of each prong cavity decreases from a maximum area at the base of the prong to a minimum area at the tip of the prong. That is, the widest part of the prong cavity is at the base of the cavity. The cross-sectional area of each prong cavity may decrease from a base to the tip in a non-uniform and/or eccentric manner. For example to conform and align the nasal prongs with the anatomy of a user's nares. In one example, the prongs are angled upwards and towards each other.

In an embodiment, each nasal prong defines a non-cylindrical cavity. For example, the prong cavity may decrease in cross-sectional area from a base to the tip in a non-uniform and/or eccentric manner, as described above. Alternatively or additionally, the cross section of the nasal prong may be non-circular. For example, the nasal prong cavity may be oblong, oval, or elliptical in cross section, or may be of another irregular curved shape. The cross sectional shape of each nasal prong cavity may vary from a base of the prong to the tip of the prong. For example, the prong cavity may transition from oblong to circular.

In one embodiment, each nasal prong cavity has a cross-sectional shape with a major dimension along a major axis, and a minor dimension along a minor axis, wherein both the major and minor dimensions decrease from the base of the respective prong to the tip. For example, the shape may be one or more of oval, oblong, or elliptical.

In one embodiment each nasal prong comprises a nare sealing region between the terminal region and the base of the respective prong. The nare sealing region has a transition region adjacent the prong terminal region. The transition region is concave. The transition region may have a constant chord length around a perimeter of the prong. In an embodiment, the outer surface of the nare sealing region is convex.

In an embodiment, the nasal seal comprises a user contacting rear surface on the seal main body, at least part of which is contoured to form a secondary seal with a user's face in use. For example, the seal main body may form a secondary seal below a user's nose. In an embodiment, the user contacting rear surface of the seal main body has a surface area between about 170 mm$^2$ and about 680 mm$^2$ preferably between about 450 mm$^2$ and about 650 mm$^2$, and more preferably between about 520 mm$^2$ and about 570 mm$^2$. In an embodiment, the user contacting rear surface of the seal main body has a surface area that is between about 28% and 110%, of the external surface area of each prong preferably between about 75% and about 105%, more preferably about 90%. In an embodiment the external surface area of each prong is about 600 mm$^2$, however, in alternative embodiments, the external surface area of each prong may be in the range of 500 mm$^2$ to about 700 mm$^2$ In an embodiment, each nasal prong comprises a nare sealing region between the terminal region and the base of the respective prong, at least a major part of the nare sealing region having a wall thickness that is at least twice the wall thickness of a user contacting rear part of the seal main body. In an embodiment, a user contacting rear surface of the seal main body has a wall thickness in the range of about 0.4 mm to about 0.6 mm, preferably about 0.45 mm. The nare sealing region of the prongs preferably have a substantially uniform thickness, of 0.76 to 0.85, preferably 0.78 to 0.82, preferably about 0.8 mm.

In an embodiment, the nasal seal main body comprises side walls extending between an inlet side of the seal and the user-contacting rear surface. These side walls may be about four to five times thicker than wall thickness of the user contacting rear part of the seal main body. In one embodiment, the side walls have a thickness of about 2 mm.

In an embodiment, the rate of change in wall thickness of the nasal seal across the width of the transition fillet, between the main body and the base of each nasal prong, is substantially constant around the perimeter of the base. An interior surface of the nasal seal comprises a corresponding chordal round at the base of each nasal prong. The chord on each chordal round is substantially the same as the chord on the transition fillet. In an embodiment, the chord length is in the range of about 3 mm to about 5 mm, for example, about 4 mm. In some embodiments, the radius of curvature of the fillet, and optionally the respective chordal round, varies along the fillet/round, around the perimeter of the prong. The radius may vary as by as much as four or five-fold, or more. In one embodiment, the curvature of the fillet varies from about 2 mm to about 9 mm. In one embodiment, the radius of curvature of the transition fillet is maximum at or near a bottom part of the fillet and respective prong.

In an embodiment, the fluid inlet is a substantially D-shaped opening, being widest at a bottom of the opening and narrowest at the top of the opening. The opening may be shaped such that at least a major part of the opening of the nasal prong cavities at the prong tips is directly aligned with the inlet. The bottom of the opening has a width that may be from about 1.5 to about 2 times the width of the top of the opening. In one embodiment, the bottom of the opening has a width of about 1.8 times the width of the top of the opening.

In an embodiment, the nasal seal comprises an inwardly extending lip at the fluid inlet for engaging a support frame. The lip may be D-shaped to define the D-shaped inlet. The lip may comprise a region of increased wall thickness compared to the side walls of the nasal seal. In one embodiment the lip has a depth of about 3 mm.

In an embodiment, the lip (and thereby the defined inlet) is arcuate in side profile, being concave relative to a front of the seal. In an embodiment, the lip side profile has a radius of about 25 mm and a centre of curvature that is forward of the nasal seal.

In an embodiment, the tips of the nasal prongs project rearward beyond a rear surface of the nasal seal main body. In an embodiment, the tips of the nasal prongs project rearward beyond the side of the nasal seal defined by a side portion of the main body. In at least some embodiments, the nasal seal main body doesn't contact the cheeks and/or nasal bridge of a user, or extend over the user's nose.

In an embodiment, each nasal prong comprises a web extending across the prong cavity. Each web may have a lower edge proximal to the base of the respective prong, and an upper edge spaced from the tip of said prong. In an embodiment, the cavity in each nasal prong has a cross-section with a major axis and a minor axis, and each web extends generally along the minor axis, or substantially parallel to the minor axis.

In a second aspect, the present disclosure relates to a nasal seal for a respiratory therapy mask for contacting the face of a user. The nasal seal comprises a main body and at least one nasal prong. The main body comprises at least one side wall and a fluid inlet, the main body defining at least a portion of a cavity. The nasal prong is configured for the delivery of fluid to the user's nares, the nasal prong comprising a base adjacent the mask body, a tip defining a prong outlet, and a prong wall extending between the base and the tip. The nasal prong defines a prong cavity, and further comprises a web extending across the prong cavity.

The web may be configured to reduce the likelihood of flipping or inversion of the prongs.

In an embodiment, the web comprises a lower edge proximal to the base, and an upper edge, wherein at least a portion of the upper edge is spaced from the tip of the prong.

In an embodiment, the upper edge comprises a central portion spaced from the tip of the prong and side portions extending from the central portion to the prong wall. The side portions may form a curved transition from the central portion of the upper edge to the respective internal surface of the prong wall.

In an embodiment, a distance between the two side portions at or adjacent the tip of the prong is greater than a distance between the two side portions at or adjacent the central portion of the upper edge.

In an embodiment, the central portion of the upper edge comprises a length that is greater than about 2.3 mm and/or less than about 3.8 mm, preferably between about 2.3 mm and about 3.8 mm, for example about 3.3 mm.

In an embodiment, the side portions of the upper edge comprise a first side portion and a second side portion, wherein the first side portion is longer than the second side portion.

In an embodiment, the side portions of the upper edge comprise a first side portion and a second side portion, comprises a length that is greater than about 3.8 mm and/or less than about 4.7 mm, preferably between about 3.8 mm and about 4.7 mm.

In an embodiment, the side portions of the upper edge comprise a first side portion and a second side portion, wherein the second side portion comprises a length that is greater than about 3.3 mm and/or less than about 4.4 mm, preferably between about 3.3 mm and about 4.4 mm.

In an embodiment, the web is integrally formed with the nasal mask such that the web is continuous with the prong wall.

In an embodiment, the prong cavity has a cross-section with a major axis and a minor axis, and each web extends generally along the minor axis, or substantially parallel to the minor axis.

In an embodiment, the web has a width that is larger than a linear distance between opposing interior surfaces of the prong wall of the prong in the minor axis or plane. The web may have a curvature. The curvature may enable compression of the prong in both a minor direction and a major direction. For example, compression in the major direction may lead to the stretching and/or straightening of the web across its width; and/or compression in the major direction may lead to the flattening and/or tensioning the web.

In an embodiment, compression in the minor direction causes an increase in the curvature of the web.

In an embodiment, the nasal prong is a first nasal prong, and the nasal seal further comprises a second nasal prong, the second nasal prong having any one or more of the above features described in relation to the first nasal prong. Preferably the second nasal prong is substantially the same as the first nasal prong, although the orientation of the nasal prong may vary, for example, the first and second nasal prongs may be symmetrical.

In an embodiment, the nasal seal comprises two nasal prongs, with the tips of the nasal prongs projecting rearward beyond a rear surface of the nasal seal main body. \

In a third aspect the present disclosure relates to a nasal seal for a respiratory therapy mask for contacting the face of a user, the nasal seal comprising a resilient material and having a main body defining a cavity and a fluid inlet; and further comprising two nasal prongs projecting from the main body for the delivery of fluid to the user's nares; wherein a terminal region of each nasal prong has a wall thickness that tapers towards a tip of the nasal prong, wherein the wall thickness at the tips of the nasal prongs is less than 20% of the thickness of the nasal prong wall in a main un-tapered portion of the nasal prong.

The nasal seal may have one or more of the features described above in relation to the first aspect. For example, in the terminal regions, the nasal prong wall thickness may gradually decreases over a distance of about 2 mm, and/or the terminal regions may have a taper with a varying chord length and a varying radius of curvature.

In a fourth aspect the present disclosure relates to a frame for a nasal respiratory mask. The frame comprises an inlet and an outlet; with an upper outwardly protruding flange adjacent the outlet, and a lower outwardly protruding flange adjacent the outlet, the upper outwardly protruding flange and the lower outwardly protruding flange for positively engaging a nasal seal, wherein a length of the lower outwardly protruding flange is greater than a length of the upper outwardly protruding flange.

In an embodiment, the frame comprises a seal retaining rim adjacent the frame outlet. The seal-retaining rim may be substantially D-shaped for example, to complement a D-shaped inlet of a complementary nasal seal. In one embodiment, the seal retaining rim comprises an upper surface, a lower surface, and two opposite side surfaces extending between the upper and bottom surfaces. In an embodiment, the upper surface of the seal retaining rim is narrower than the lower surface of the seal retaining rim. For example, the lower surface of the seal retaining rim may have a width from about 1.5 to about 2 times the width of the upper surface of the seal retaining rim. In one embodiment, the lower surface of the seal retaining rim has a width of about 1.8 times the width of the upper surface of the seal retaining rim.

The upper and lower flanges may protrude from the seal retaining rim by a depth that substantially corresponds to the surface of the lip on the complementary nasal seal. In one embodiment the flanges project about 1 mm from the respective surface of the seal retaining rim.

In an embodiment, the lower flange is wider than the upper flange.

In an embodiment the lower flange is provided along a rear edge of the lower surface of the seal retaining rim. In an embodiment the upper flange is provided along a rear edge of the upper surface of the seal retaining rim.

The upper flange may extend along at least a major length of the upper surface of the seal retaining rim; the lower flange may extend along at least a major length of the lower surface of the seal retaining rim. In an embodiment, the upper flange extends along substantially the whole length of the upper surface of the seal retaining rim. In an embodiment, the lower flange extends along substantially the whole length of the lower surface of the seal retaining rim.

That is, the upper flange may extend along at least a major length of an upper edge of the inlet, and the lower flange may extend along at least a major length of a lower edge of the inlet. In an embodiment, the upper flange extends along substantially the whole length of the upper edge of the inlet. In an embodiment, the lower flange extends along substantially the whole length of the lower edge of the inlet.

The corners of the seal retaining rim where the side surfaces adjoin the upper and lower surfaces, may be curved. The two corners on each of the upper and lower flanges may be curved.

In an embodiment the outlet is substantially D-shaped.

In an embodiment, the depth of the seal retaining rim varies around the perimeter of the rim. In one embodiment, the rim side surfaces have a depth of about 3 mm and the upper and lower rim surfaces have a depth of about 3.5 mm.

In an embodiment, the distance between the upper flange and the inlet 15 is larger than a distance from the lower flange to the inlet 15.

In an embodiment, a collar is provided at the inlet for coupling a fluid conduit to the frame.

The frame may include a series of bias flow apertures adjacent the inlet, the bias flow apertures being arranged along an arc. In an embodiment, the frame includes two arcuate rows of bias flow apertures, provided on opposite sides of the inlet. In an embodiment, each row consists of between 10 and 16 bias flow apertures, inclusive, more preferably between 12 and 14 apertures, inclusive.

In an embodiment, the bias flow apertures are provided in an inflection region between a collar at the inlet and a main body of the frame, for example through the surface of a fillet extending between a conduit connector at the outlet and the main body of the frame.

In an embodiment, the bias flow apertures are angled to direct airflow forwards and outwards. That is, airflow from the apertures does not impinge on any surface of the frame. In an embodiment, the bias flow apertures are spaced with centres of adjacent bias flow apertures being about 1.2 mm apart, and/or the axes of adjacent apertures forming an angle of about 7 degrees.

In an alternative embodiment, the frame comprises one or more diffusion aperture(s) provided in the frame, in communication with the fluid chamber. The diffusion apertures may comprise generally triangular apertures positioned on left and right sides adjacent the inlet; a single rectangular, oval, or trapezoidal aperture positioned in an upper region of the frame; or may comprise one or more alternatively shaped apertures.

In an embodiment, the frame inlet forms an angle of about 30 degrees with the frame outlet.

In an embodiment, the diffusion aperture comprises an aperture adjacent the upper outwardly protruding flange, and the frame further comprises a plurality of channels in fluid communication with the aperture and extending away from the aperture. The channels may comprise diverging grooves. The channels may be arranged to be positioned under the pull tab of a nasal seal.

An air-permeable diffuser mat is provided over the, or each, diffusion apertures. The diffuser mat may be overmoulded with the frame.

In an embodiment, the frame is a two-part frame comprising a main body and a diffusion clip that is engagable with the main body, and wherein the diffusion clip comprises one or more diffusion aperture(s) arranged to be in communication with the fluid chamber.

In an embodiment, the frame further comprises coupling arms with coupling features configured for attaching the frame to head gear, the coupling features being provided at an angle such that the reaction force from the headgear will be substantially evenly distributed over an attached nasal seal to enhance the seal with the user. The coupling features may comprise one or more of, an aperture, a clip, a post, a receptacle, or a detent, to receive a complementary feature on the attaching headgear.

In an embodiment, the coupling arms each comprise a convex rear surface. In an embodiment, curvature of the convex rear surface corresponds to the curvature of the lip surrounding the inlet on the attaching nasal seal. In one embodiment, the convex rear surfaces have a radius of about 25 mm and a centre of curvature that is forward of the nasal seal.

In an embodiment, the frame comprises a pull-tab alignment surface, the surface comprising a flattened surface on an upper surface of the frame, forward of the outlet, to align with a pull-tab on a complementary nasal seal.

In a fifth aspect, the present disclosure relates to a frame assembly for a nasal respiratory mask. The frame assembly comprises a frame as described above in relation to the second and third aspects, and a connector for coupling the frame to a conduit, wherein the connector comprises one or more diffusion apertures.

In an embodiment, a series of apertures provided annularly on the connector. An annular air-permeable diffuser mat may be provided over the diffusion apertures.

In an embodiment, the frame comprises one or more air blocking tabs arranged to prevent airflow from the diffusion apertures in the region of the air blocking tabs.

In an embodiment, the connector is overmoulded with the conduit.

In a sixth aspect, the present disclosure relates to a respiratory mask. The respiratory mask comprising a frame as described above in relation to the fourth aspect, and a nasal seal as described above in relation to the first or second aspects. The frame is configured to connect to headgear, and the nasal seal is deformed or deformable around a portion of the frame and biased into engagement with the frame.

In a seventh aspect, the present disclosure relates to a respiratory mask, comprising a frame as described above in relation to the fourth aspect, configured to connect to headgear, and a nasal seal for contacting the face of a user. The nasal seal comprises at least one nasal prong configured for the delivery of fluid to the user's nares, the nasal prong comprising a base adjacent the main body, a tip defining a prong outlet, and a prong wall extending between the base and the tip, and the nasal prong defines a prong cavity. The upper outwardly protruding flange is engaged or engagable with a top of the nasal seal fluid inlet and the lower outwardly protruding flange is engaged or engageable with a lower part of the nasal seal fluid inlet, and the nasal seal is engaged or engagable with the frame by deforming the seal around a portion of the frame.

In an embodiment, the upper flange of the frame is engaged or engageable with a top of the nasal seal fluid inlet and the frame lower flange is engaged or engageable with a lower part of the nasal seal fluid inlet. For example, in one embodiment, the nasal seal has an interior lip adjacent the nasal seal inlet, the upper flange of the frame is engaged or engageable with a top of portion of the lip and the frame lower flange is engaged or engageable with a lower portion of the lip. In an embodiment, side portions of the lip abut side portions of the seal retaining rim when the seal is engaged with the frame.

In an embodiment the frame has a seal retaining rim adjacent the frame outlet on which the seal inlet rests. The fluid inlet on the nasal seal may be narrower and/or shorter than the seal retaining rim on the frame, thereby ensuring that the nasal seal is in tension when it is fitted to the frame.

In an embodiment, the nasal seal comprises a pull tab adjacent a top of the nasal seal fluid inlet, to aid engagement of the nasal seal with the frame and removal of the nasal seal from the frame.

In an embodiment, one or more diffusion aperture(s) are provided in the frame, in communication with the fluid chamber, and a front edge of the diffusion aperture is forward of a front edge of the pull tab.

In an embodiment, the respiratory mask further comprises a connector for coupling the frame to a conduit. The connector comprises one or more diffusion apertures. The diffusion apertures may comprise a series of apertures provided annularly on the connector.

In an embodiment, the connector comprises an annular air-permeable diffuser mat provided over the diffusion apertures.

In an embodiment, the frame comprises one or more air blocking tabs arranged to prevent airflow from the diffusion apertures in the region of the air blocking tabs.

In an embodiment, the respiratory mask comprises a conduit, with an end of the conduit being overmoulded to the connector.

The term 'comprising' as used in this specification and claims means 'consisting at least in part of'. When interpreting statements in this specification and claims that include the term 'comprising', other features besides those prefaced by this term can also be present. Related terms such as 'comprise' and 'comprised' are to be interpreted in a similar manner.

It is intended that reference to a range of numbers disclosed herein (for example, 1 to 10) also incorporates reference to all rational numbers within that range and any range of rational numbers within that range (for example, 1 to 6, 1.5 to 5.5 and 3.1 to 10). Therefore, all sub-ranges of all ranges expressly disclosed herein are hereby expressly disclosed.

As used herein the term '(s)' following a noun means the plural and/or singular form of that noun. As used herein the term 'and/or' means 'and' or 'or', or where the context allows, both.

As used herein the term 'about' means a measurement or other quantity is intended to include other measurements or quantities that vary from the specified value by an amount within a manufacturing or measurement tolerance.

BRIEF DESCRIPTION OF THE DRAWINGS

Embodiments will now be described by way of example only and with reference to the accompanying drawings in which:

FIG. 23A is a partial front view, and FIG. 23B is a side section view;

FIG. 58 is a side section view of a felt fibre mat for forming into a diffuser mat;

FIG. 59 is a partial side section view of the mat of FIG. 58 formed into a diffuser mat and overmoulded with a nasal seal support frame;

DETAILED DESCRIPTION

Various embodiments and methods of manufacture will now be described with reference to FIGS. 1 to 31. In these figures, like reference numbers are used to indicate like features.

Directional terminology used in the following description is for ease of description and reference only, it is not intended to be limiting. For example, the terms 'front', 'rear', 'upper', 'lower', and other related terms refer to the location of a part or portion of a respiratory mask relative to a user when the user is wearing the respiratory mask. In this specification, 'rear' refers to a location that is proximal to the user (when the mask is in use) and 'front' refers to a location that is distal to the user by comparison. The terms 'upper' and 'lower' refer to the location of a part or component of a mask relative to the rest of the mask when the mask is in use and the user is sitting in an upright position. An arrow F has been included in the figures where appropriate to indicate the forward direction of the device.

Figure 1:
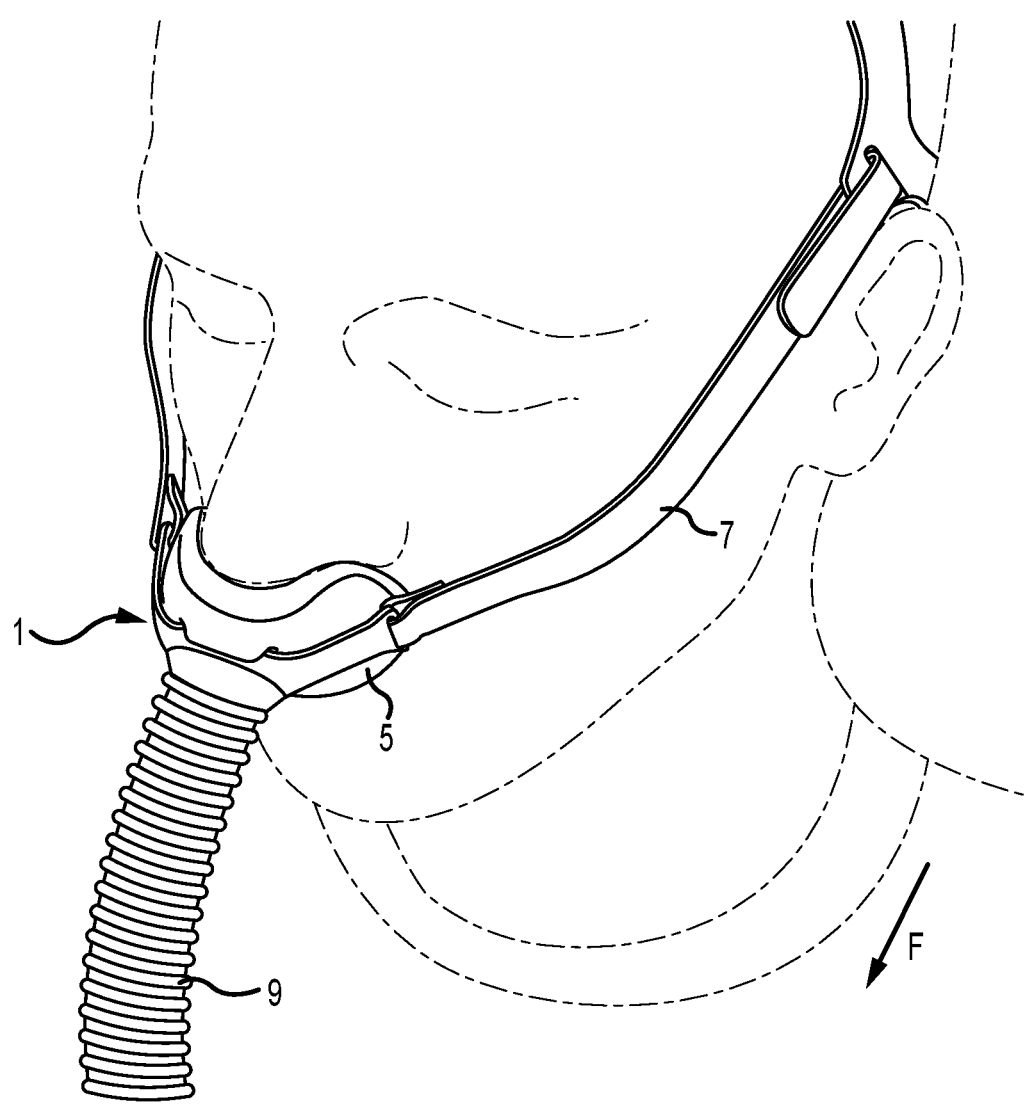
FIG. 1 is an illustrative view showing a user wearing an exemplary respiratory user interface including a head strap, frame, and nasal seal, the interface being connected to a supply conduit.

FIG. 1 shows and exemplary embodiment nasal respiratory interface 1. The respiratory interface comprises a frame 3 with headgear 7 attached to connectors 13 on the frame, and a nasal seal 5 for sealing with the face of a user to supply respiratory gasses nasally to the user. The nasal seal 5 is removably mounted to the frame 3. A fluid supply conduit 9 is coupled to a fluid inlet 15 on the frame for the supply of breathing gasses to a user.

FIGS. 7 to 14 show the nasal seal component 5. The nasal seal 5 comprises a main body 10, and two nasal prongs 11 projecting from the main body 10 for the delivery of fluid into the nares of a user. The main body 10 defines a main cavity 19 and fluid inlet 17 allowing ingress of fluid into the cavity 19. The nasal seal 5 comprises a resilient material such as silicone, such that the nasal seal 5 has a self-supporting shape but is able to deflect and conform to contours of a user's face.

In use, the nasal prongs 11 are positioned at least partly in or at the base of the nostrils of a user to direct fluid into the nasal passages. The nasal prongs 11 have a nare sealing region to contact an inner surface of the nares and create at least a partial seal with the nares.

At least a portion of a rear facing surface A2 (FIG. 31) of the nasal seal main body 10 contacts the face of a user to form a secondary seal with the face. The rear surface may contact the user's face at one or more of a region below the nose, beside the nose, or over the tip of the nose. This contact between the user's face and the main body 10, creates a secondary seal, which acts as a back-up seal to compensate for leakage in the seal that may occur between the nares and the nasal prongs 11. This contact also provides support to stabilise the mask on the user's face. The nasal seal main body 10 is may be contoured to fit closely to a user's face and may be available in different sizes or geometries to accommodate different users.

Figures 31, 32:
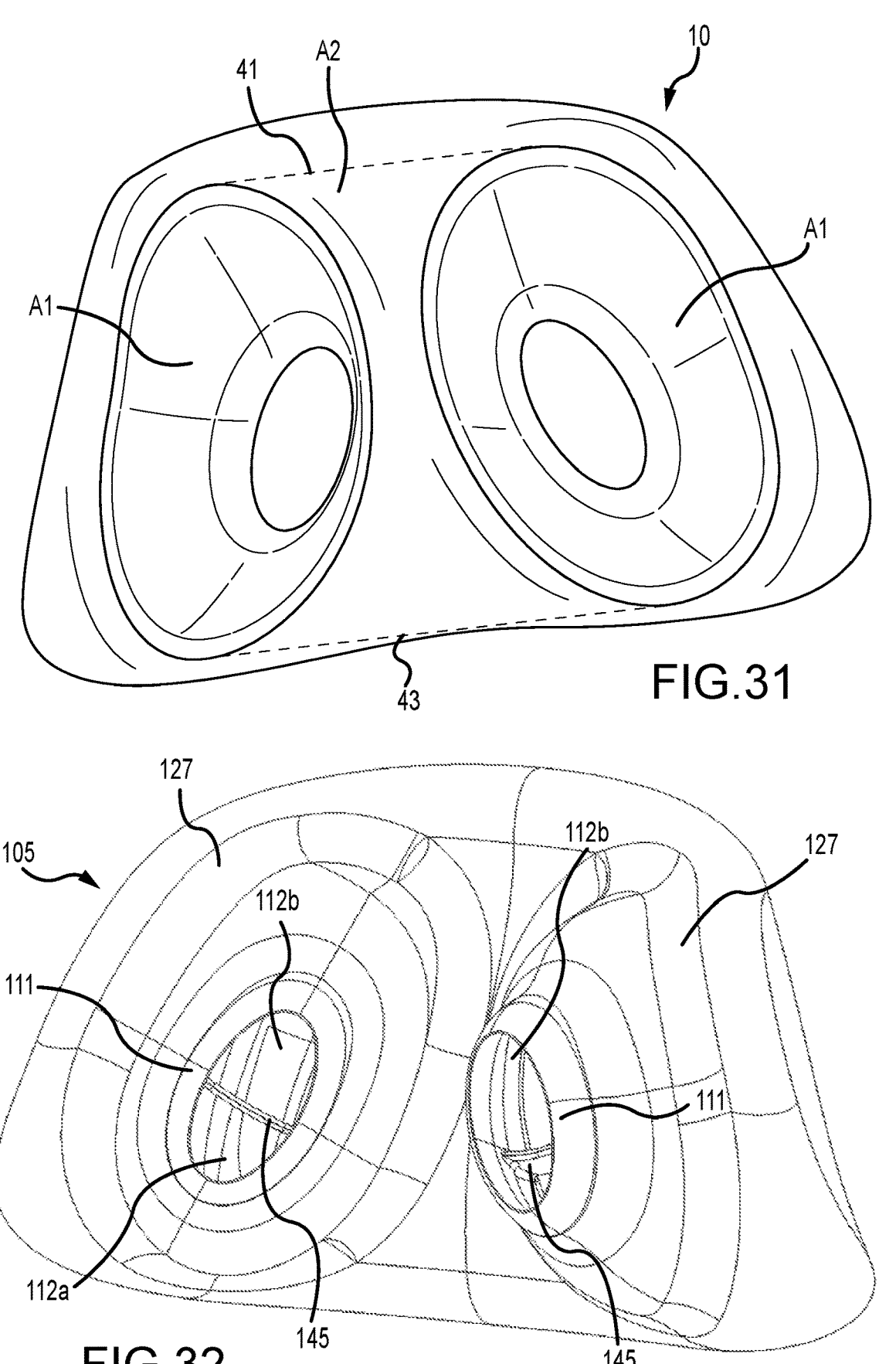
FIG. 31 is a rear view of the nasal seal, illustrating the comparative surface areas of the nasal prongs and the secondary sealing surface.
FIG. 32 is a rear perspective view of a second embodiment nasal seal having webs in the nasal prongs.

With reference to FIG. 31, the user contacting rear surface A2 of the seal main body 10 has a surface area of about 544 $mm^2$, but this may vary in different embodiments and with the size of the mask. Substantially the whole of the rear facing surface A2 (as shaded in FIG. 31) may form the secondary seal, or alternatively the secondary seal may be formed only by the region of said surface between the prongs, between tangential lines 41, 43 at the tops and bottoms of the prongs, an area of around 170 $mm^2$. In comparison, the surface area of each prong is about 600 mm$^2$. It will be appreciated that these areas will vary between embodiments for different sized masks.

A superior secondary seal will, in general, be provided by a nasal seal with a large main body having thin walls, as the seal has large contact surface area to seal around the nose, and thin walls enable the seal to conform closely to the face by inflating ('ballooning') under pressure into the user's face. However, the large size of these larger seals, which often sit against the cheeks and as high as the nose bridge of a user, can be a deterrent to therapy compliance because of their intimidating and obtrusive appearance.

In the nasal seal 5 presently described, the main body 10 is compact to provide a less obtrusive option. The main body 10 in the nasal seal 5 primarily serves to connect the two nasal prongs 11. For example, in the embodiment shown, at its widest point the exemplary nasal seal 5 is about 50 mm, and the seal 5 is about 30 mm at its maximum vertical dimension. In the embodiment shown, this represents a reduction of about 25% in width and height of the seal compared to existing masks of a comparable fit size. However, it will be apparent that these dimensions will vary in seals of different sizes to fit different groups of users.

Figure 2:
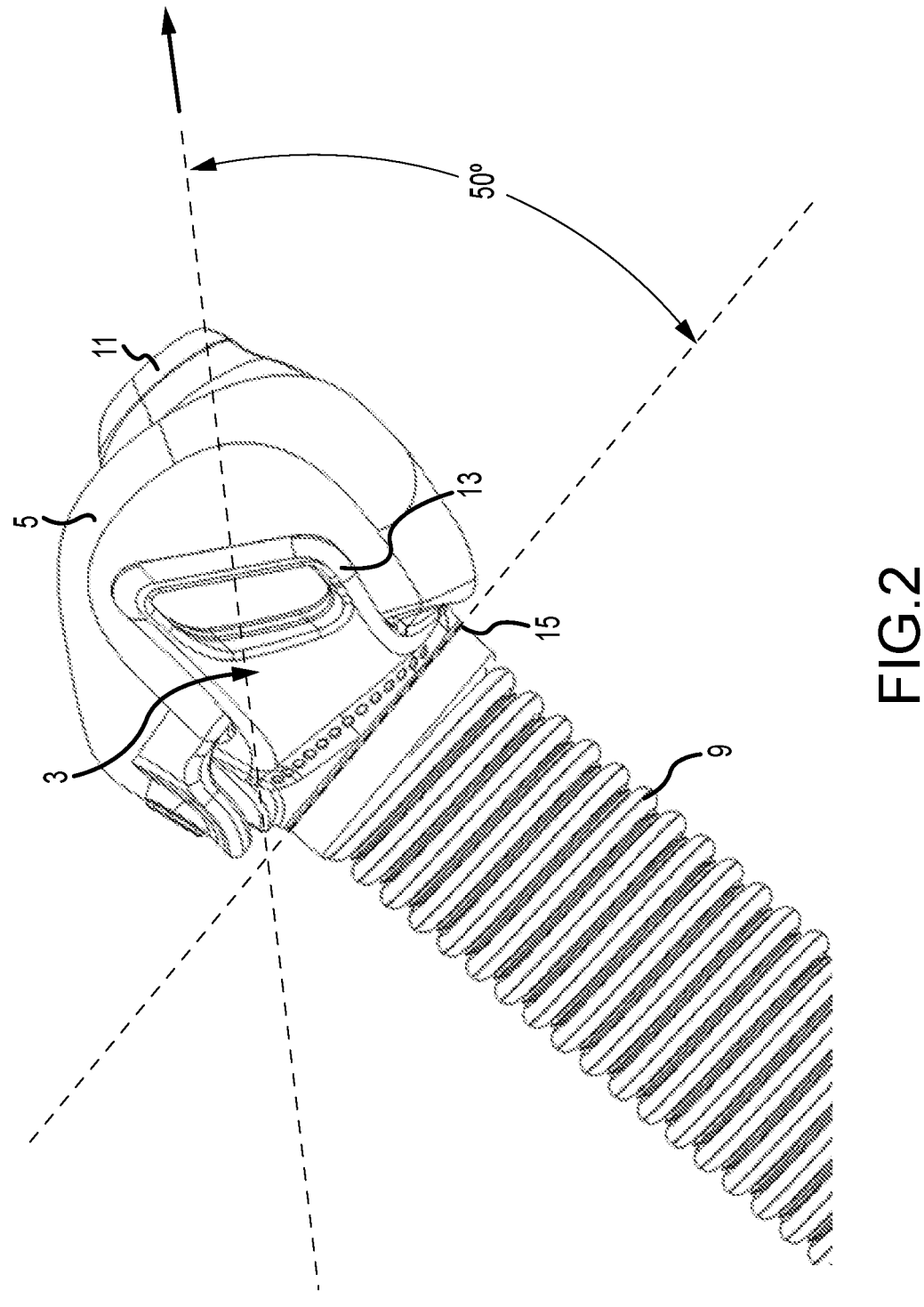
FIG. 2 is a side view of the respiratory interface of FIG. 1, with the supply conduit connected but the headgear removed, and showing the relative angles of the user interface components.
Figures 9, 10:
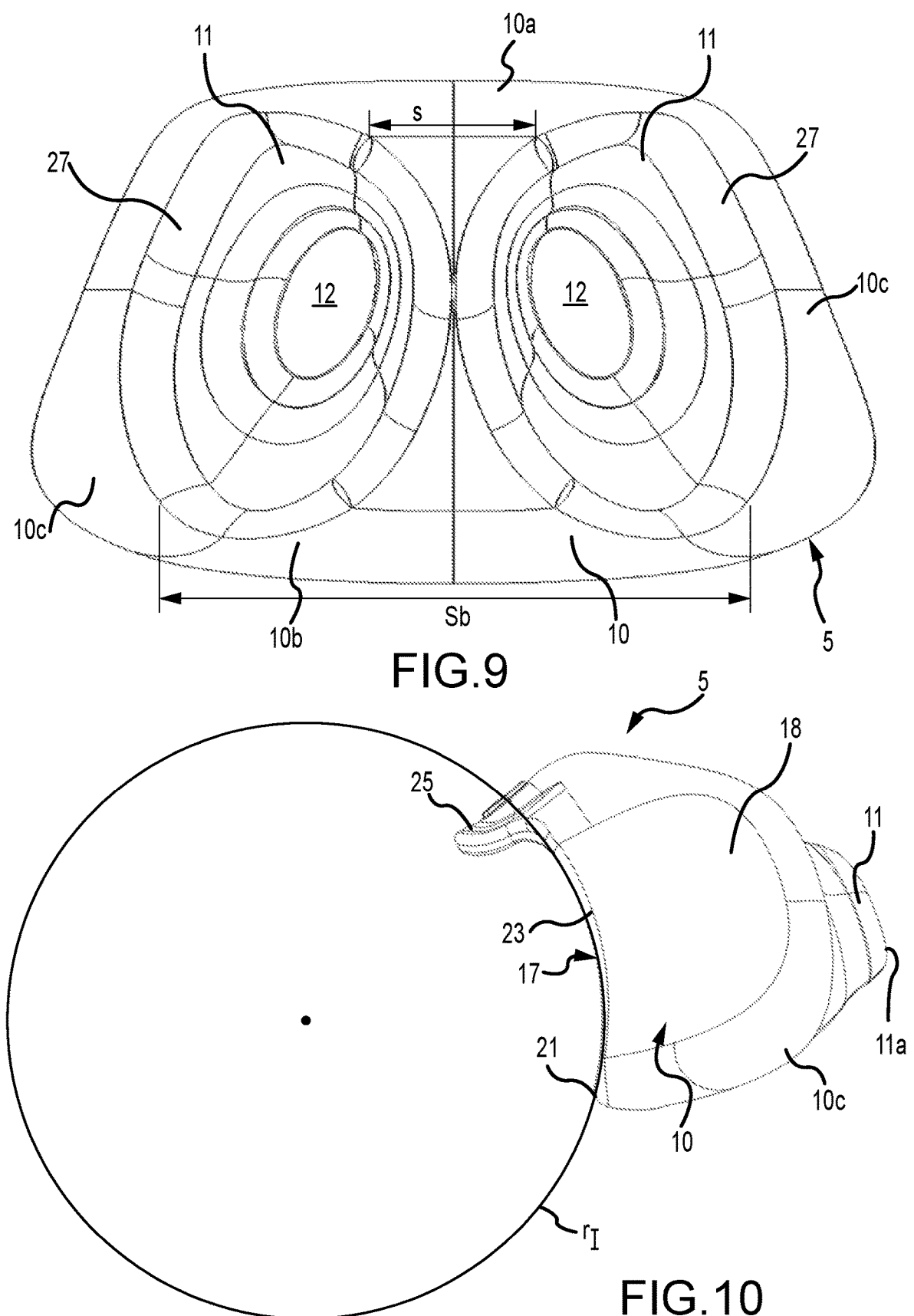
FIG. 9 is a wireframe rear elevation view of the nasal seal of FIGS. 7 and 8.
FIG. 10 is a side elevation view of the nasal seal of FIGS. 7 to 9, schematically showing the geometry of the front edge of the seal and fluid inlet.

As illustrated in FIGS. 2 and 10, as a result of the compact main body, no part of the nasal seal main body 10 extends rearward of the tip 11a of the nasal prongs 11. That is, no part of the main body of the nasal seal 10 protrudes rear of the prong tips 11a for sealing with the cheeks or the bridge of the nose.

Referring to FIG. 9, at the rear surface of the seal 5, the top 10a of the nasal seal main body 10 is narrower than the bottom 10b of the seal. The perimeter of the seal 5 closely relates to the size and orientation of the bases of the two prongs 11, as to accommodate the bases of the two prongs 11. It can be seen from FIG. 9 that the major axes of the nasal prong cavities are spaced further apart Sb at a bottom of the prongs 11 than the tips 11a (St).

The rear patient facing/contacting surface 10c of the nasal seal 5 is concave to complement the convex surface of a user's face, such that the bottom part 10b of the main body 10 contacts a user's face below their nose to form a main secondary sealing surface for preventing or reducing under nose leaks. As described above, this compact configuration has a more discrete appearance and is less obtrusive, as commonly desired by home users of CPAP.

However, as described above, compared to larger seals, this more compact size provides a reduced contact surface with a user's face. The reduced height and width of the presently described nasal seal means that the seal 5 sits lower on the wearer's nose and in some cases may not cover the tip of the wearer's nose, and does not extend far over the cheeks. Therefore, the present compact mask is unable to rely on a large surface contact area to provide stability of the mask on the user's face during use. Stability of the mask is important in CPAP particularly where therapy is carried out overnight—it is important that small movements by the user in their sleep do not move the mask out of sealing contact with the nares, in particular up/down movements of the mask.

To compensate for the reduced user-contacting surface area 10c, the side walls 18 have a thickness sufficient to maintain spacing between the frame 3 of the mask and the rear user-contacting rear surface 10c of the nasal seal, in particular under forces applied by the headwear during use. In the embodiment shown, the side walls 18 of the nasal mask 5 have a wall thickness of about 2 mm. This may be uniform at the side regions, or may gradually taper, for example towards thinner top and bottom regions.

In addition, the rear (user-contacting) wall 10c of the main body 10 has a wall thickness that is selected to ensure the seal does not collapse/flatten in use under pressure from connecting headgear 7 nares and which provides stability to the mask to adequately support the prongs 11. In the embodiment shown, the rear (user-contacting) wall of the main body 10 has a wall thickness of about 0.45 mm. In other words, the rear wall thickness is less than 25% of the thickness of the nasal seal side walls 18. However, it is envisaged that this may be slightly thicker or thinner in alternative embodiments, for example in the range of 0.25 mm to about 0.55 mm. The wall thickness of the nasal seal gradually decreases from the side walls 18 to the rear (user-contacting) wall 10c.

Figures 13, 14:
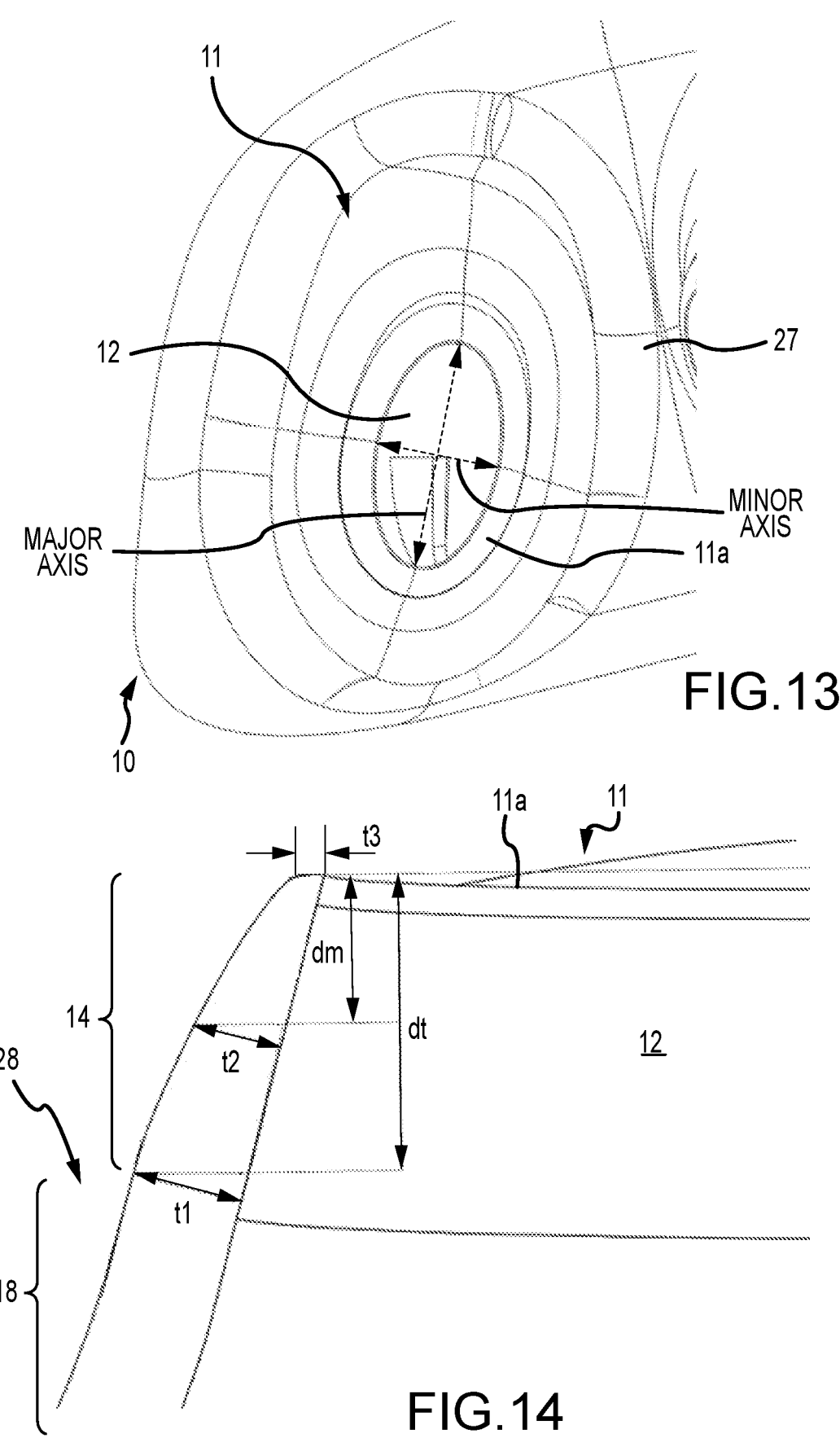
FIG. 13 is a wireframe rear detail view of one of the nasal prongs of the nasal seal of FIGS. 7 to 10.
FIG. 14 is a detail section view of a part of one of the nasal prongs, showing the taper of the wall thickness at the tip of the nasal prong.
Figures 15, 16:
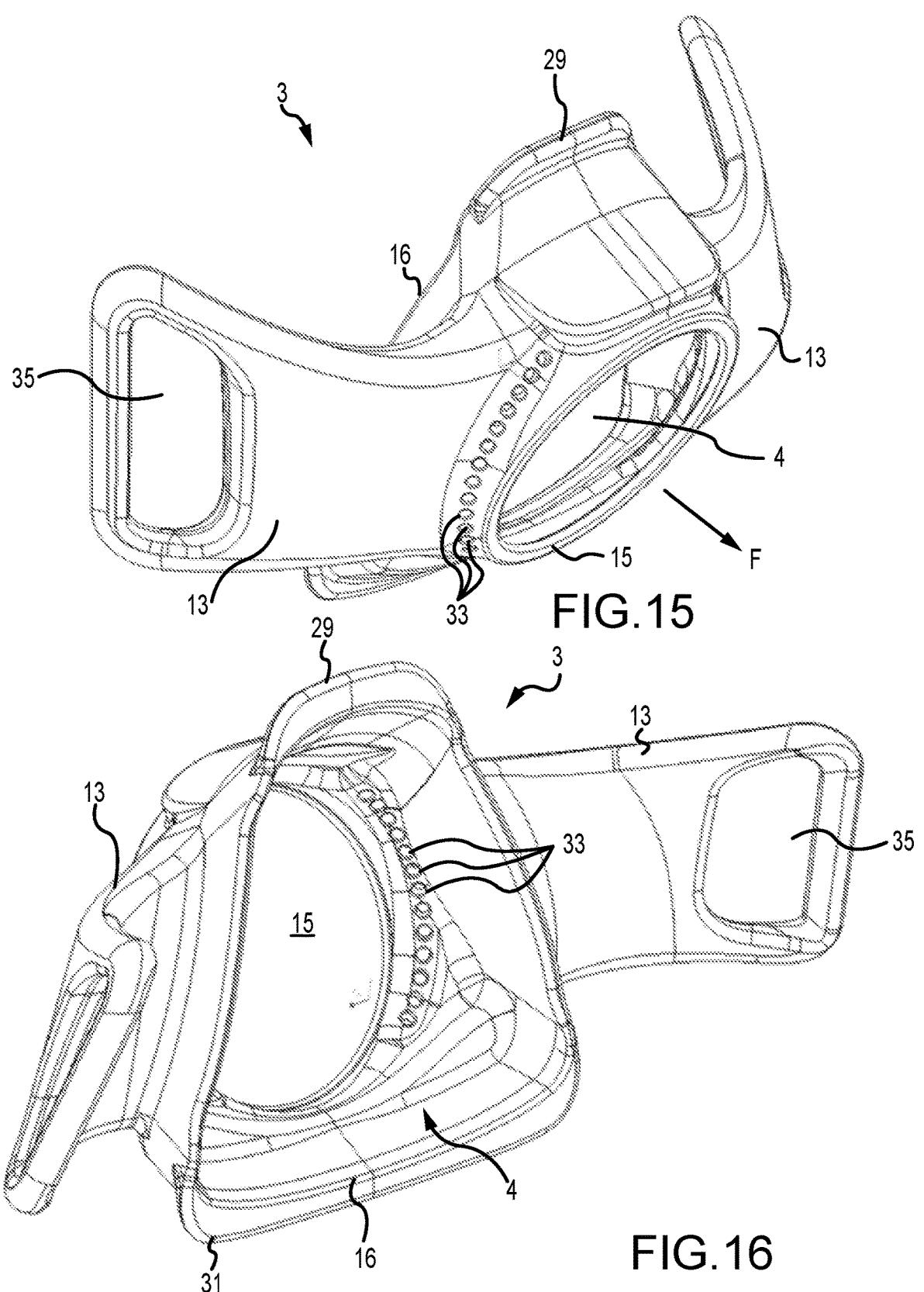
FIG. 15 is a front perspective view of an exemplary embodiment nasal seal support frame for the respiratory interface of FIG. 1.
FIG. 16 is a rear perspective view of the nasal seal support frame of FIG. 16.
Figure 17:
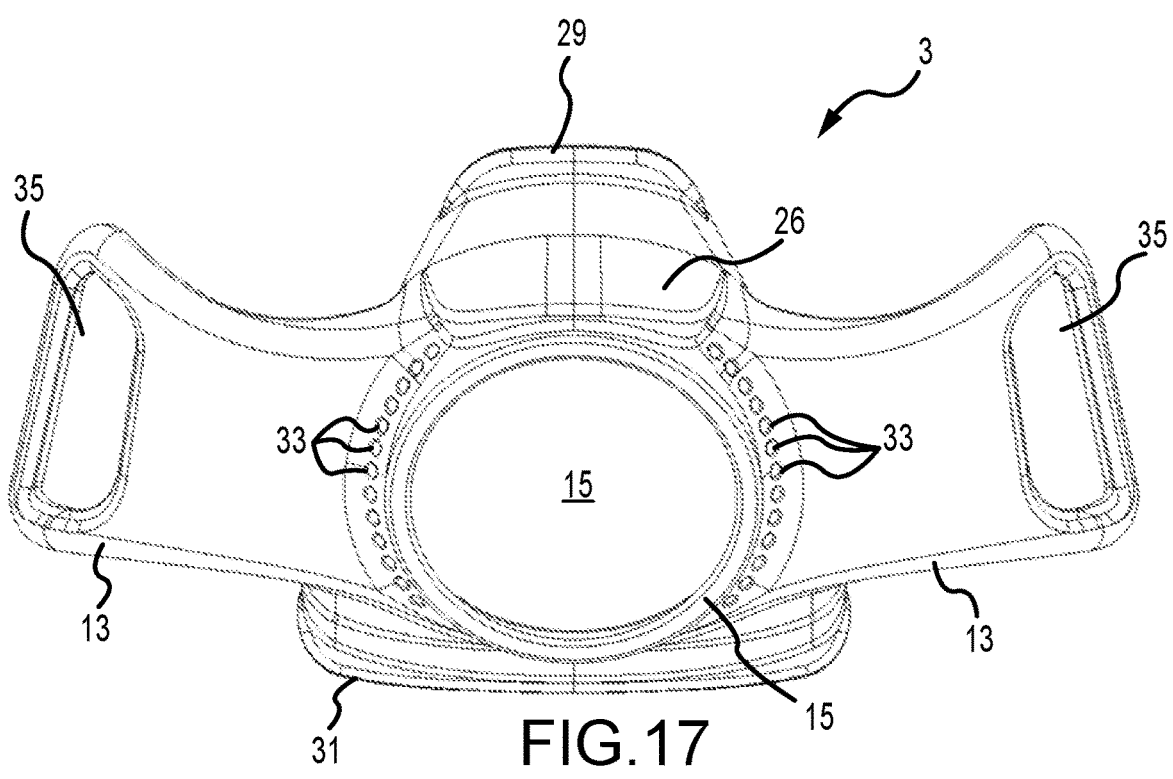
FIG. 17 is a front elevation view of the nasal seal support frame of FIGS. 15 and 16.
Figure 18:
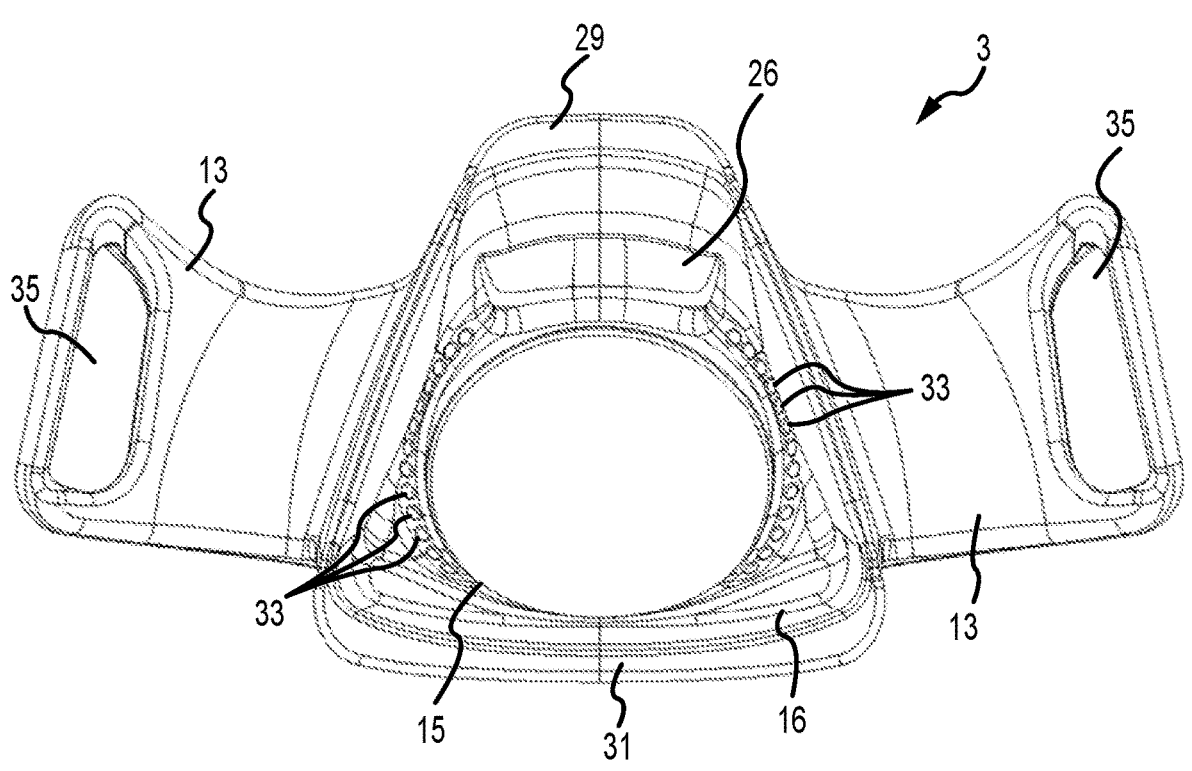
FIG. 18 is a rear elevation view of the nasal seal support frame of FIGS. 15 to 17.
Figure 19:
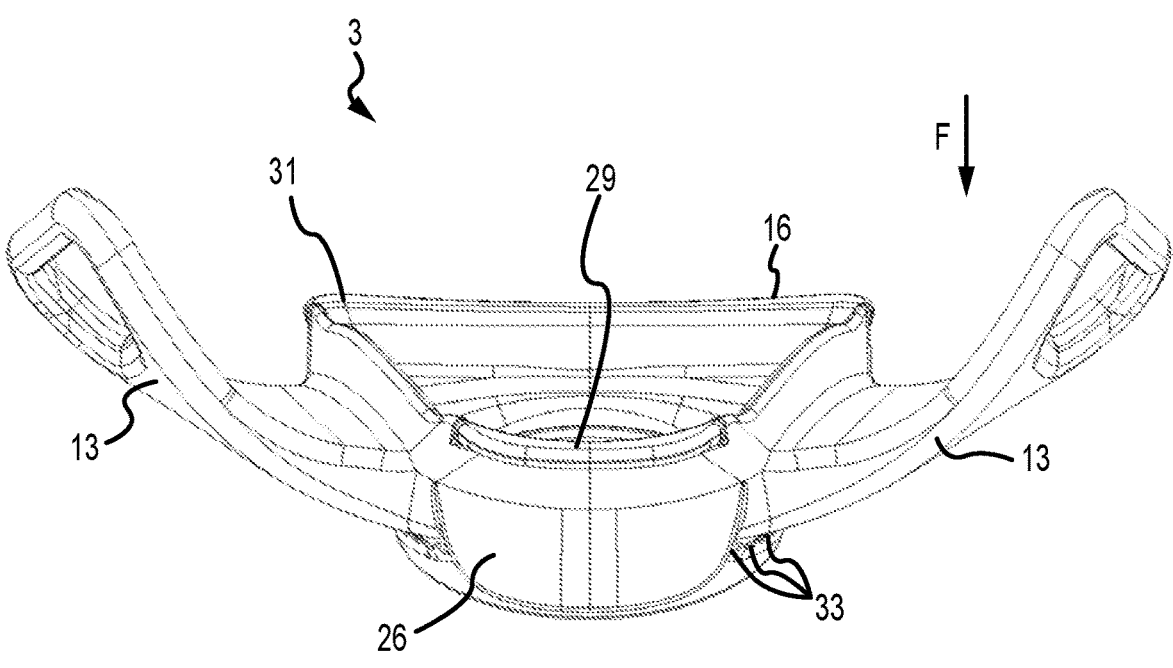
FIG. 19 is a top elevation view of the nasal seal support frame of FIGS. 15 to 18.
Figure 20:
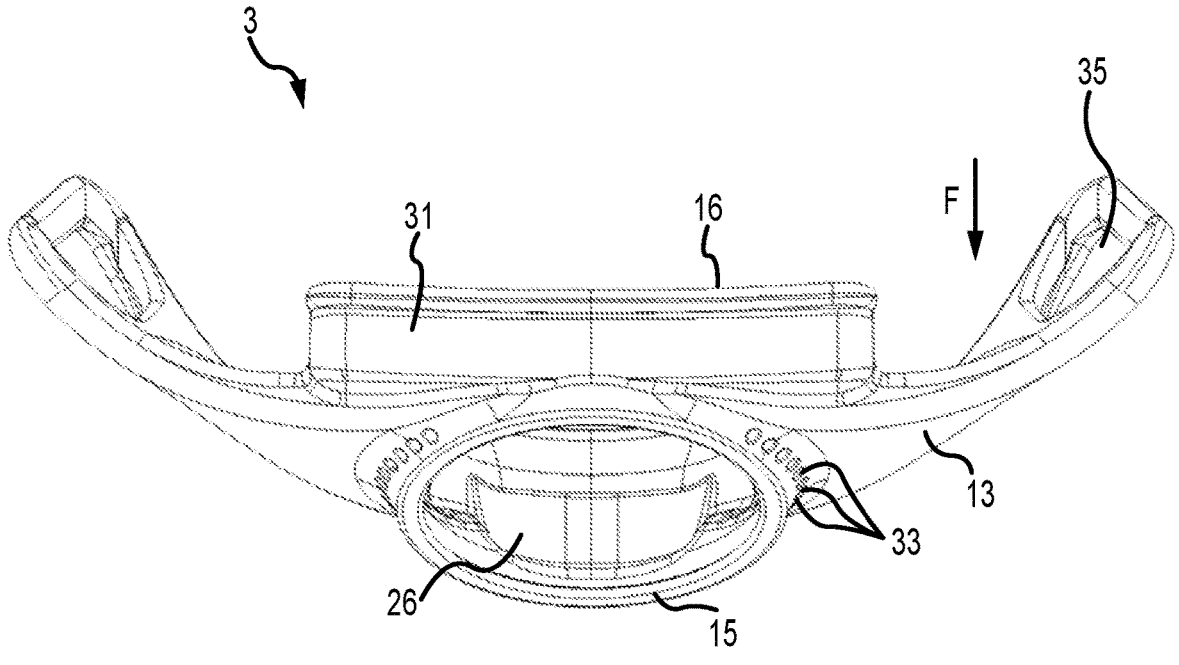
FIG. 20 is an underside elevation view of the nasal seal support frame of FIGS. 15 to 19.
Figures 21, 22A, 22B:
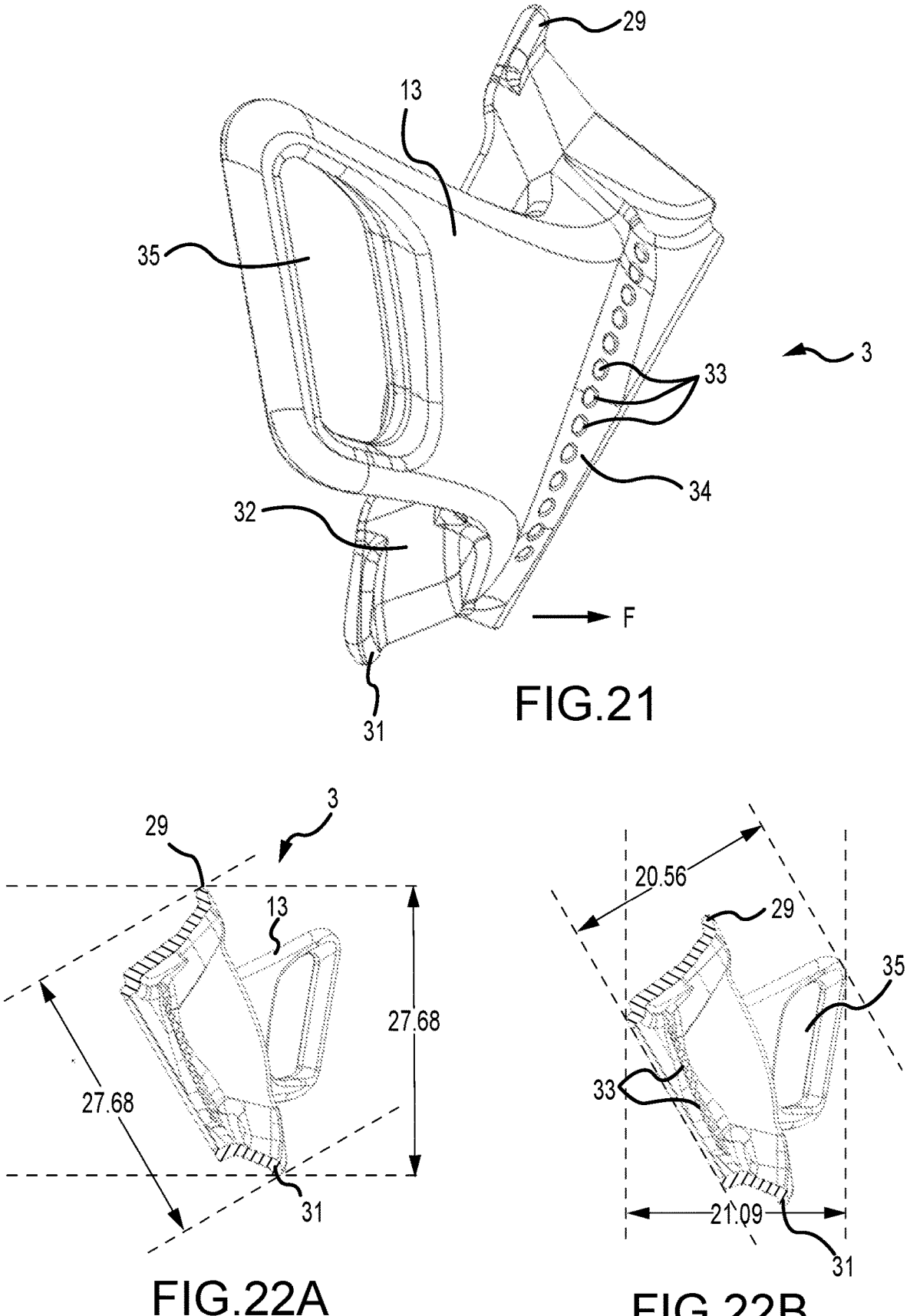
FIG. 21 is a side elevation view of the nasal seal support frame of FIGS. 15 to 20.
FIGS. 22A and 22B are side section views of the nasal seal support frame of FIGS. 15 to 21, illustrating dimensions of the frame.
Figure 23A:
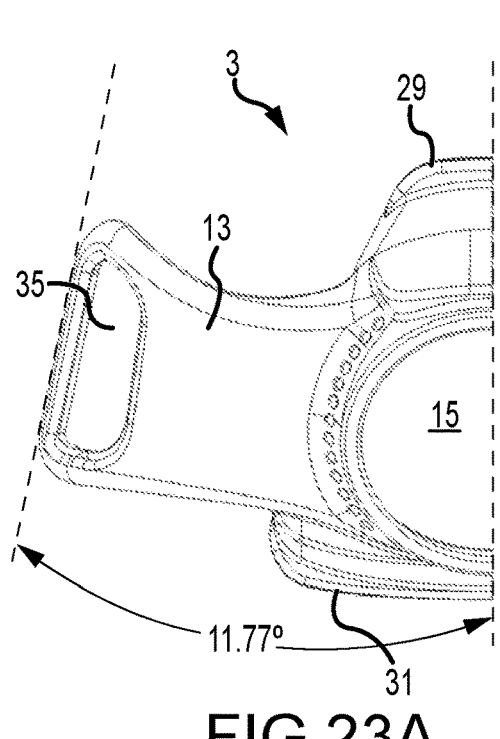
FIGS. 23A and 23B are views showing angular dimensions of the nasal seal support frame of FIGS. 25 to 21, where
Figure 23B:
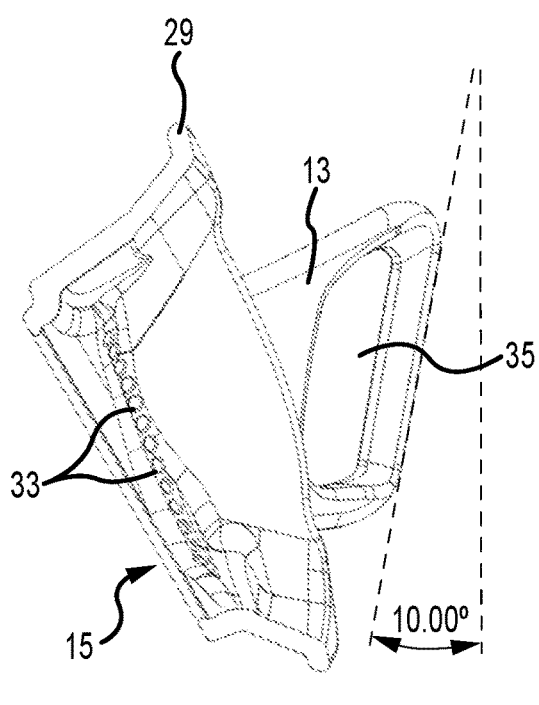
Figure 24:
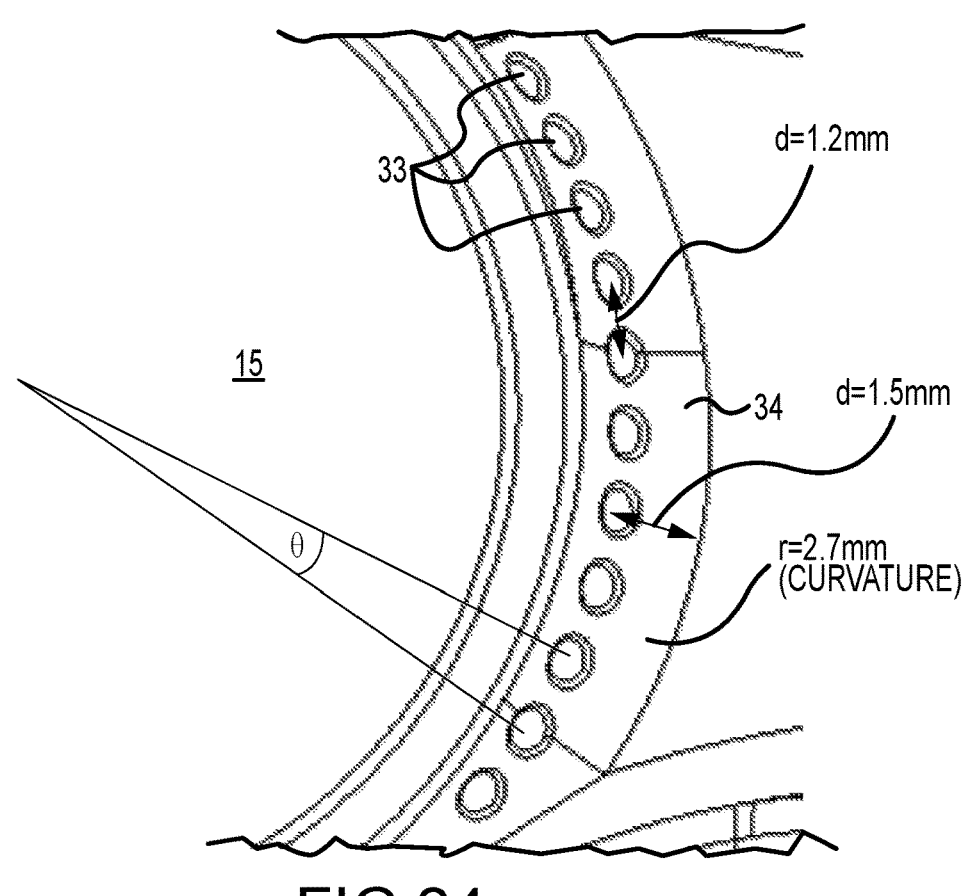
FIG. 24 is a detail view showing the bias flow holes in the nasal seal support frame adjacent the fluid inlet.

Referring in particular to FIGS. 9 and 13, each nasal prong 11 has a non-circular cross section that narrows non linearly from a base of the nasal prong 11b to a tip of the nasal prong 11a (FIG. 12), thereby defining a non-cylindrical cavity. The tip of the nasal prong 11a defines the prong outlet. In the embodiment shown, the nasal prong has an oval cross section having a major dimension and a minor dimension that are both larger at a base of the nasal prong 11b compared to at a tip of the nasal prong 11a. The non-circular cross section enables the nasal prongs to more closely follow the inner walls of the nostrils for comfort and to thereby achieve a better seal with the nasal passage. In addition, the narrowing of the nasal prong cavity helps reduce the likelihood of the nasal prongs inverting when they are in use, as internal pressure from the respiratory gasses help to bias the nasal prongs outwards. The nasal prong cavities 12 may be eccentric, that is the opening at the tip 11a of the prong is not centred over the opening at the base of the prong 11b, and/or the nasal prongs may be angled towards each other, for example, by virtue of each extending perpendicularly from a concave surface.

The non-circular shape of the nasal prongs 11 means that, at a given distance along the prong 11, the radius of curvature of the nasal prong exterior surface varies around the perimeter of the nasal prong, including at the base of the nasal prong 11b. In addition, the major and minor dimensions of the nasal prong cavity 12 do not necessarily change by the same amount from the base of the nasal prong 11b to the tip of the nasal prong 11a, for example, the nasal prong cavity may be eccentric. Therefore, the nasal prong wall steepness with respect to the seal main body 10 may also vary around the perimeter of the nasal prong.

In the present example, at the base of the prongs 11b, the surface transition from the nasal seal main body 10 to the prong is sharper (having a larger change in angle) at the sides of the nasal prong (i.e. in line with the minor axis of the cavity 12) than at the bottom of the nasal prong base 11b where the surface transition is more gradual.

In nasal masks having a radial fillet between the prong surface and main body surface, the width (chord) of the radial fillet depends on the angle between the two surfaces; the fillet will be wider where the angle between the two surfaces is more acute, and narrower where the change in angle is small. Therefore, variation in wall steepness around the perimeter of the nasal prongs 11 such as in the present embodiment, in combination with a radial fillet results in a fillet with a narrower width at the bottom of the prong where the change in angle from the secondary sealing surface to the prong is small. Because the transition between the wall thickness of the secondary seal and the wall thickness of the prong 11 occurs across the width of the fillet, a narrower fillet means a more sudden change in thickness. A sudden change in thickness results in creates a weakened or inflection region of reduced stiffness, at which the prongs more readily flex compared to other regions. While some flexing allows the cushion to adapt to different nose structures, too much flexing can cause collapse or inversion of the nasal prongs.

For example, in the present embodiment, at the bottom of the nasal prong base 11*b* where the angle between the prong wall surface and the main body 10 is most obtuse, a radial fillet would create a weaker region where the nasal prong is susceptible to fold or kink, for example due to movement of the mask. Thereby making the nasal prong 11 more reliant on the internal pressure from the respiratory gases during use to keep the nasal prong from inverting.

In contrast, in the nasal seal embodiment shown, at the base 11*b* of each nasal prong, there is a transition fillet 27 provided between the nasal prong 11 and the main body 10. The transition fillet 27 loops around the base of the prong 11 at its perimeter to create a smooth transition between the outer surface of the prong 11 and the rear surface of the main body 10 of the nasal seal 5. The transition fillet 27 has a constant chord length 27*a*. That is, the two edges defining the transition fillet 27 are parallel such that the 'width' of the transition fillet 27 is constant. Due to the changes in the wall angle and curvature of the nasal prong 11, the radius of curvature of the transition fillet varies around the perimeter of each prong.

The thickness of the seal wall in the region of the transition fillet 27 gradually transitions from matching the thickness of the main body rear wall (in this example, 0.45 mm), to the thickness of the nasal prong wall (in this instance about 0.8 mm). Since the fillet has a constant width, the transition between the wall thickness of the body rear wall and the prong wall is constant around the perimeter of the prong base, so there are no weaker regions due to sudden changes in wall thickness. In particular, this provides a stiffer transition at the base of the prong compared to the use of a radial fillet.

Figure 28:
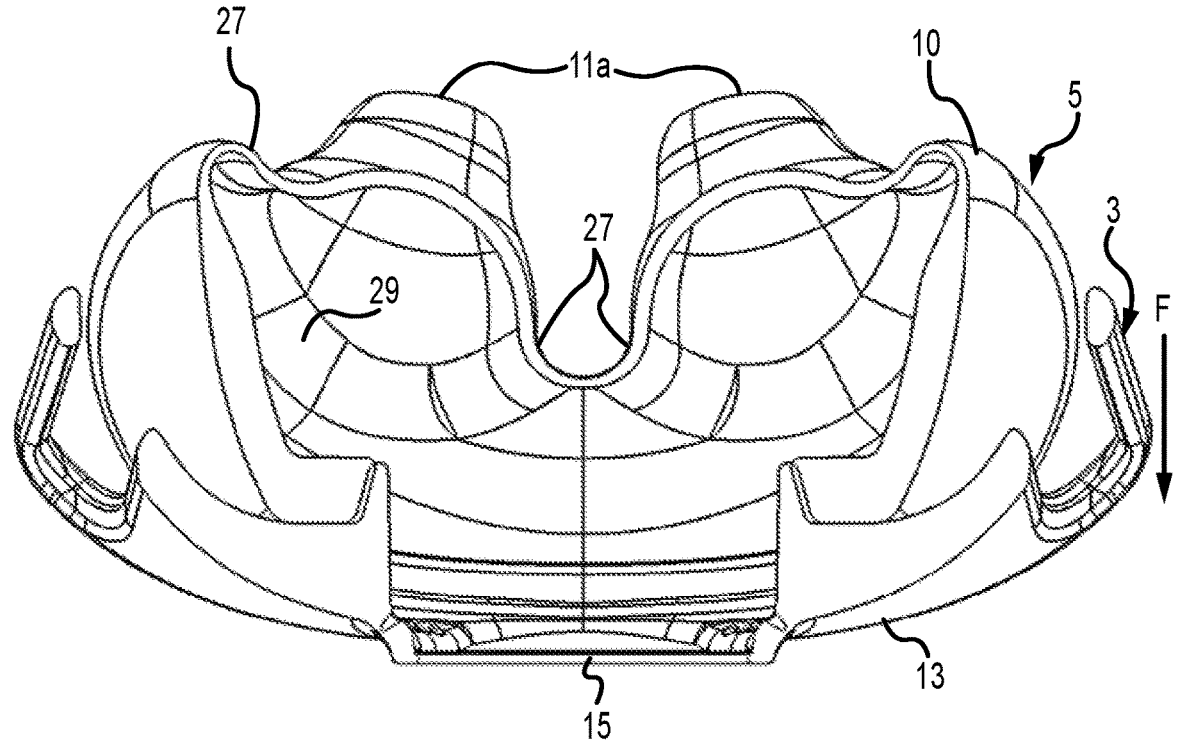
FIG. 28 is a top cut away view showing the engagement of the nasal seal with the frame.

On an interior surface of the nasal seal 10, at a base of the prong 11, a corresponding chordal round is formed (see FIG. 28). It is envisaged that these thicknesses may vary between embodiments, but preferably, the nasal prong thickness is less than about 2.5, more preferably less than 2, times the thickness of the adjoining rear wall of the nasal seal main body 10.

The constant chord length 27*a* of the transition fillet 27 provides each prong 11 with an area of flexing with substantially consistent stiffness along the fillet, thereby advantageously avoiding the creation of regions more prone to too much inflection or folding. The chordal fillet also gives the prong wall surface a smoother appearance which is more aesthetically pleasing. The chord length 27*a* for the chordal rounds may be selected to be as large as practical within the size constraints of the nasal seal main body 10, the distance between nasal prongs, and the depth of the nasal prongs. In the embodiment shown, the transition fillet has a chord length 27*a* of about 4 mm. The radius of curvature of the fillet varies from about 2 mm to about 9 mm along the fillet. However, the chord length 27*a* may vary between embodiments depending on the dimensions of the seal and the prong geometry.

Due to the compact nature of the secondary seal, forces from the headgear and forces from the flow of fluid into the mask are largely transmitted to the face of a user via the prongs, with a smaller component of the forces being dispersed via the secondary sealing surface compared to masks with a larger secondary sealing surface. A more gradual thin to thick transition between each prong 11 and the main body 10 advantageously produces a stiffer connection between the prong 11 and the main body 10 to accommodate these forces. This may reduce the occurrence of collapse or 'bottoming out' of the prongs during fitting and additionally will encourage the prongs to 'pop out' more easily when reverting, should they become inverted or collapse.

The thickness of the wall of each nasal prong 11 is substantially unchanged along a major part of the length of the prong. In the present example, the prongs are silicone and have a substantially uniform main wall thickness of about 0.8 mm and length of about 9.5 mm. However, it is envisaged that this wall thickness may change depending on material properties and the dimensions of the nasal prongs. The wall thickness may be selected such that the nasal prong is self-supporting and provides resistance to inversion or collapse of the nasal prong, particularly during fitting of the mask 1.

Each prong 11 has a terminal region 14 at a tip of the prong, and a nare sealing region 18, which extends from the base 11*b* of the prong 11 to the terminal region 14. The terminal region 14 of each nasal prong 11 has a wall thickness that tapers towards a tip of the nasal prong 11*a*. This tapering provides a softer, more compliant tip of the nasal prong 11*b* for comfort and for improved sealing. The taper and is provided by an external taper. The thinned region reduces pressure loading on the soft nose tissue in use, to reduce the likelihood of pressure sores.

In the present example, over the length of the terminal region 14, the wall thickness of the nasal prongs 11 gradually decreases from a thickness $t_1$ of about 0.8 mm to a thickness $t_3$ at the tip of about 0.1 mm. In alternative embodiments, the extent of the taper may vary, but preferably the wall thickness at the tip of the nasal prongs 11*a* is less than about 20% of the wall thickness of the un-tapered lower nare sealing region 18.

In the terminal regions 14, the nasal prong wall thickness gradually decreases over a distance di of about 2 mm, however, in alternative embodiments, the taper/terminal region 14 may be longer or slightly shorter. In the embodiment shown, the taper 14 is non-linear, forming a convex exterior surface with a radius of curvature that decreases towards a tip of the nasal prong 11*a*, and with a varying chord length. For example at a mid-point along the taper (dm of 1 mm), in the present example, the wall thickness $t_2$ is about 0.65 mm.

The exterior surface in the terminal region may be contoured to fit to the shape of a user's nares, for example.

The contour is such that the transition from the nare sealing region 18 to the terminal region 14 is gradual without sudden inflection. Referring to FIG. 14, at a base of the terminal region 14, the surface curvature of the nasal prongs 11 is such that it is tangential with the adjoining nare sealing region 18, so to create a smooth transition.

Between the prong base 11*b* and the terminal region 14, the nare sealing region 18 of the prong is contoured to provide a smooth transition between the terminal portion 14 and the base 11*b* of the prong 11. A major portion of the nare sealing region 18 comprises a convex outer surface to seal against the bottom of the user's nostrils. The convex surface bulges outwards in response to axial loading of the prongs, providing a cushioning effect. At a top of the nare sealing region 18, the convex surface transitions to a concave transition region 28, in turn adjoining the terminal portion 14 of the prong 11. In the embodiment shown, the concave region 28 contoured with a chordal round such that the contour is achieved over a height 18*a* that is constant around the prong 11.

This gradual taper together with the increased prong wall thickness in the nare sealing region, further assists with re-inverting the nasal prongs 11 should they become inverted or collapsed, and helps to bias them in their in-use configuration.

FIGS. 32 to 36A illustrate an alternative embodiment nasal mask 105 in which each nasal prong 111 comprises a web 145 to further reduce the likelihood of flipping or inversion of the prongs 111. In this embodiment, unless described otherwise, the seal is substantially as described in relation to the first embodiment, with like numbers used to indicate like parts, but with the addition of 100.

The web 145 is a thin member comprising a flexible resilient material, preferably the same material as the prongs, for example as silicone. The webs 145 may be integrally formed with the nasal mask 15 such that the web 145 is continuous with the interior walls of the prongs 111.

Figures 33A, 33B, 34A, 34B:
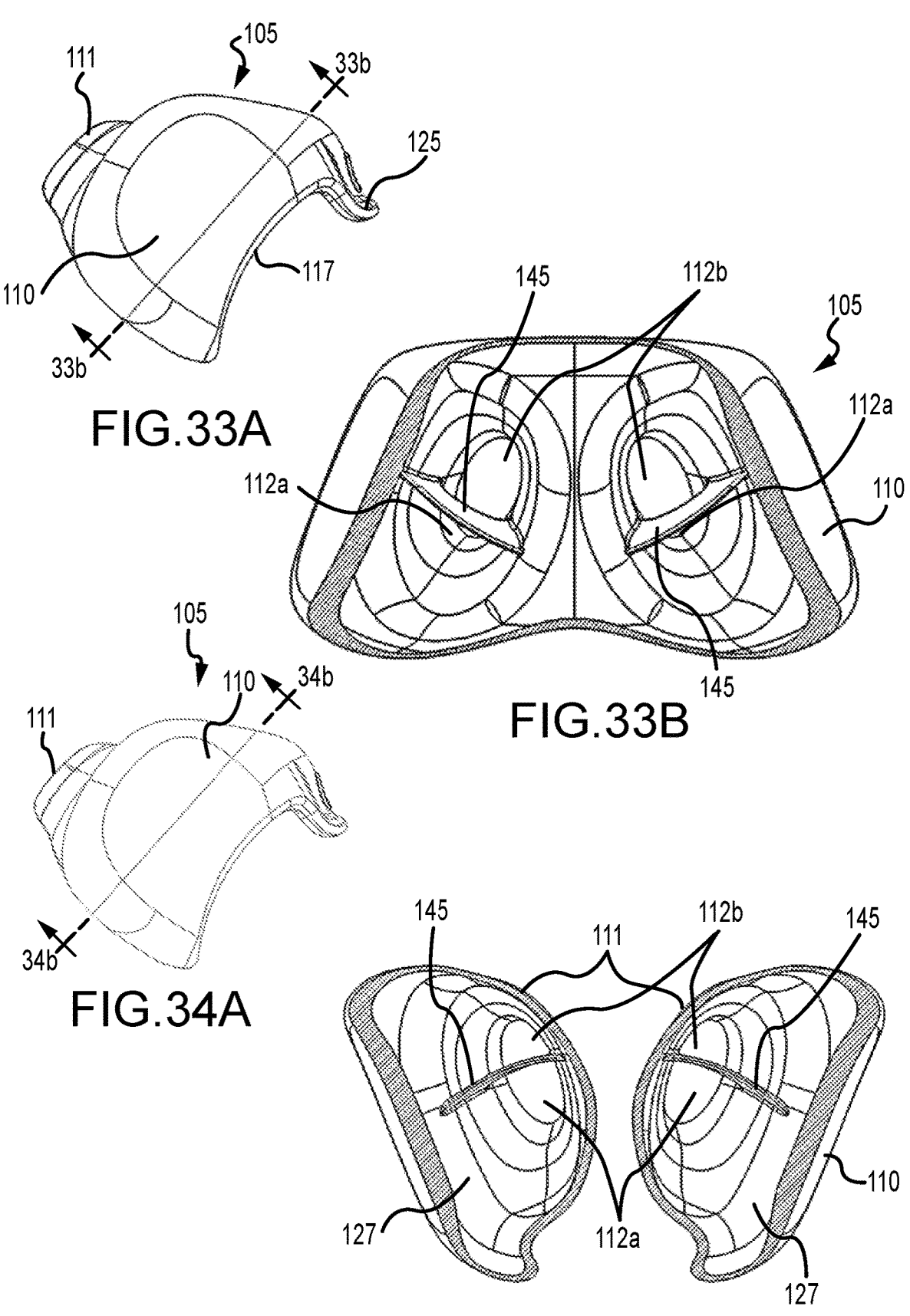
FIG. 33A is a side view of the nasal seal of FIG. 32.
FIG. 33B is a section view of the nasal seal of FIG. 32, taken through line 33b of FIG. 33A.
FIG. 34A is a side view of the nasal seal of FIG. 32.
FIG. 34B is a section view of the nasal seal of FIG. 32, taken through line 34b of FIG. 34A.

Each web 145 is located in the interior cavity 112 of a respective nasal prong 111. As illustrated in FIGS. 33B and 34B, the webs 145 are generally aligned with the minor axis of the respective prong opening, or are spaced from and generally parallel to the minor axis. That is, the webs 145 are substantially perpendicular to the major axis of the respective prong opening. The two prongs are not co-linear and instead angle towards each other.

Each web 145 extends from an interior surface of the wall of the prong 111, extending across the cavity to an opposite point on the interior surface of the prong wall. The edges and corners of the web 145 at the transition to the interior walls of the prong are filleted or rounded to create a more gradual attachment and reduce potential stress concentrations when the web is under tension. This reduces the likelihood of the webs 147 detaching from the respective prong wall, or tearing of the webs themselves.

Figures 35, 36A:
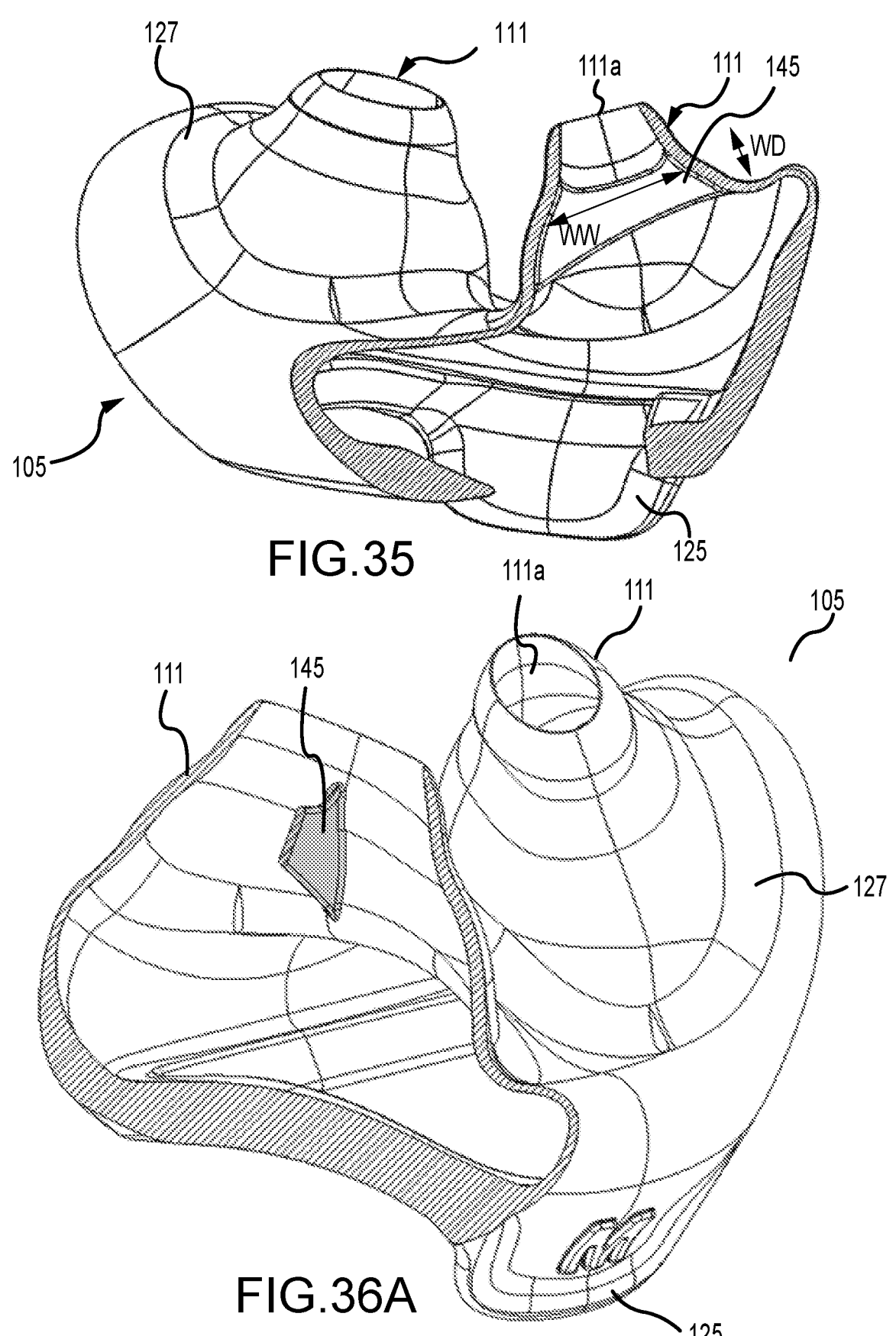
FIG. 35 is a section view of the nasal seal of FIGS. 32 to 34B, the section taken through a plane adjacent and parallel to the nasal prong web.
FIG. 36A is a section view of the nasal seal of FIGS. 32 to 35 the section taken through a plane through and perpendicular to the nasal prong web.

As illustrated in FIGS. 35 and 36A, in the embodiment shown, each web 145 has a bottom edge proximal to the base of the prong 111. The web does not extend fully to the tip of the prong 111, and instead the web has a depth WD between the lower edge and an upper edge that is shorter than the prong depth such that the upper edge of each web 145 is positioned within the prong cavity, spaced from the tip of the prong 111*a*. In one embodiment, the prongs each have an average height of about 10.1 mm, and the respective webs have an average height of about 3.2 mm, with a distance between the upper edge of the prong and the upper edge of the web being about 4.3 mm. That is, the web has a height of about 0.3 times the height of the prong. In alternative embodiments, the height of the web relative to the prong may be different, for example, 0.2 to 0.6 times the height of the web, or 0.25 to 0.4 times the height of the web.

Termination of the web 145 before the tip 111*a* of the prong 111 advantageously ensures that the web doesn't unduly increase the stiffness at the tip of the prong. Therefore, when the tip of the prong 111 contacts the nares of a user during use, it is still able to conform to the contours of the nares. The web 145 doesn't increase discomfort by creating hard or stiff regions that transfer load to the patient's nares.

The webs 145 each have a thickness selected to provide adequate structure to the prong while minimising discomfort to the wearer. Preferably the presence of the web 145 should not be detectable by the user. In the embodiment shown, the webs 145 each have a thickness of about 0.5 mm. However, in alternative embodiments the web thickness may be less than or greater than 0.5 mm, for example between about 0.4 mm and about 0.6 mm, or between about 0.3 mm and about 0.8 mm Referring to the cut-away view of FIG. 35, each web 145 has a width WW that is slightly larger than the linear distance between the two opposing interior surfaces of the prong interior walls of the prong in the minor axis or plane. That is, the web doesn't extend linearly between the two surfaces, it instead has a slight curvature. This curvature enables the prongs 111 to be compressible in both the minor and major directions. Compression in the major direction leads to the stretching and straightening of the web across its width, flattening and tensioning the web 147. Compression in the minor direction causes an increase in the curvature of the web 147. Because the web 147 is already slightly curved in the initial state, this ensures further curvature/buckling of the web is predictable and controlled rather than resulting in ripples or irregularities along the web.

The web width WW and the length of the upper edge are not necessarily the same measurement. The web width is generally measured at a point along the web between the lower edge and upper edge. The upper edge may therefore be shorter than the web width due to the taper of the prong, but alternatively the upper edge of the web may be curved or shaped making it longer than the web width WW.

In alternative embodiments the nasal prong webs 147 may be otherwise oriented, for example they may extend along a direction that is not parallel with the minor axis. For example, the web may generally be provided along the major axis, or at an angle between the minor axis and the major axis. However, the web should always extend across the prong cavity, attached to surfaces on opposing sides of the cavity. A web oriented generally parallel to the minor axis advantageously improves ease of manufacturing and tooling, as the nasal seal 105 can be moulded using a single 2-piece mould core.

In alternative embodiments, each web 145 may extend fully to the tip 111*a* of the prong. However, although a web located at the tip of the prong may provide additional structure, it would not necessary prevent inversion of the prong. Further, the inverted prong may be prone to remaining in the inverted position since in embodiments having a web located at the prong tip have stability both in the original and inverted positions.

FIGS. 36B to 36E illustrate an alternative embodiment nasal seal 805 in which each nasal prong 811 comprises a web 845 according to an alternative embodiment. Unless described otherwise, the seal 805 is substantially as described in relation to the nasal seal 105 of FIGS. 32 to 36A, with like numbers used to indicate like parts, but with the addition of 700.

In this embodiment, the nasal seal web 845 is shaped to have a central portion and two side portions 846. The web 845 has a bottom edge proximal to the base of the prong 811. In the central portion, the web 845 has a depth that is shorter than the prong depth such that the upper edge of the central portion of the web 845 is positioned within the prong cavity, spaced from the tip of the prong 811*a*. The height of the web in the central portion is substantially the same as the height of the web in the previous embodiment seal 105.

The side portions 846 of the web extend along and adjoin the interior surface of the prong wall, towards the tip 811*a* of the prong 811. In the embodiment shown, the side portions extend fully to the tip of the prong, however in alternative embodiments the side portions may terminate before the prong tip. The width of the side portions tapers along the length of each side portion, narrowing towards the tip 811*a* of the prong, such that a distance x between the inner edges of the two side portions is greater at or adjacent a tip 811*a* of the prong 811, than a distance y between the two inner edges of the side portions at the base of the side portions, at or adjacent the upper edge of the central portion.

The web comprises an upper edge. The upper edge has a central portion forming the upper edge of the central web portion, and side portions forming the inner edges of the web side portions. The upper edge may comprise one or more curved portions to create a smooth transition between the upper edge central portion and the upper edge side portions, and/or to create a smooth transition between the upper edge side portions and the inner surface of the prong wall. In the embodiment shown, the transitions between upper edge central portion and the upper edge side portions, and the transitions between the upper edge side portions and the nasal prong wall comprises fillets.

In the embodiment shown, a first one of the upper edge side portions is longer than the other upper edge side portion, and the second side portion is longer than the central portion of the web upper edge.

In the embodiment shown the first upper edge side portion the length is between about 3.8 mm and about 4.7 mm, whereas the second upper edge side portion is between about 3.3 mm and about 4.4 mm. However in alternative embodiments the side portions may have other lengths, or may be the same length. The central portion of the upper edge is about 3.3 mm but alternatively may be between about 2.3 mm and about 3.8 mm, or any other suitable dimension.

Termination of the central portion of the web 845 before the tip 811*a* of the prong 811 advantageously ensures that the web doesn't unduly increase the stiffness at the tip of the prong, while the tapered side portions eliminate undercuts to provide for ease of moulding. In the embodiment shown, the side portions have a taper of about 5 degrees for ease of tool removal and reduction of tool wear. However, in alternative embodiments the taper may be less than or greater than 5 degrees, for example between about 1 degree and about 35 degrees.

Figure 36B:
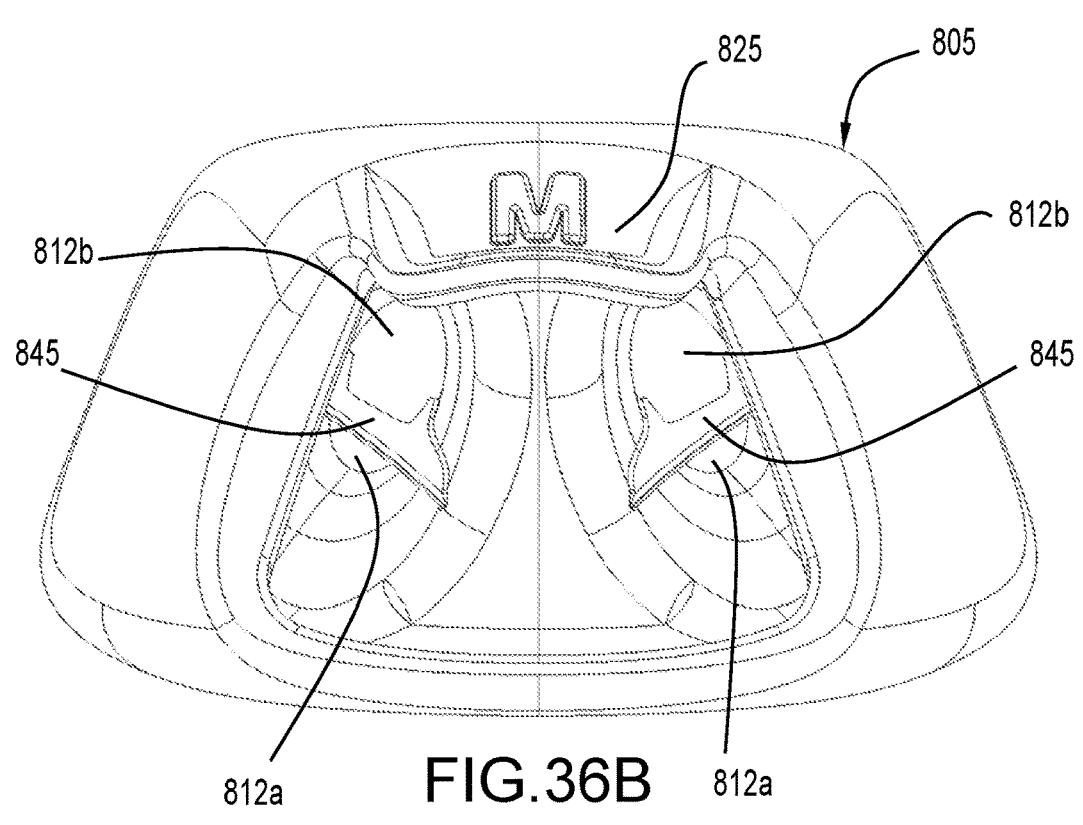
FIG. 36B is a front perspective view of a further embodiment nasal seal having alternative form nasal prong webs, in which the webs are shaped for ease of manufacture.
Figure 36C:
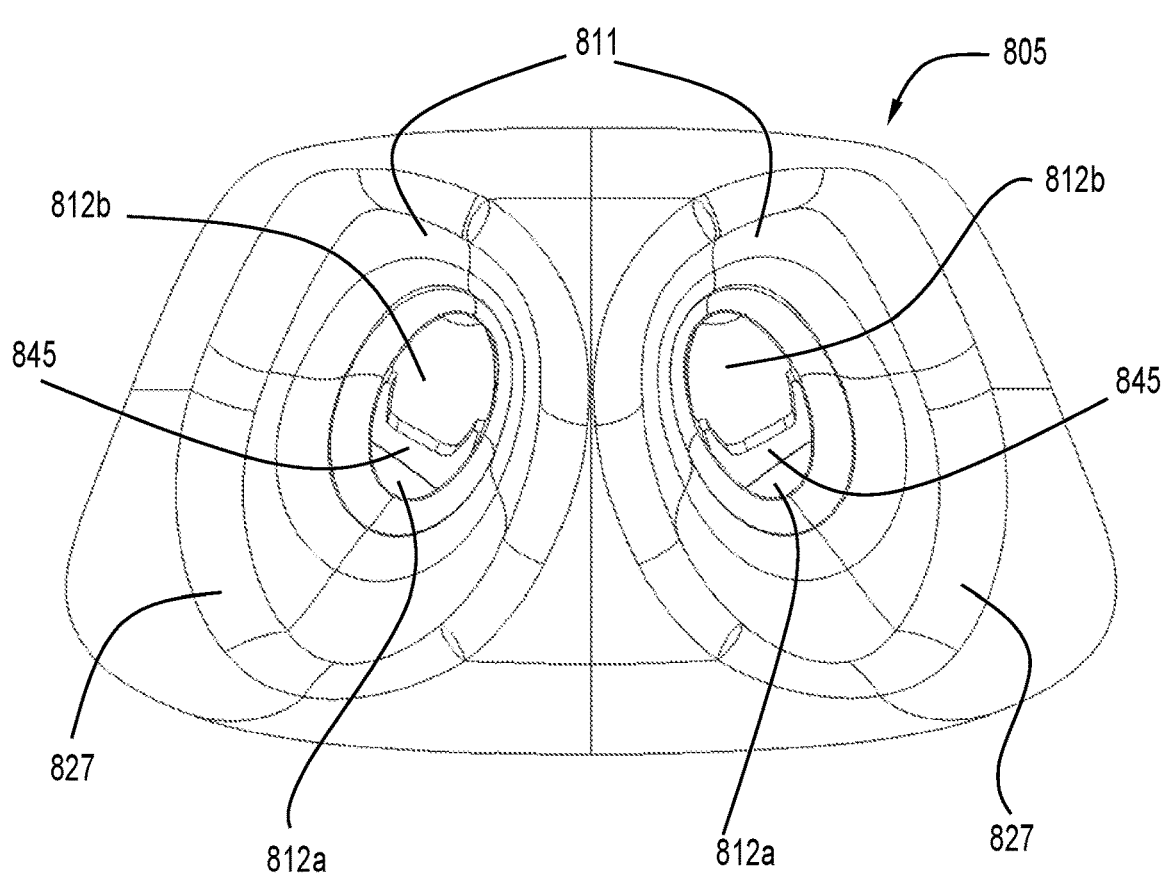
FIG. 36C is a rear view of the nasal seal of FIG. 36B.
Figure 36D:
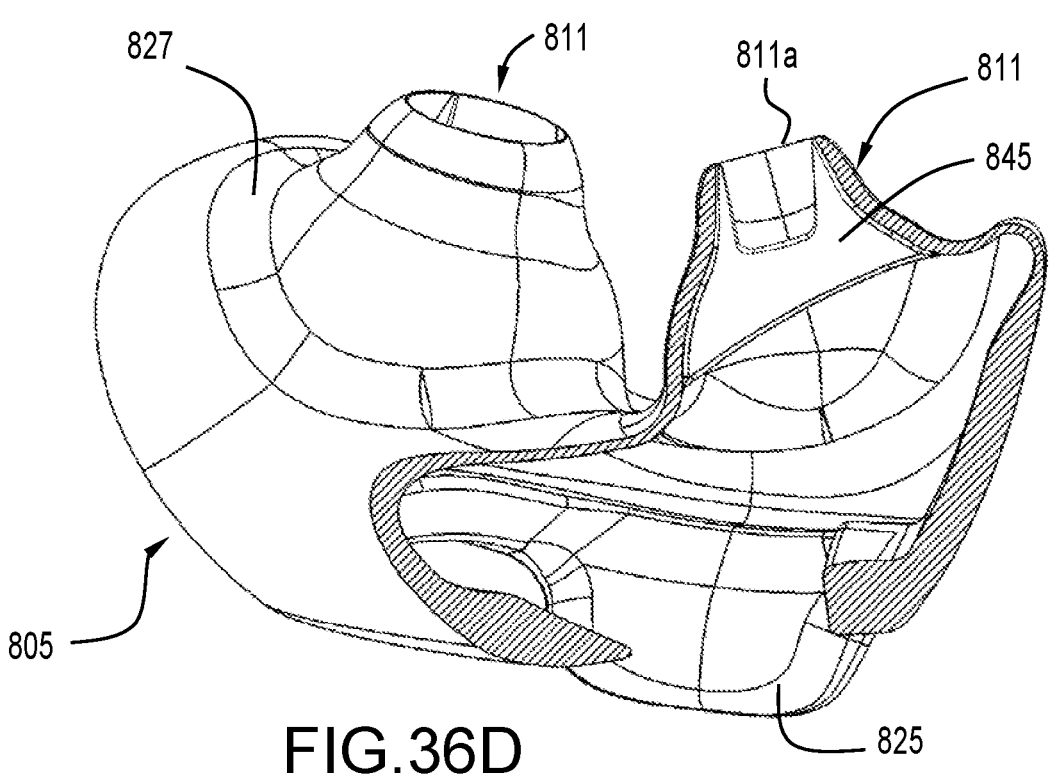
FIG. 36D is a section view of the nasal seal of FIGS. 36B and 36, taken through a plane adjacent and substantially parallel to the nasal prong web.
Figure 36E:
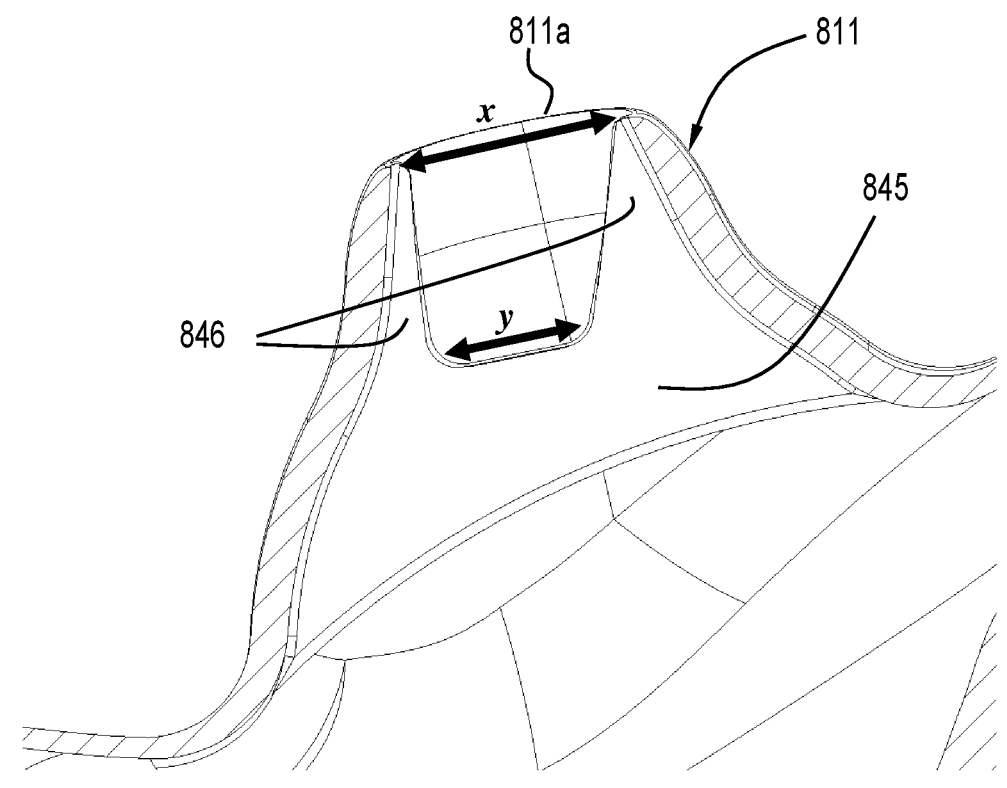
FIG. 36E is a detail view of the section through the nasal prong of FIG. 36D.
Figure 36F:
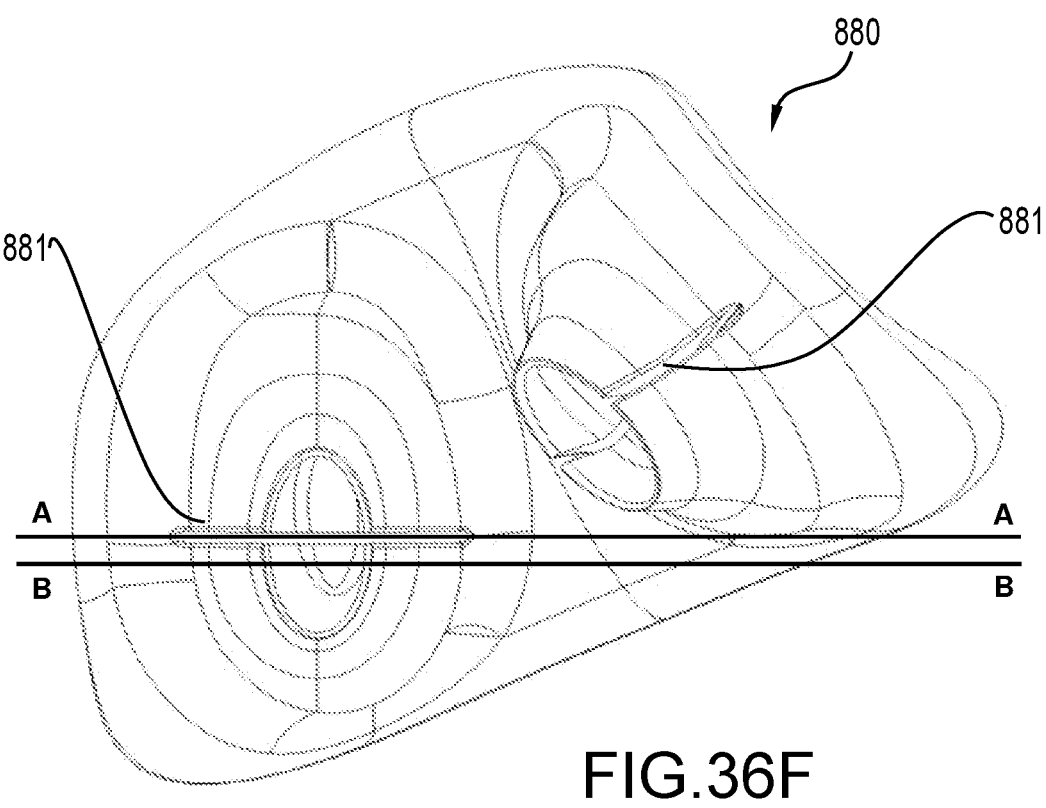
FIG. 36F is a perspective view of a mould core for manufacturing the nasal seal of FIGS. 36B to 36E.
Figure 36G:
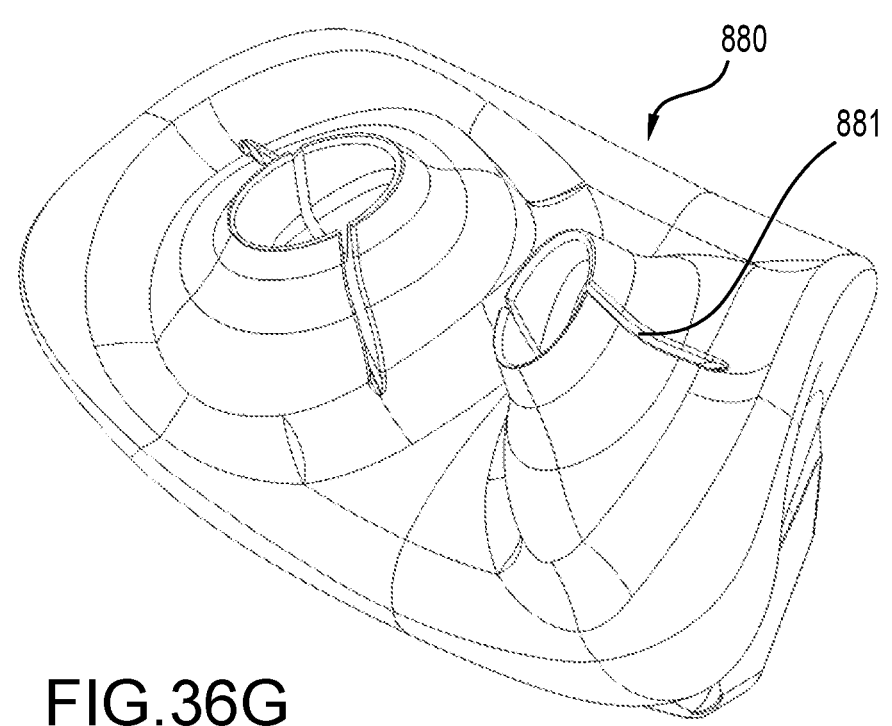
FIG. 36G is a perspective view of the mould core of FIG. 36F.
Figure 36H:
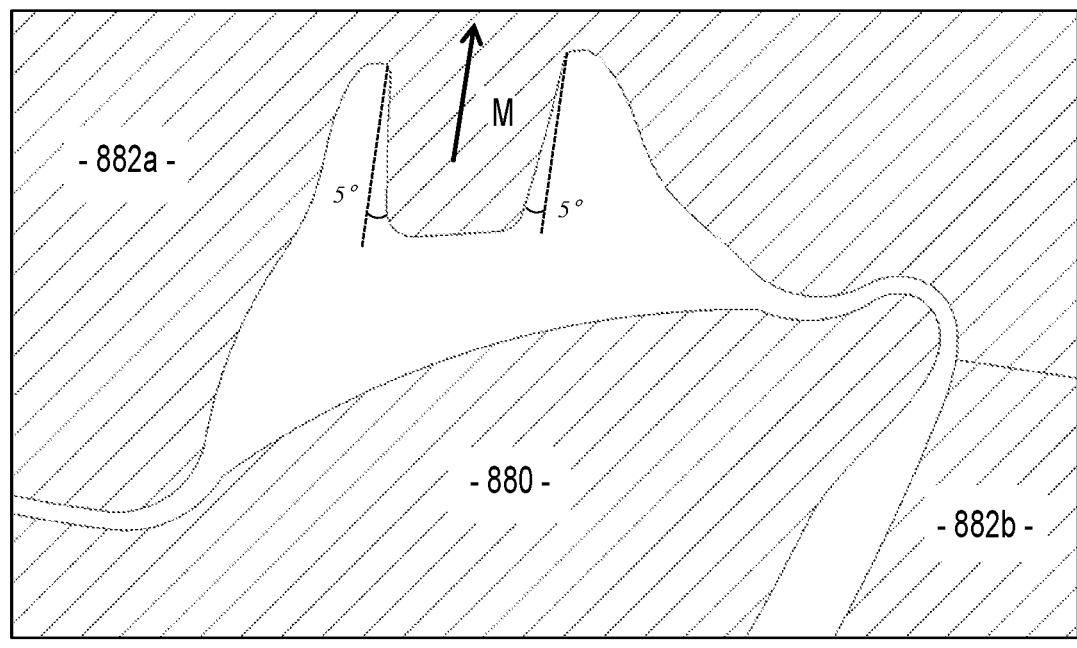
FIG. 36H is a section view of the assembled tooling for manufacturing the nasal seal of FIGS. 36B to 36E, taken through plane A-A in FIG. 36F.
Figure 36I:
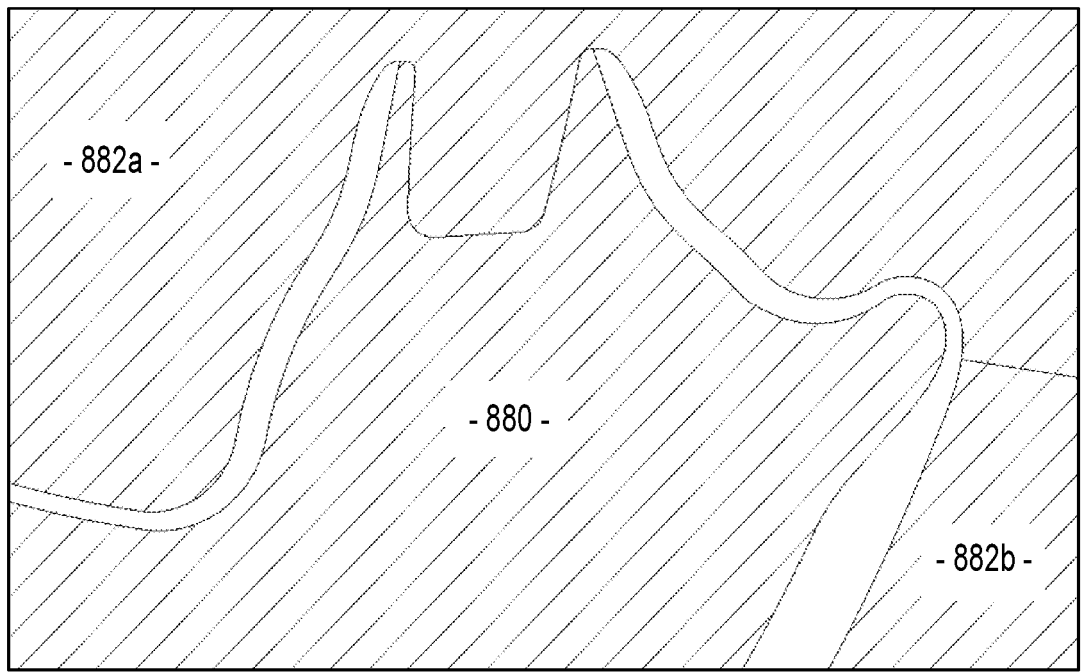
FIG. 36I is a section view of the assembled tooling for manufacturing the nasal seal of FIGS. 36B to 36E, taken through plane B-B in FIG. 36F.

FIGS. 36F to 36I illustrate moulding components to form the nasal seal 805 of FIGS. 36B to 36E. As illustrated in FIGS. 36H and 36I, the web 845 can be formed using an upper mould cavity component 882*a* together with the mould core 880 of FIGS. 36F and 36G and a lower mould cavity component 882*b*. The upper mould cavity component 882*a* comprises a tapered protrusion that protrudes into the prong cavity from the tip of the prong, with the end of the protrusion defining the upper edge of the central portion of the web 845. This enables the prong to be manufactured using a single piece core 880. The taper on the protrusion enables ready removal of the upper mould component 882*a* after moulding.

The webs 145, 845 in the embodiments illustrated are substantially flat, thin members. However, in alternative embodiments, the web may have an alternative form, for example a linkage, bar, rib, or membrane linking opposing walls.

Figures 7, 8:
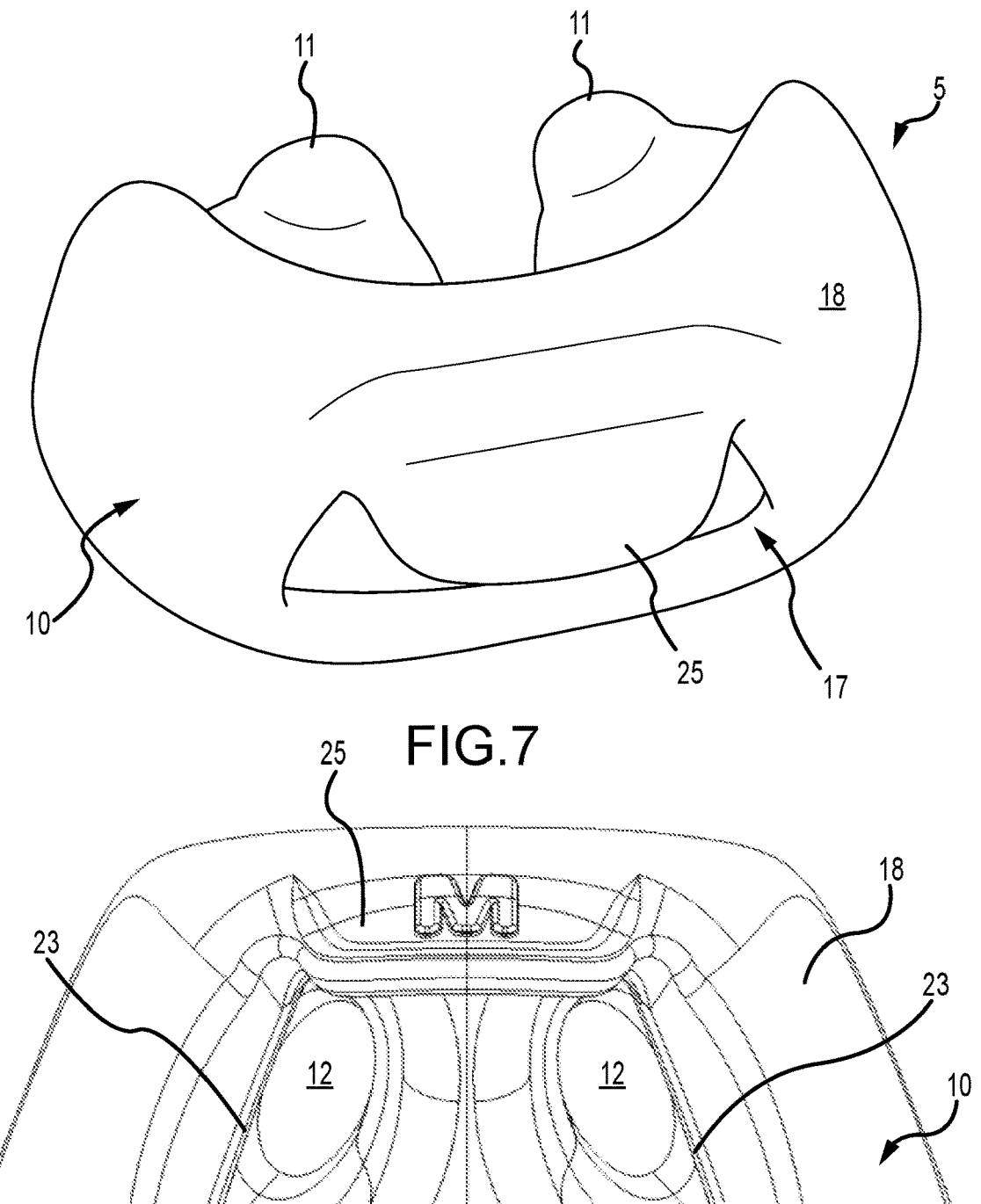
FIG. 7 is a top front perspective view of the nasal seal of FIGS. 1 to 6.
FIG. 8 is a wireframe front elevation view of the nasal seal of FIG. 7.

Referring now back to the first embodiment and to FIG. 8, the nasal seal 5 defines a fluid inlet 17. The fluid inlet 17 is a substantially D-shaped opening, being widest at a base 21 of the opening and narrowest at the top 22 of the opening. This opening shape accommodates the orientation and positioning of the nasal prongs 11, ensuring direct fluid flow through the prong cavities 12. For example, the outer edges of the nasal prong cavities 12 are further apart at the base of the nasal seal 5 than at the top. As shown in FIG. 8, in a front view, the openings of the nasal prong cavity 12 at the tips

11*a* of the nasal prongs are substantially within (rear of) the perimeter of the D-shaped inlet 17, thereby allowing a direct fluid flow from the inlet 17 through the nasal prong opening.

In the embodiment shown, both the top and bottom edges 21, 22 of the inlet 17 are curved in a concave manner (the top edge 22 is obscured in FIG. 8 by the pull tab 25), with angled sides 23 angled extending from the respective ends of the top and bottom edges 21, 22. The inlet sides 23 are substantially linear in a rear or front view.

The corners of the opening 17 where the sides 23 meet the respective top and bottom edges 21, 22, are rounded to avoid stress concentrations. The rounding also allows for some misalignment between the frame and the seal opening 17 to prevent sealing performance being adversely affected by a small misalignment. In the exemplary embodiment, the width of the top of the opening 22 is approximately 15 mm, and the width of the bottom of the opening 17 is approximately 27 mm, with a maximum distance between the top of the opening and the bottom of the opening of approximately 22 mm.

It will be appreciated that these dimensions may change depending on the size or geometry of the nasal seal, and/or the frame geometry.

The side edges 23 of the nasal seal inlet 17 are arcuate in side profile. As illustrated in FIG. 10, the arc is concave relative to a front of the seal 5 with a constant radius ri of about 25 mm and centre of curvature 24 forward of the seal 5.

Figure 11:
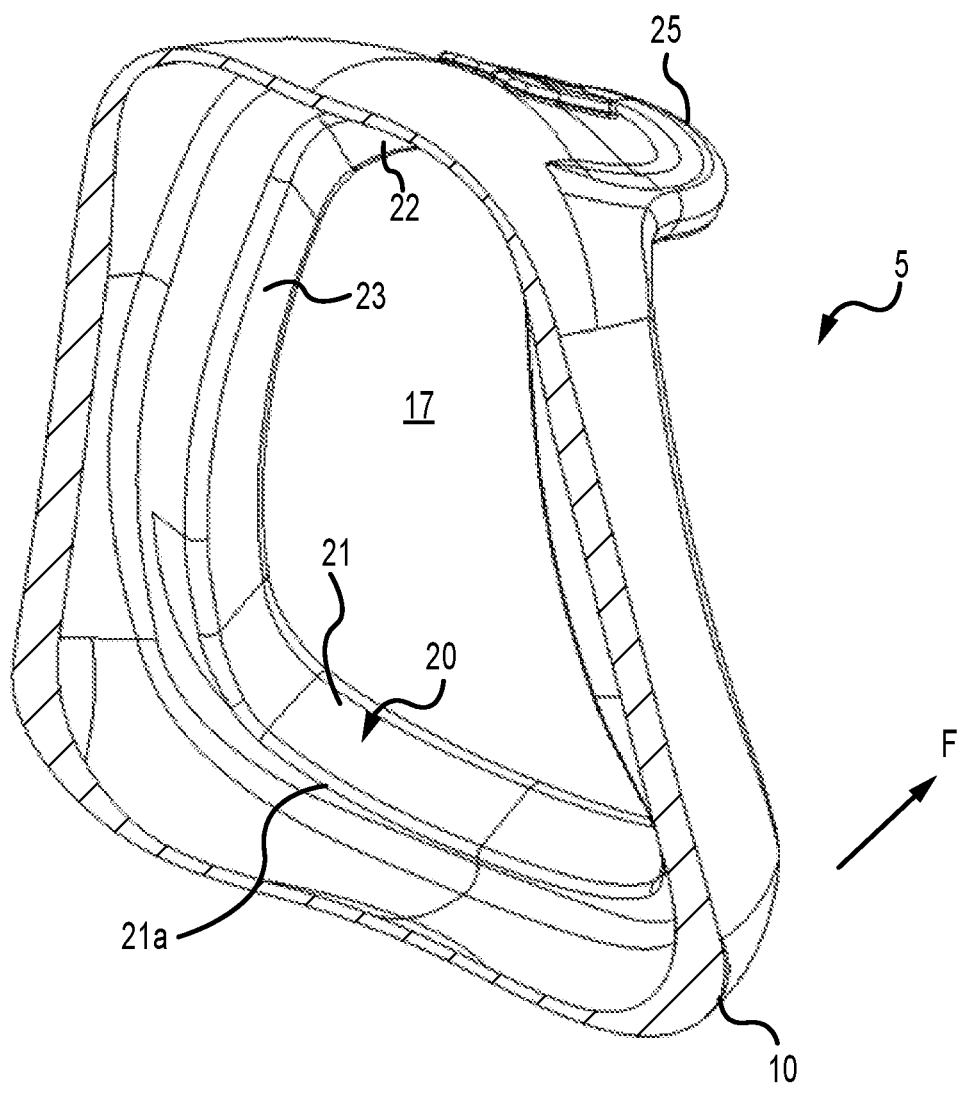
FIG. 11 is a perspective section view of the nasal seal of FIGS. 7 to 10, taken through a vertical plain through the main body of the seal, showing an interior view of the fluid inlet and attachment lip.
Figure 12:
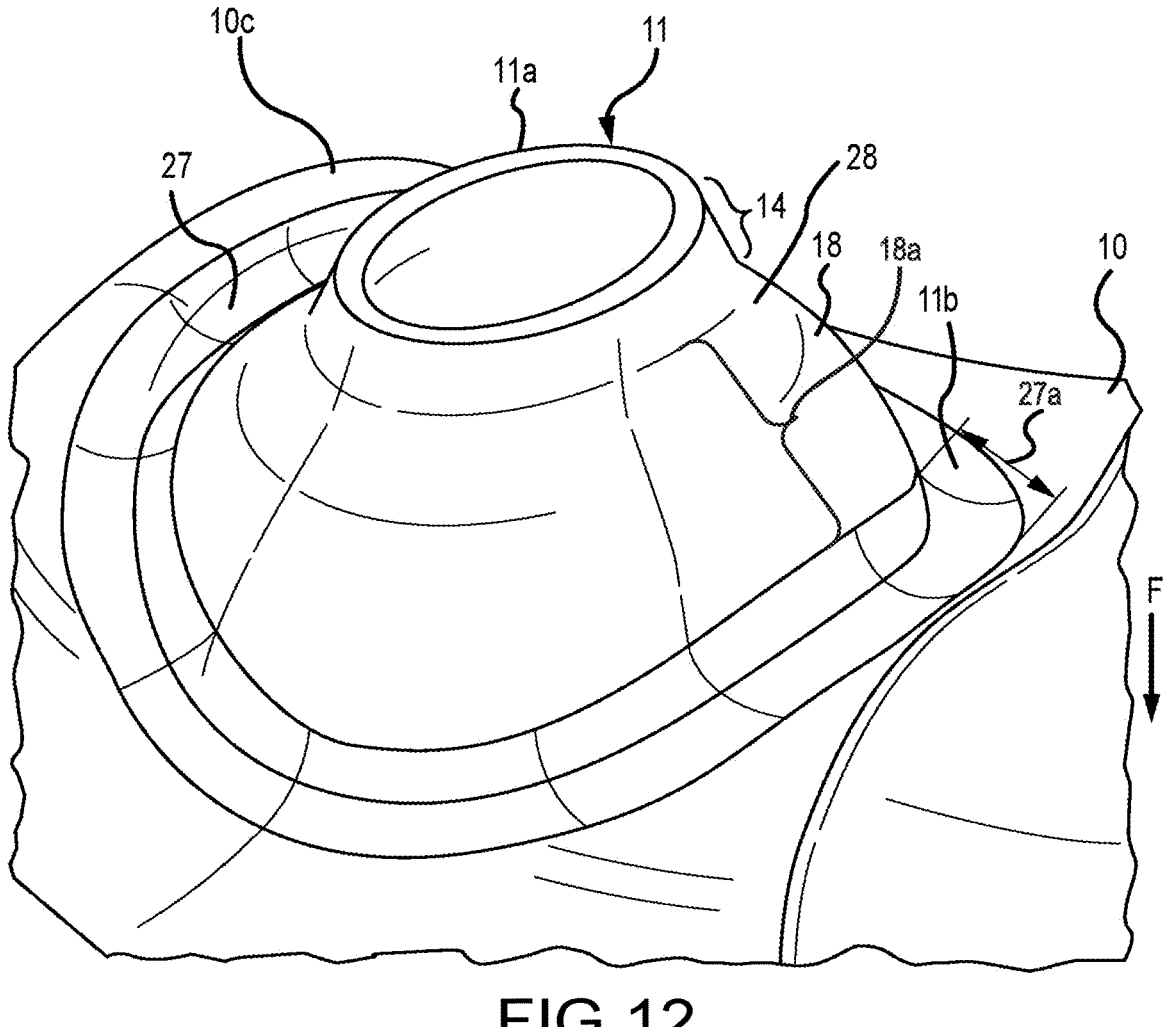
FIG. 12 is a perspective detail view of one of the nasal prongs of the nasal seal of FIGS. 7 to 10.

As illustrated in the cut-away view of FIG. 11, an inwardly extending lip 20 is provided at the fluid inlet opening 17 for engaging a support frame 3. The lip 20 is a region of increased wall thickness around the periphery of the inlet 17, defining the edges 21, 22, 23 of the inlet 17. This lip 20 facilitates engagement with a frame by deforming the seal around a portion of the frame, which will be described in more detail below. In the embodiment shown, the lip 20 has a depth of about 3 mm, however this may vary between embodiments.

A pull tab 25 is provided at a top of the nasal seal 5, projecting rearwards adjacent the fluid inlet 5. The pull tab 25 provides an intuitive gripping surface for a user, and may include a thickened front edge or ribbed or otherwise textured surface, to provide more grip to the user when pulling the seal onto the frame 3, as will be described in more detail below.

FIGS. 15 to 24 illustrate the frame 3 to which the nasal seal 5 described above connects. The frame 3 defines a fluid chamber 4 having an inlet 15, and an outlet 16 for fluid communication with the inlet 17 of a nasal seal. The frame includes a collar at the inlet 15, for coupling to a fluid conduit 9. The inlet 15 may include a tube retaining recesses to enable the end of a conduit 9 to rotatably attach to it, for example, using a snap-fit mechanism such that the conduit 9 can swivel freely relative to the frame 3. In the embodiment shown, the frame inlet 15 has a diameter of approximately 15 mm for compatibility with existing fluid conduits, however, other inlet sizes are envisaged.

The exterior surface of the frame adjacent the frame outlet 16 forms a substantially D-shaped seal retaining rim that complements the D-shaped opening of the nasal seal fluid inlet 18. The seal retaining rim comprises an upper surface, a lower surface, and two opposite side surfaces extending between the upper and bottom surfaces. Outwardly protruding flanges 29, 31 are provided along rear edges of the upper and lower surfaces of the seal retaining rim, adjacent the outlet 16, extending along substantially the whole of the upper or lower surface. The upper flange 29 is narrower in width than the lower flange 31 in accordance with the wider lower edge of the D-shaped opening.

The fluid inlet 17 on the nasal seal 5 is configured to be received over the seal retaining rim at the frame outlet 16. The bottom flange 31 on the frame is engaged with the nasal seal at the fluid inlet 17 by placing the lower flange 31 through the inlet 17 and 'hooking' the flange 31 behind the lower lip 21*a* on the nasal seal 5. Such that a front surface of the lower flange 31 abuts a rear surface of the lip 20 at the bottom of the seal inlet 17. The flange 31 protrudes a distance that substantially corresponds to the depth of the lip 22, such that a major part of the lower lip abuts the lower flange 31. In the embodiment shown, both the top and bottom flanges 29, 31 protrude about 1 mm (see FIG. 26). The top and bottom protrusions 29, 31 have rounded edges to aid their insertion into the seal inlet 17, but also to avoid inadvertent damage to the seal which may occur during assembly and disassembly if sharp edges were used.

The long engagement surface provided by the lower flange 31 makes insertion of the lower flange into the seal inlet 17 achievable for a range of users, including those with impaired fine motor skills, or impaired vision. In addition, the long lower flange aligns the seal 5 with the frame 3 for the second stage of assembly.

In a next step, once the lower flange 31 is engaged with the lip 20, the user grips the pull tab 25. Using the pull tab 25, the user pulls the nasal seal 5 upwards, moving the fluid inlet 17 over the frame outlet and over the top flange 29. The top flange positively engages the nasal seal 5 by 'hooking' behind the upper lip 22. Such that a front surface of the upper flange 29 abuts a rear surface of the lip 20 at the top of the seal inlet 17. The flange 29 protrudes a distance that substantially corresponds to the depth of the lip 22 at its top portion, such that a major part of the top lip abuts the top flange 29.

Figures 3, 4:
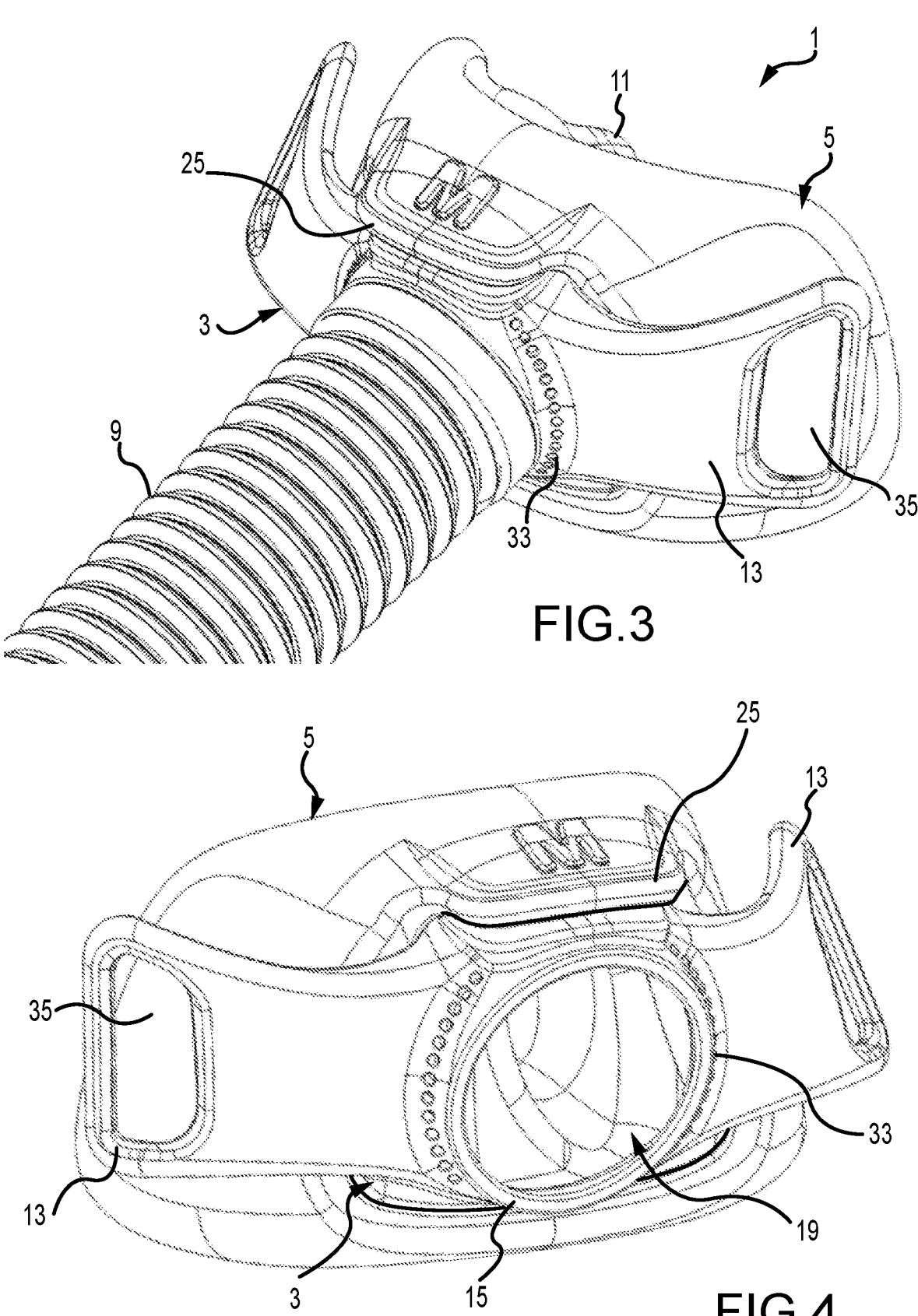
FIG. 3 is a front perspective view of the assembled respiratory interface of FIG. 2.
FIG. 4 is a front side perspective view of the mask of FIGS. 2 and 3, with the supply conduit removed.
Figures 5, 6:
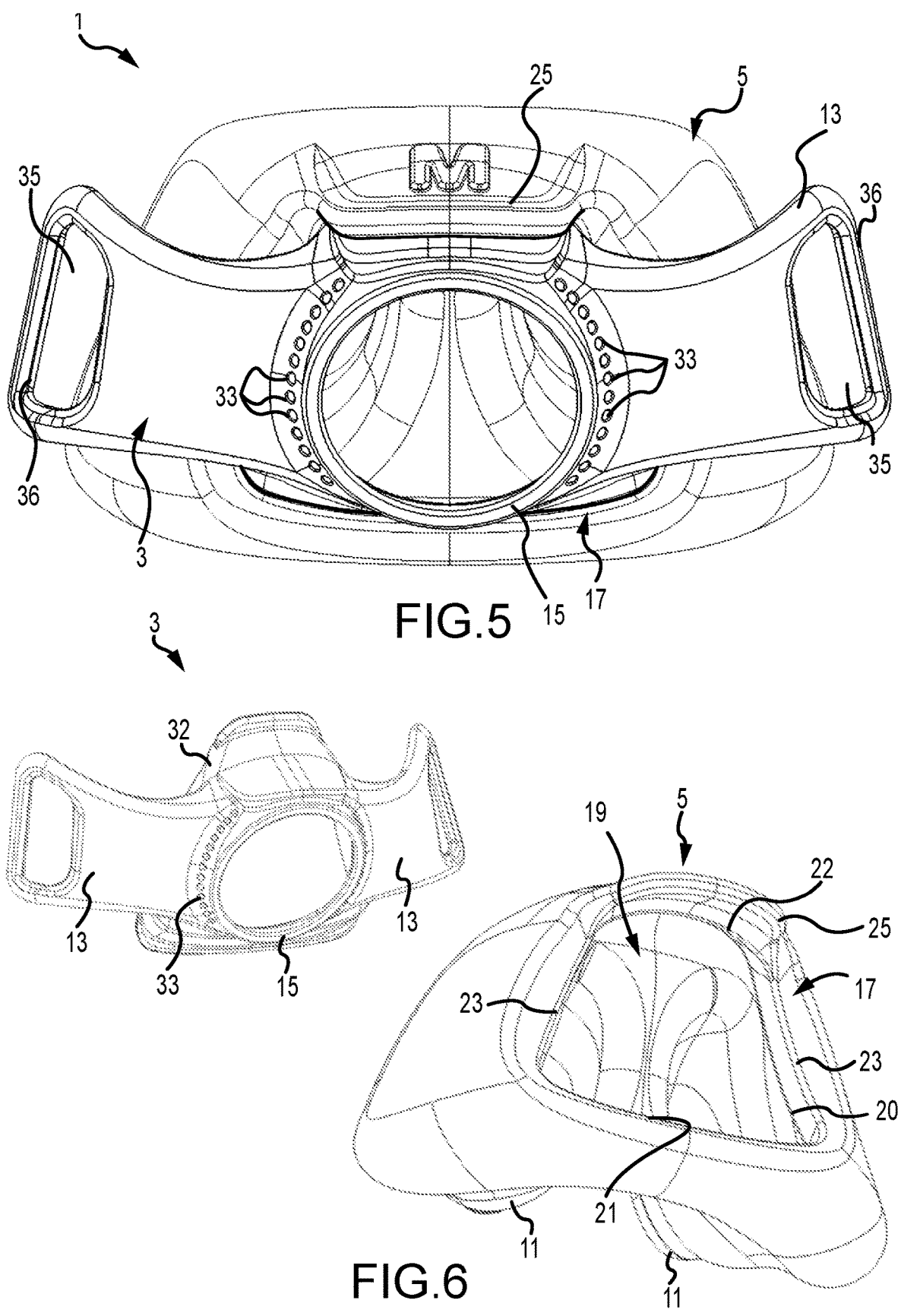
FIG. 5 is a wireframe front elevation view corresponding to FIG. 4.
FIG. 6 is an exploded front perspective view, showing the nasal seal disconnected from the frame.

The frame 3 has a pull-tab alignment surface 26 that is aligned directly under the pull-tab 25 when the mask 1 is assembled. The pull-tab alignment surface 26 acts as a visual cue for a user to assist with correct assembly and alignment of the seal 5. The pull-tab 25 will be positioned directly over the pull-tab alignment surface 26, when the D-shaped opening of the seal is aligned with the D-shaped rim of the frame and the upper and lower flanges 29, 31 are engaged with the respective portions of the lip 20 on the nasal seal 5. The 'D' shape of the connection assists with alignment between the nasal seal 5 and the mask frame 3, to prevent incorrect assembly, and improve ease of use As illustrated in FIGS. 3 and 5, the pull tab 25 does not rest on the pull tab alignment surface 26 when the mask is assembled, rather there is a gap between the alignment surface 26 and the lower surface of the pull tab 25. This gap allows a user to place their finger under the pull tab 25 to readily grab the pull tab 25 to pull the seal up and rearwards over the top flange 29 to remove the nasal seal 5 from the frame 3. In addition, the pull tab 25 may have additional visual features to enhance its visibility. In the embodiment shown, the pull tab 25 includes a large 'M' marking to indicate the mask size but other visual features or tactile features for improved grip are envisaged. The pull tab also helps by identifying the top of the mask, thereby making fit of the mask more intuitive and reducing the occurrence of users incorrectly fitting the mask upside down.

Figures 25, 26:
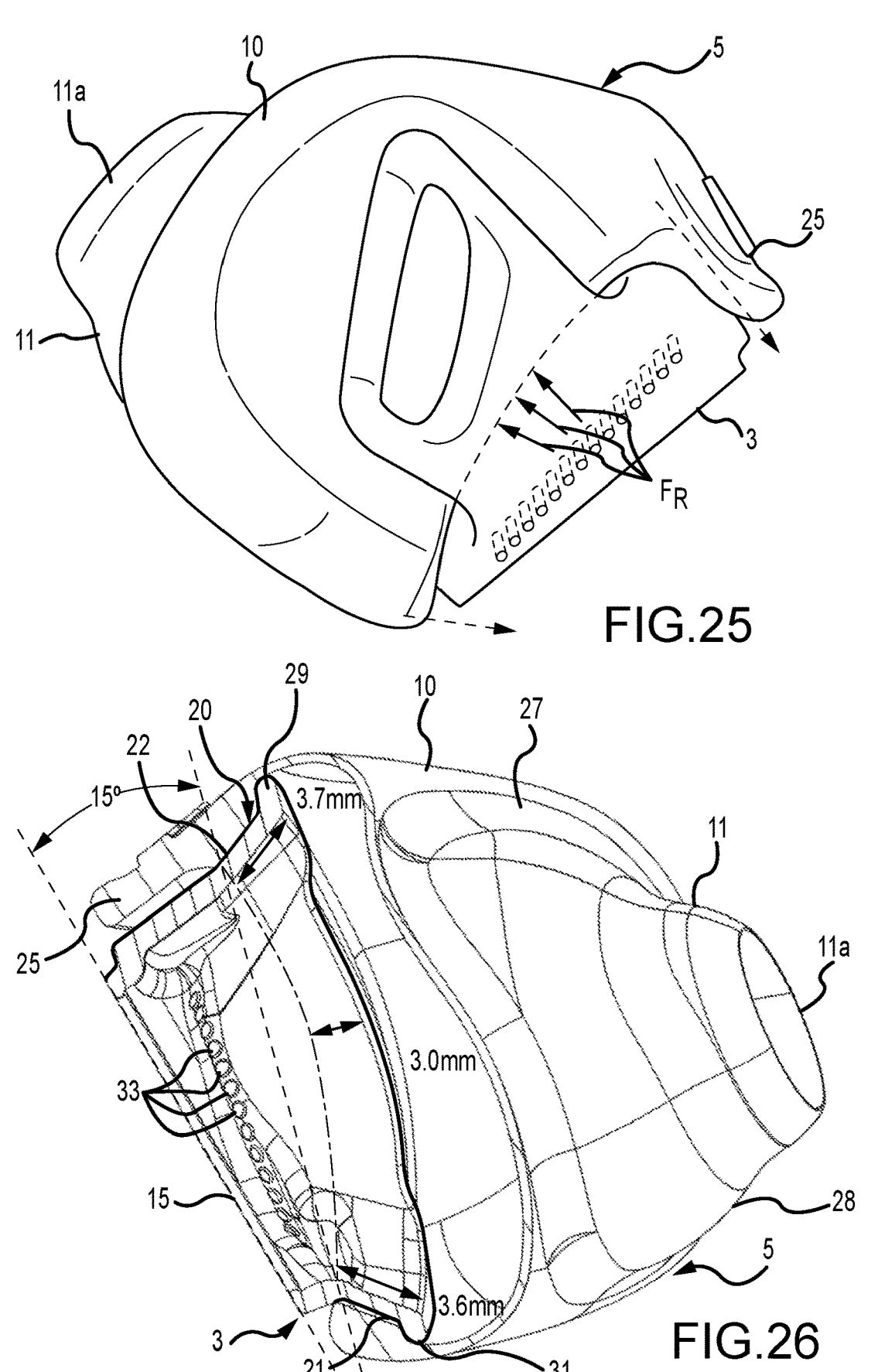
FIG. 25 is a side view showing the assembly of the frame and nasal seal, and illustrating the connecting forces.
FIG. 26 is a side cut away view showing the engagement of the nasal seal with the frame.

When the nasal seal 5 is assembled with the frame 5, the sides of the lip 20 on the nasal seal 5 abut corresponding sides of the seal retaining rim on the frame 3. The engagement between the sides 23 of the lip 20 and the sides of the seal retaining rim is illustrated in FIG. 26.

In the illustrated embodiment, the opening 17 on the nasal seal 5 is slightly smaller in a resting state than the dimensions of the seal retaining rim of the frame 3 on which it sits. This ensures that the seal 5 is held in tension over the frame 3, to provide a tighter seal with the frame 3. The side lips 23 on the nasal seal opening are thereby held in contact with the sides of the rim 32 at the frame outlet 16.

For example, in the embodiment shown there is about 0.3 mm of overlap/interference-approximately 10% of the thickness of the seal lip (3 mm). In the embodiment shown, the nasal seal 5 comprises a single-durometer silicone material (Momentive Silopren 4840) such that the thicker lip region will produce higher tension forces when attached to the frame than the surrounding thinner walled regions.

The upper and lower flange engagements and the tension in the lip 21, 22, 23 of the seal inlet 17 hold the nasal seal 5 to the frame 3 to prevent the nasal seal 5 from slipping off the frame 5, even at high therapy pressure. Advantageously, no additional components are required to attach the seal 5 to the frame 3. Thereby reducing complexity and the overall cost of components.

Figure 27:
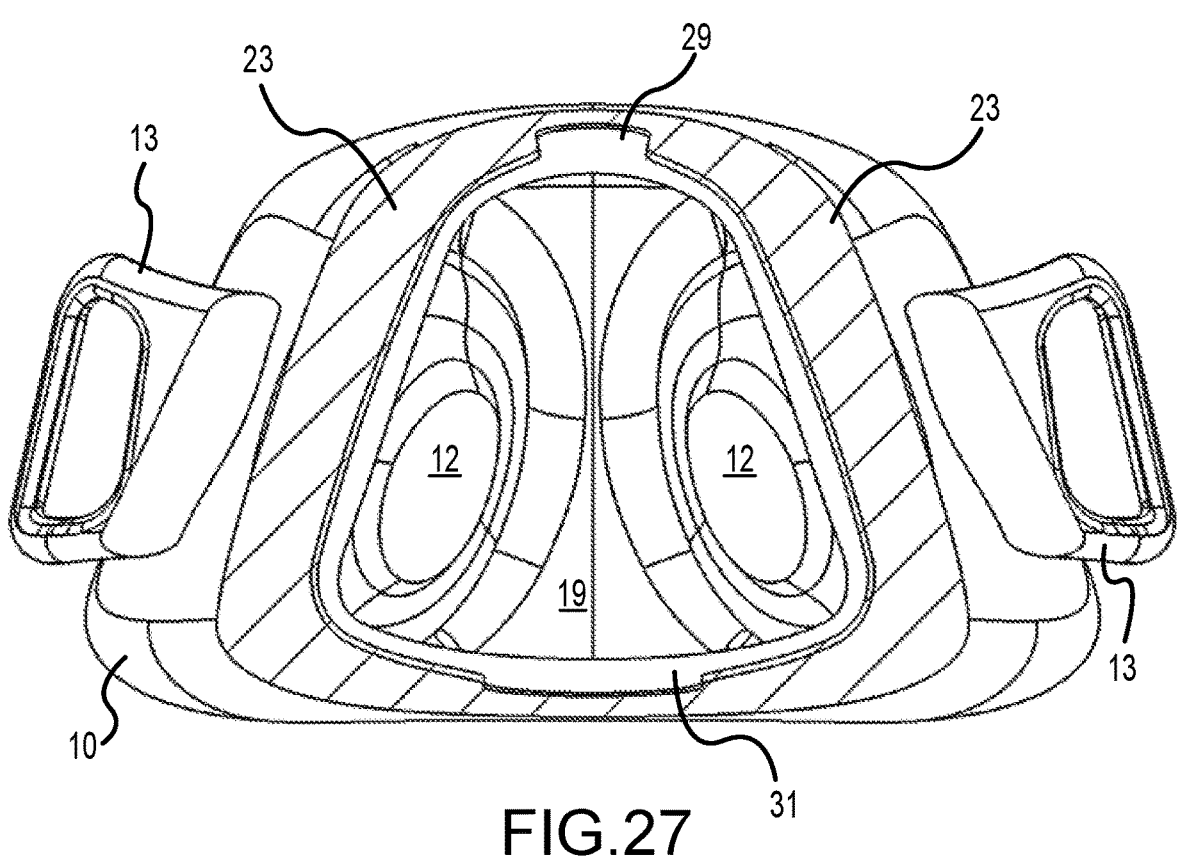
FIG. 27 is a front section view taken through a pane through the attachment lip of the nasal seal, showing the attachment between the seal and the frame.
Figures 29, 30:
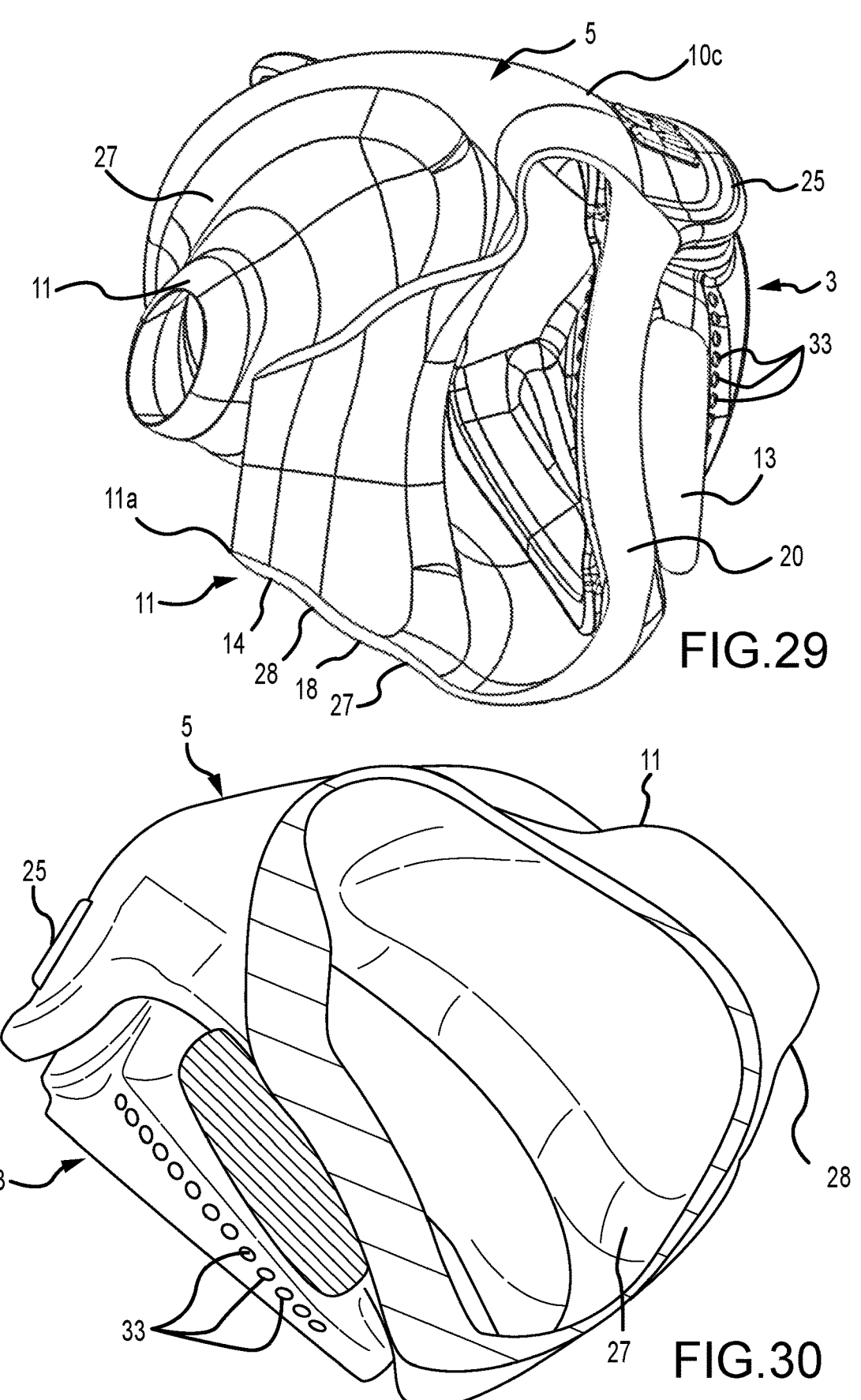
FIG. 29 is a cut away side perspective view showing variations in the wall thickness of the nasal seal.
FIG. 30 is a side section view showing the nasal seal.

As indicated in FIGS. 25 and 27, the tension applied to the top and bottom regions when they are engaged with the respective flanges 29, 31, assists with pulling the side lips 23 inwards into contact with the adjacent frame surface to ensure a good airtight seal between the lip 20 of the nasal seal 5 and the seal retaining rim on the frame 3. However, this results in a force acting on the nasal seal 5 to pull the seal forward into contact with a rear surface of the frame arms 13. As illustrated in FIG. 30, the rear surface of the frame arms 13 where the arms are in contact with the seal 5 is convex with a radius of 25 mm, to complement arcuate side profile of the seal opening 17 described above (see FIG. 25). The frame arms provide a reaction force against the forward pull of the seal, resulting in the creation of reaction forces FR in the side regions of the nasal seal opening 17. The arcuate profile of the seal opening 17 and the complementary shape of the frame arm surfaces evenly distributes forces around the seal opening. Alternatively or additionally, a small rib or bead may be provided along at least a part of the seal retaining rim engaging feature to engage with a complementary recess on the seal, or vice versa.

The nasal seal 5 may be readily removed from the frame by reversing the above described process. That is, gripping the pull tab 25, pulling it up and rearwards to pull the seal out of engagement with and over the top frame flange 29, before removing the lower flange 31 from the fluid inlet 17 and out of engagement with the seal lip 20.

The mask frame 3 features headgear coupling arms 13 that extend laterally from the frame adjacent the sides of the frame inlet 15, and substantially following the contour of the main body of the nasal seal 5 without contacting the body of the nasal seal 5, at least in a resting, non-use state. The resulting gap between the side walls of the seal 5 and the interior surface of the frame arms 13 allows for the movement of the nasal seal 4 when pressed against or into the nose of the wearer. This enhances the cushioning effect of the seal, and reduces the pressure on the nose, especially under higher forces applied by headgear.

The coupling arms 13 have coupling features configured for attaching the frame 3 to head gear. In the embodiment shown, the arms each have an aperture 35 at a distal end of the arm 13, creating a post 36 for receiving a headgear strap 7.

The headgear coupling arms 13 angled relative to the nasal seal and frame such that the reaction force from the headgear 7 is substantially evenly distributed over the attached nasal seal to ensure stability and correct positioning of the nasal seal 5 in use.

In the embodiment shown, the distal ends of the coupling arms 13 are formed to allow the post 36 to be normal to the headgear force and for correct seal positioning. This is achieved through a post angle offset of approximately 11.8° with reference to the vertical axis in the exterior/front view and 10° in the side view. Due to the angle of the frame inlet 15, shown in FIGS. 2, 22A, 22B, these views are not normal to the cross-section of the tube connection feature.

As illustrated in FIG. 2, the axis normal to the headgear connection post 36 has an angle offset of approximately 50° from the most distal surface of the tube connection feature. This angling of the frame 3 and subsequently of the nasal seal 5 directs the seal upwards and into the nares of the user to assist with achieving a correct fit and good seal.

The frame arms 13 are thickest in the portion of the coupling arms 13 adjacent to the frame inlet 15, and reduce in thickness towards the distal ends of the arms 13. In the embodiment shown, the thicknesses decreases from approximately 4 mm to 2 mm towards the free end of the arm.

In the present embodiment, the overall maximum width of the frame including the coupling arms 13, is 57 mm. Preferably the length of the wings 13 does not extend rearward of the nasal seal rear surface when assembled. This contributes to the small and unobtrusive nature of the mask 1.

In addition to the simple two-part assembly described above, the frame 3 and nasal seal 5 are configured to reduce tooling and manufacturing costs. For example, the mask frame 3 may not include undercuts to ensure its suitability for a two-part moulding process, for example, the seal retaining rim on the frame 3 is angled inwards away from the mask headgear retaining arms 13. While a rim angled outwards may achieve a superior seal, this may be avoided as it will create an undercut. In addition, for ease of manufacture, it is preferable that the mask frame 3 also not feature any large thickness changes or sharp corners; all edges and transitions between surfaces are smooth to avoid sinks that may form during the moulding process.

For the nasal seal 5, the orientation of the seal in the mould is ideally chosen to aid removal of the seal 5 from the mould. For example, in the pull-direction of the seal. The pull tab 25 on the nasal seal advantageously aids removal of the seal 5 from the mould. Undercuts are of less concern with the seal as it is made of a flexible, resilient material such as silicone.

The frame 3 comprises a series of bias flow apertures 33 adjacent the inlet 15, forming a diffuser. The bias flow apertures 33 are arranged in two symmetrical arcuate rows, each having 13 apertures, on opposite sides of the inlet 15. The rows are may be concentric with the inlet 15. In alternative embodiments, the rows may contain more or fewer apertures.

In the embodiment shown, the bias flow apertures 33 are substantially cylindrical have a diameter of 0.7 mm, a spacing of 1.2 mm (between centres of adjacent apertures), and adjacent apertures being angularly spaced at an angle of 6.9 degrees. At the surface of the frame, the apertures have rounded or tapered edges provided by a fillet or as a result of manufacturing processes. The apertures 33 are provided at an inflection region defined by a fillet 34 formed between the conduit collar at the frame inlet 15 and a main body of the frame 3 that extends to the headgear connecting arms 13. In particular, the bias flow apertures 33 are situated 1.5 mm from the outer edge of the inflection contour. In the embodiment shown, the bias flow apertures are laser cut into the frame 3.

The axes of the bias flow apertures 33 are perpendicular to the exterior surface of the contour region. Therefore their positioning on the filleted surface 34 means the bias flow apertures 33 are angled to direct airflow rearwards and outwards, away from the surfaces of the mask (as to not impinge on any surface of the frame) and away from each other.

This arrangement produces minimal sound during CPAP therapy while advantageously directing drafts away from a user's face and eyes and diffusing air quickly. The projected axes of the bias flow apertures 33 do not all intersect at a singular point, rather the axis of a given aperture will intersect axes from other bias flow apertures at varying points rear of the aperture.

Figures 37, 38A, 38B:
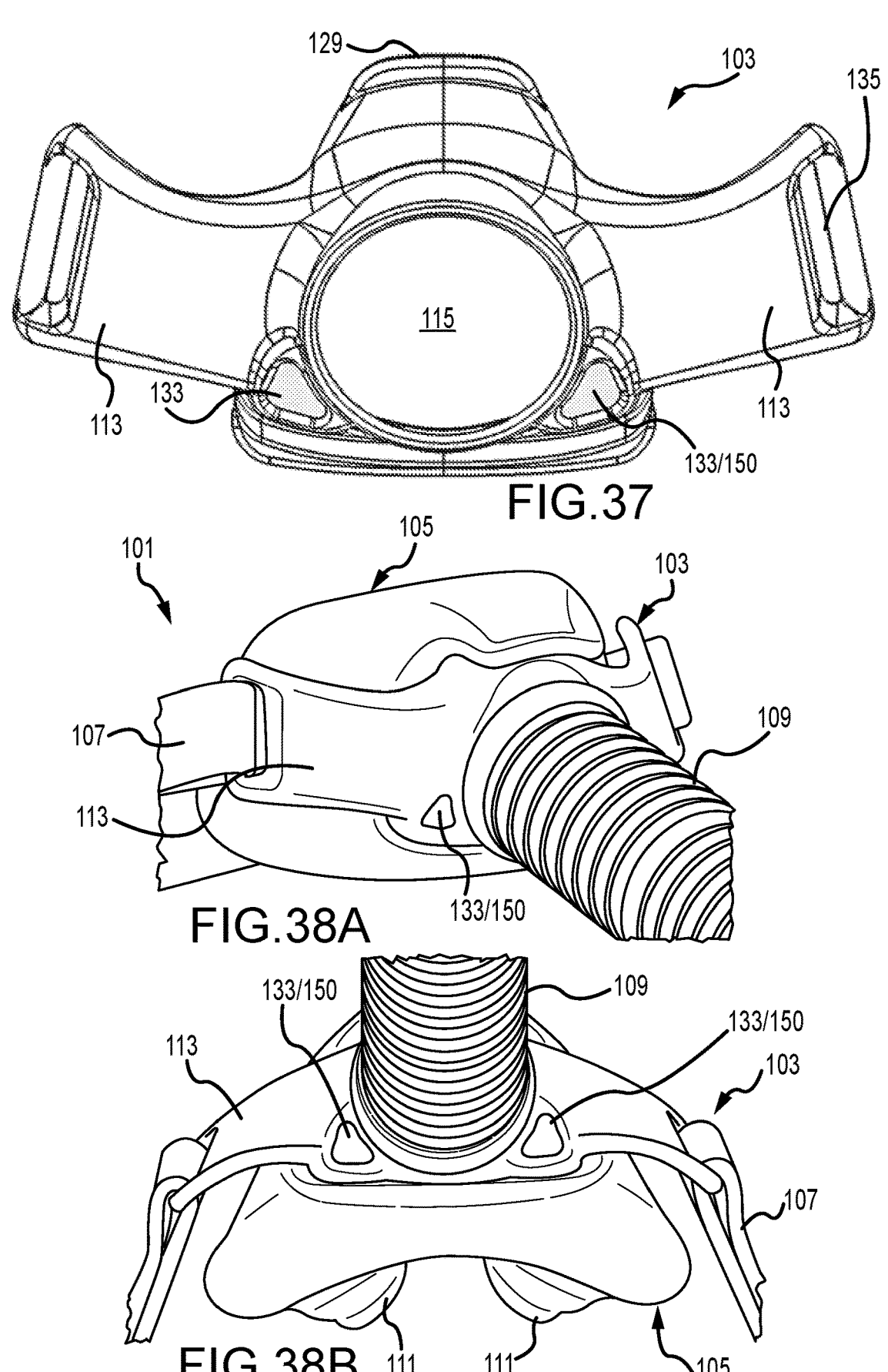
FIG. 37 is a front view of a second embodiment nasal seal support frame having triangle-shaped front diffusion apertures.
FIG. 38A is a front side perspective view showing a respiratory interface including the support frame of FIG. 37 and the nasal seal of FIGS. 32 to 36A.
FIG. 38B is a front underside perspective view of the respiratory interface of FIG. 38A.

In alternative embodiments, in place of or in addition to the bias flow apertures, the respiratory mask may comprise one or more alternative features to diffuse air flow from exhalation and reduce the associated noise. FIG. 37 illustrates an alternative embodiment frame 103 for a respiratory mask 101. Unless described below, the frame 103 is substantially as described in relation to the first embodiment frame 3. Like numbers are used to indicate like parts, but with the addition of 100.

In this embodiment, two diffusion apertures 133 are provided in the mask frame 103, on the left and right sides of the frame inlet 115, proximal a lower part of the inlet. In the embodiment shown, the apertures 133 are substantially triangular to fit the space available in the lower part of the frame 133 between the frame inlet 115 and the outer perimeter of the main body of the frame 103.

The diffusion apertures 133 are in fluid communication with the fluid chamber defined by the frame 103, to allow air exhaled by a user into the chamber flow out through the diffusion apertures 133. The diffusion apertures 133 direct exhaled air in a forward direction F, thereby reducing the amount of air draft hitting the face of the user.

An air permeable diffuser mat 150 extends across each diffusion aperture 133 to diffuse the air flowing through the diffusion apertures and to reduce noise levels. The diffuser mat material may be attached to the frame by over-moulding, or otherwise permanently or removably attached to the frame 103. The diffuser mat may comprise a fibrous material or a textile. In one embodiment, the diffuser mat 150 comprises hydrophobic and hydrophilic felt fibres that are interwoven through needle-punching.

Figures 58, 59:
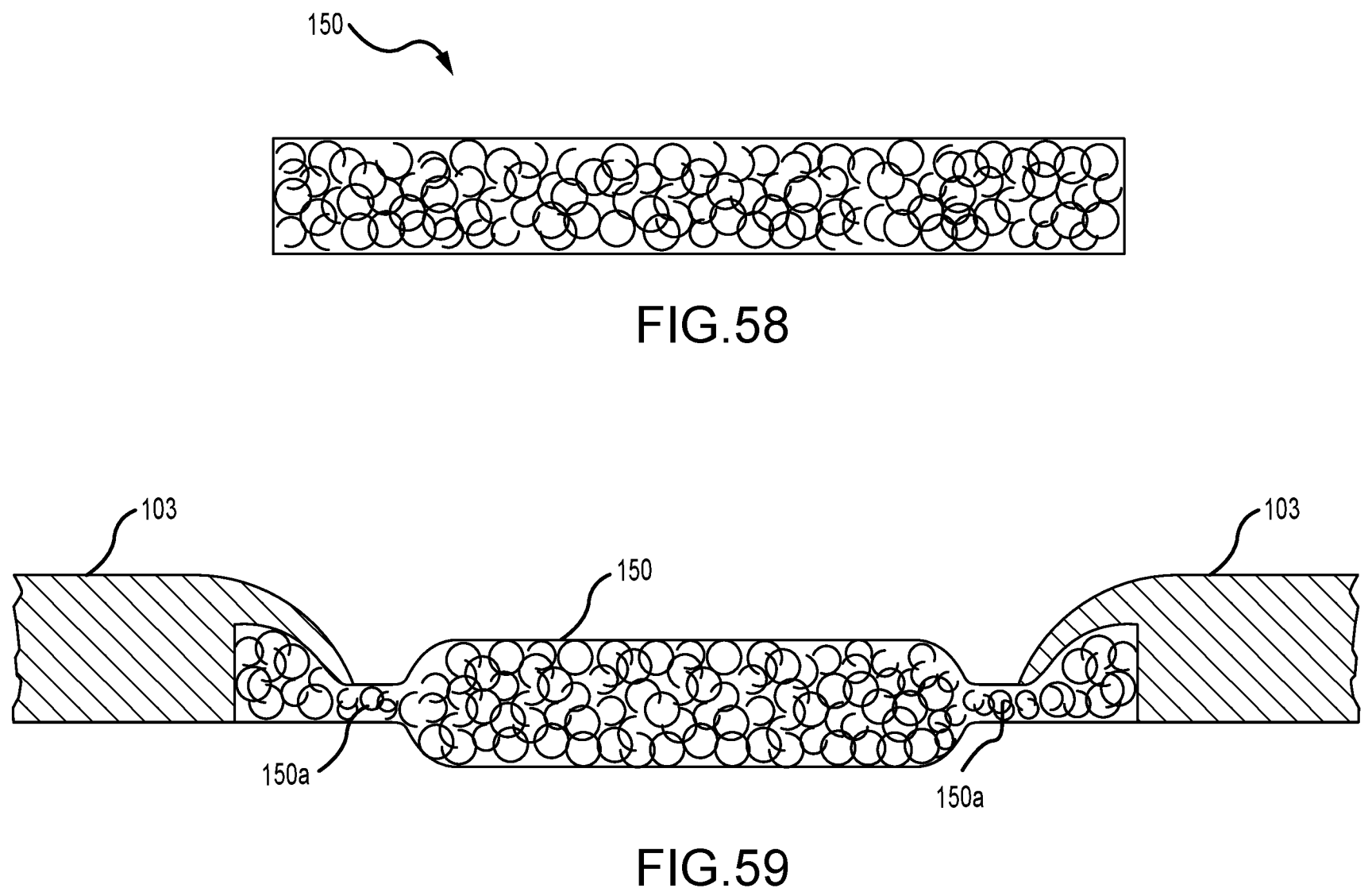
Figure 60:
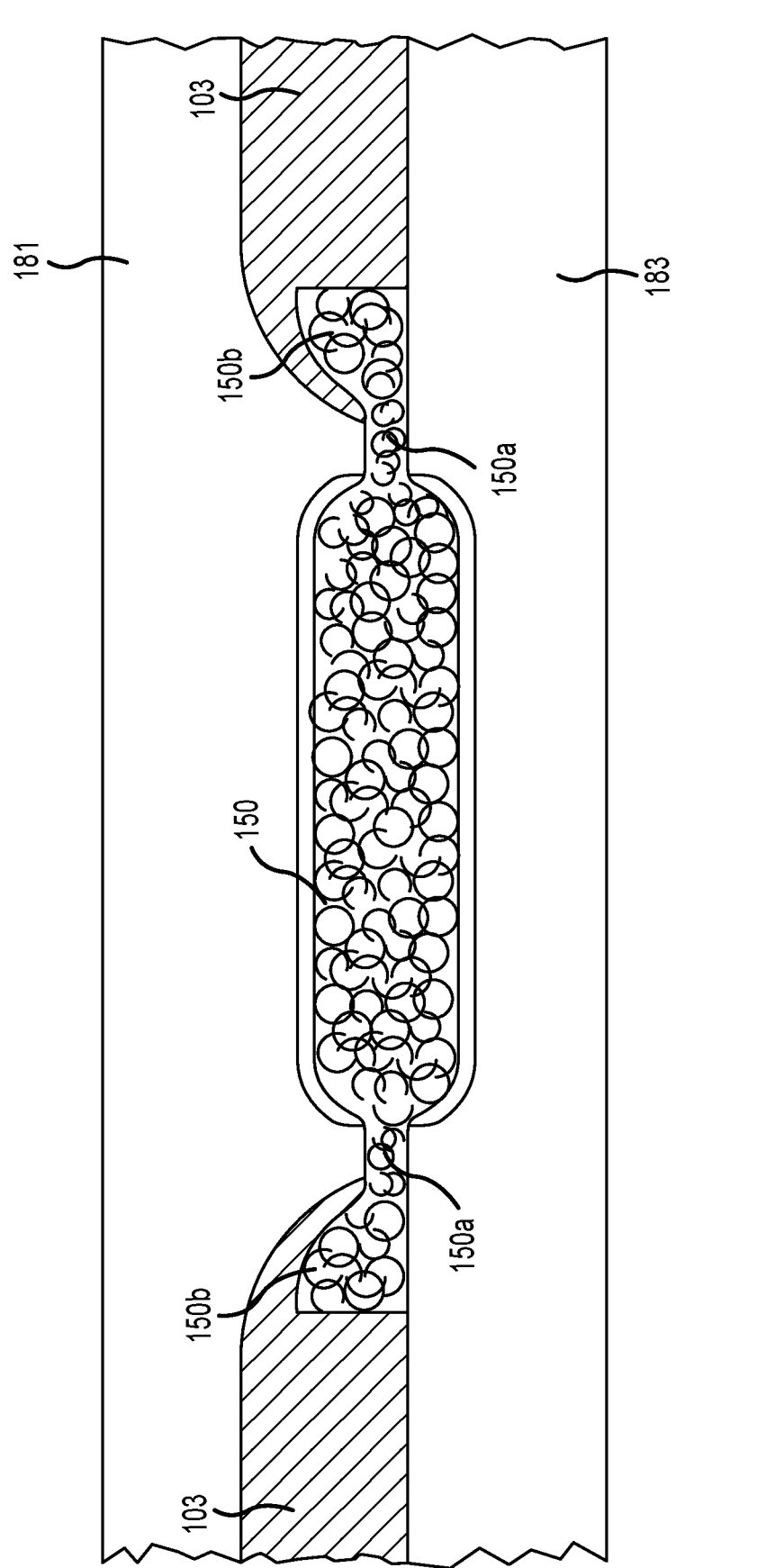
FIG. 60 is a partial side section view of a mould tool showing the method of forming the diffuser mat and overmoulded frame of FIG. 59.

Preferably the mat is attached or bonded to the frame 103. Optionally the entire frame 103 may be formed together with the diffuser mat(s) using an over-moulding process and a two-part mould. FIGS. 58 to 60 illustrate a method of forming a diffuser mat 150 comprising felt fibre. A felt mat 150 having a generally constant thickness is provided, as shown in FIG. 58. The dimensions of the mat 150 are slightly larger than the diffuser aperture dimensions to allow the edges of the mat 150 to be bonded to the nasal seal frame 103. The mat 150 is placed in a two-part mould 181, 183, which is shaped to compress the diffuser mat 150 around a portion that will be positioned in the aperture at the aperture perimeter, to form a compressed border 150*a*, as illustrated in FIG. 60. The frame 103 is then moulded, for example injection moulded, using the same mould. The portions of the mould that compress the diffuser mat prevent frame material flowing into the diffuser aperture. The uncompressed edge of the diffuser mat 150*b*, beyond the compressed portion 150*a*, becomes overmoulded with the frame 103 as shown in FIG. 60. The edge fibres of the diffuser mat 150 are suspended in the rigid plastic of the frame 103 thereby securing the diffuser mat 150 in the frame 103. In alternative embodiments, the diffusion apertures 133 may have other shapes, for example, they may comprise slots, circular, or other shaped openings. There may be fewer or more diffusion apertures, for example, multiple apertures may be provided on each side of the inlet 115. Each diffusion aperture may have a separate diffuser mat, or a single mat may extend across several diffusion apertures. For apertures that are small, such as the bias flow apertures 33 in the first embodiment, may not require a diffuser mat.

Figures 39, 40:
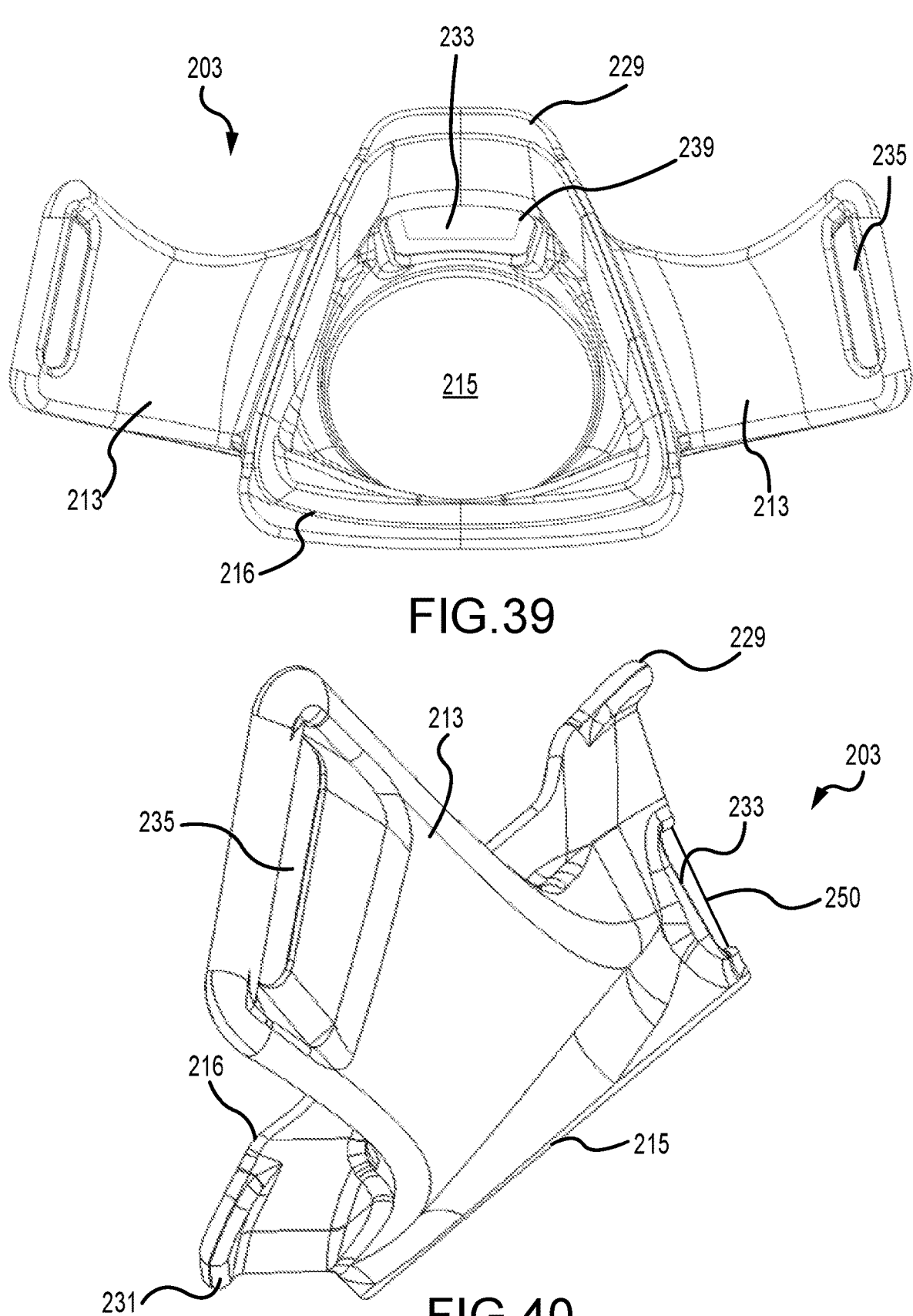
FIG. 39 is a front view of a third embodiment nasal seal support frame having an upper front diffusion aperture.
FIG. 40 is a side view of the support frame of FIG. 39.

Rather than providing multiple diffusion apertures in a lower part of the frame, the diffusion aperture and diffuser mat may be provided in a top portion of the frame. FIGS. 39 and 40 show an embodiment frame 203 having a diffusion aperture 233 positioned directly above the mask frame inlet 215. The frame 103 is substantially as described in relation to the previous embodiment frame 103 unless otherwise described. Like numbers are used to indicate like parts, but with the addition of 100.

The diffusion aperture 233 is generally rectangular and provided centrally on the frame 203, directly above the inlet 215 with the long dimension of the rectangle orientated horizontally. The diffusion aperture 233 may be otherwise shaped, for example it may be oval, circular, trapezoidal, or any other suitable shape.

FIG. 40 illustrates the orientation of the mask frame 203 when it is worn by a user. As illustrated, the diffusion aperture 233 directs air flowing through the aperture generally forward and upward, away from the user's face so as to not cause irritation or discomfort to the user. When the nasal seal 5 (for example, as shown in FIG. 7) is assembled on the frame 203, the pull tab 25 of the seal 3 partially extends over the diffusion aperture 233. This pull tab 25 further assists to direct air flow from the diffusion aperture 233 in a forward direction.

A diffuser mat illustrated schematically by line 250, as described above, extends across the diffusion aperture 233 to diffuse air flowing through the diffusion aperture 233 and to reduce noise. The diffuser mat 250 may be attached to the frame as described above in relation to the embodiment of FIGS. 37-38B. The inner surface of the diffuser mat may be substantially flush with the inner surface of the frame 203.

Figures 41A, 41B, 42:
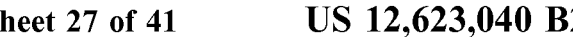
FIG. 41A is a front perspective view of a fourth embodiment nasal seal support frame having an upper diffusion aperture and diffusion channels.
FIG. 41B is a detail front perspective view of a portion of the frame of FIG. 41A with a nasal seal attached to the frame.
FIG. 42 is a front perspective view of the support frame of FIGS. 41A and 41B.

FIGS. 41A to 42 illustrate a further embodiment frame 303 having a diffusion aperture 333 positioned near the top frame flange 329. The frame 303 is substantially as described in relation to the previous embodiment frame 203 unless otherwise described. Like numbers are used to indicate like parts, but with the addition of 100.

The diffusion aperture 333 opens to the front of the frame 333 and is positioned adjacent the frame outlet and is in fluid communication with the chamber formed by the attached seal 305, between the frame 303 and the user.

The surface of the frame 303 adjacent to the diffusion aperture 333 extends generally forwards and slopes downwards from the base of the aperture 333. A plurality of diverging linear grooves 229 are provided on this adjacent frame surface to assist with dispersing exhaled air. As illustrated in FIG. 42, the rear end of each groove 338 is contiguous with the diffusion aperture 333, thus the grooves 338 form channels in fluid communication with the diffusion aperture and with the chamber formed by the nasal seal 305. As illustrated by the arrows in FIG. 42, the grooves 338 spread the air flow from the diffusion aperture across an area wider than the diffusion aperture 333 and guide the air flow away from the face of the user.

The top edge of the nasal seal inlet engages the top flange 329 of the frame 303 and the top edge of the nasal seal inlet and the pull tab 325 at least partly covers the diffusion aperture 333 (see FIG. 41B). The pull tab 325 extends forward, over at least a majority of the grooves 338. Therefore, at least a majority of the exhaled air flow flows along the channels defined by the grooves 338. The lower surface of the pull tab 325 may contact the surface of the frame 303 such that substantially all of the air flow out of the diffusion aperture is along the channels formed by the grooves (and further defined by the lower surface of the pull tab 325).

The lower surface of the pull tab 325 also prevents upwards and rearwards flow of air towards the face of a user.

Figures 43A, 43B, 44:
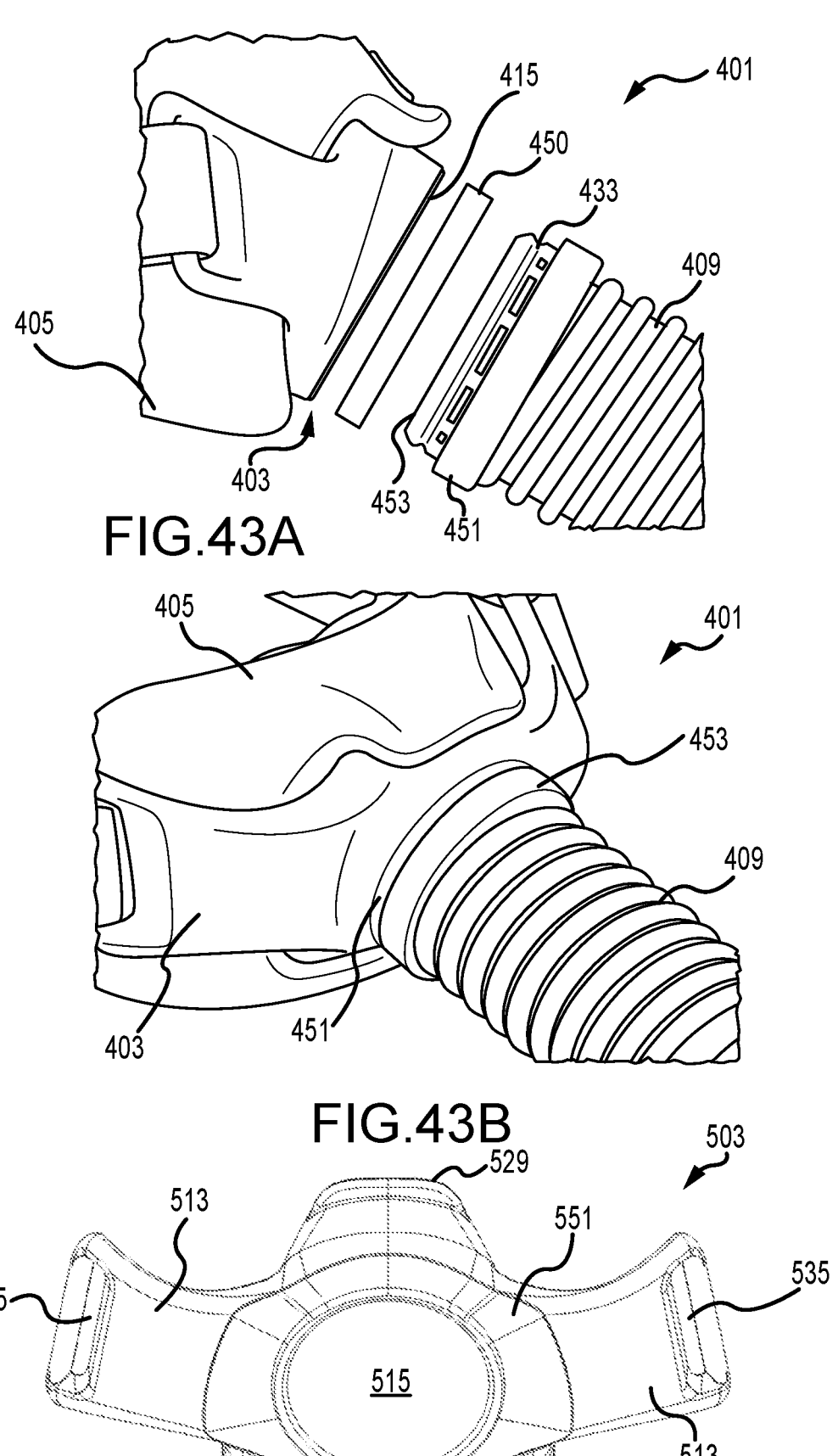
FIG. 43A is an exploded side view of a fifth embodiment respiratory interface assembly having a nasal seal, frame, diffuser mat, connector, and conduit.
FIG. 43B is a front perspective assembly of FIG. 43A.
FIG. 44 is a front perspective view of the support frame of FIGS. 43A and 43B.
Figures 45A, 45B:
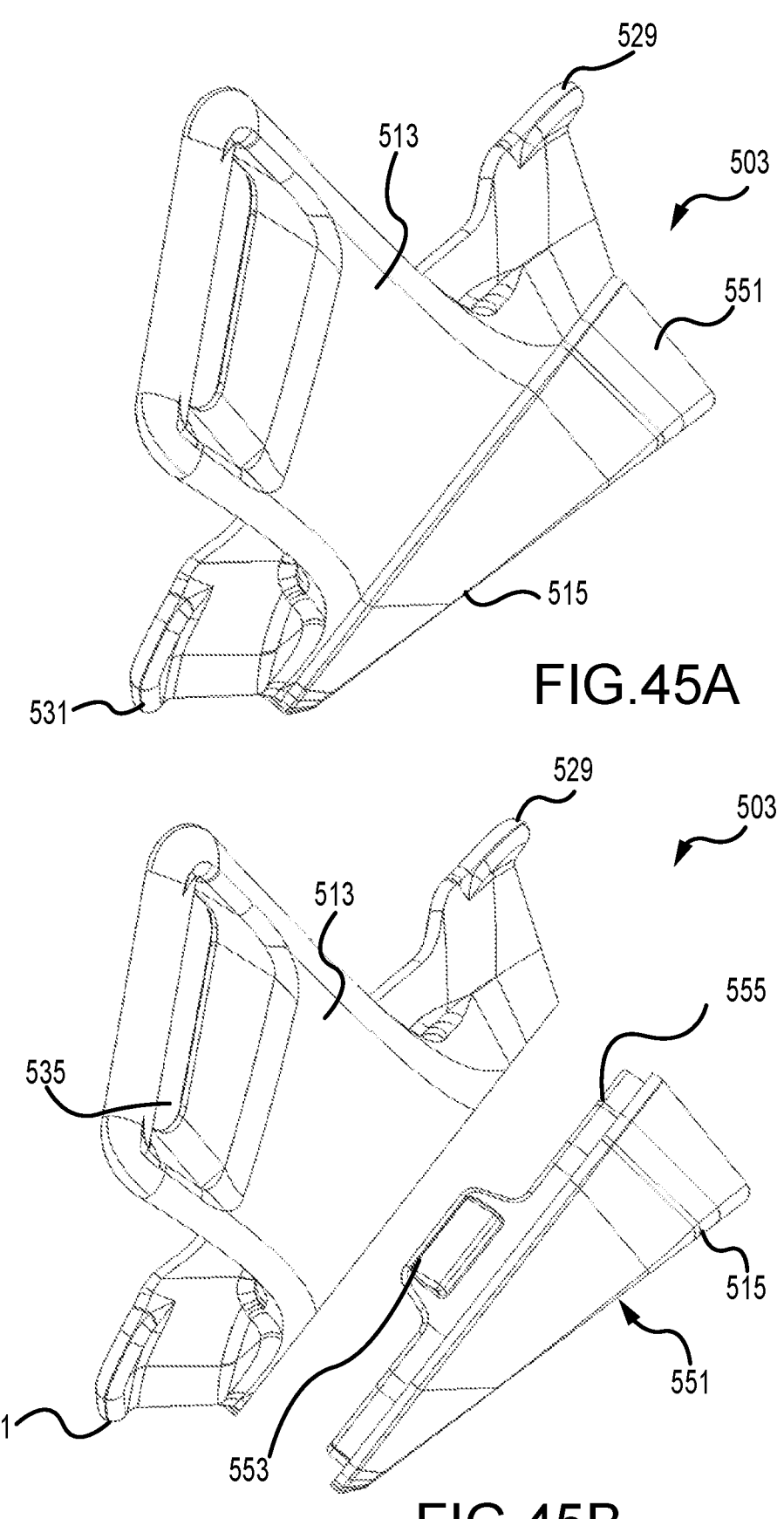
FIG. 45A is a side view of a sixth embodiment nasal seal support frame.
FIG. 45B is an exploded side view of the frame of FIG. 45A.
Figure 46A:
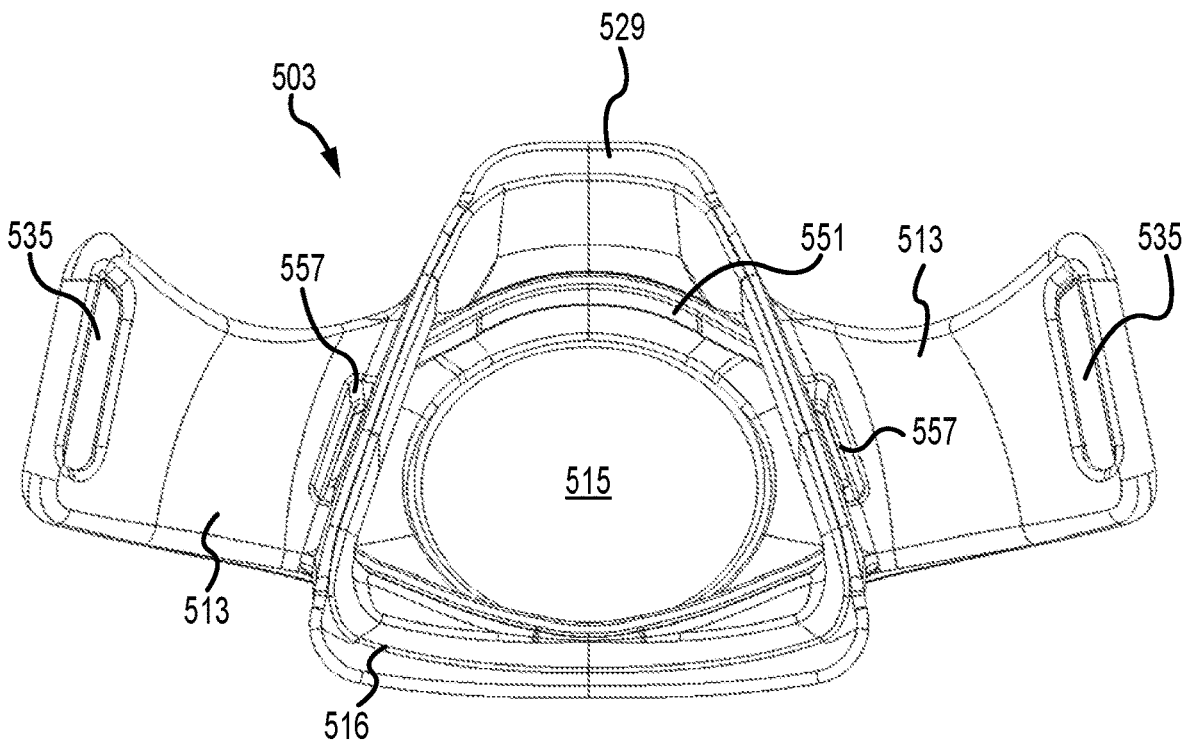
FIG. 46A is a rear view of the support frame of FIG. 45A.
Figure 46B:
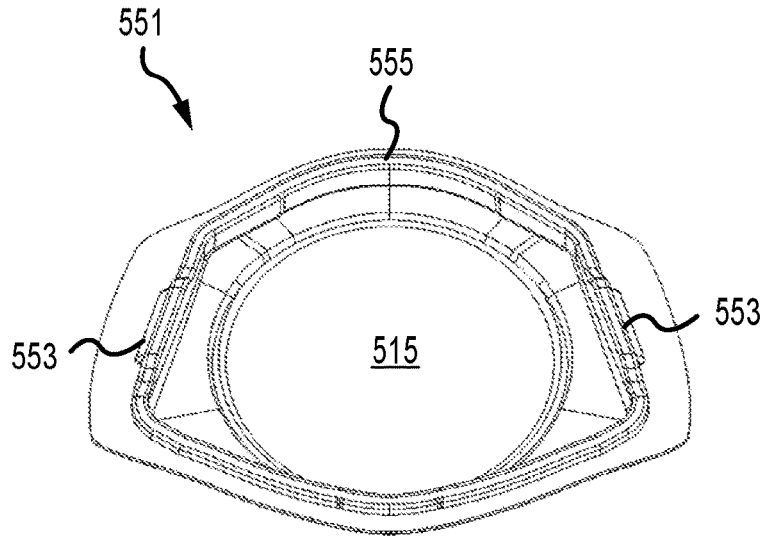
FIG. 46B is a rear view of the diffuser clip from the support frame of FIGS. 45A to 46A.
Figure 47:
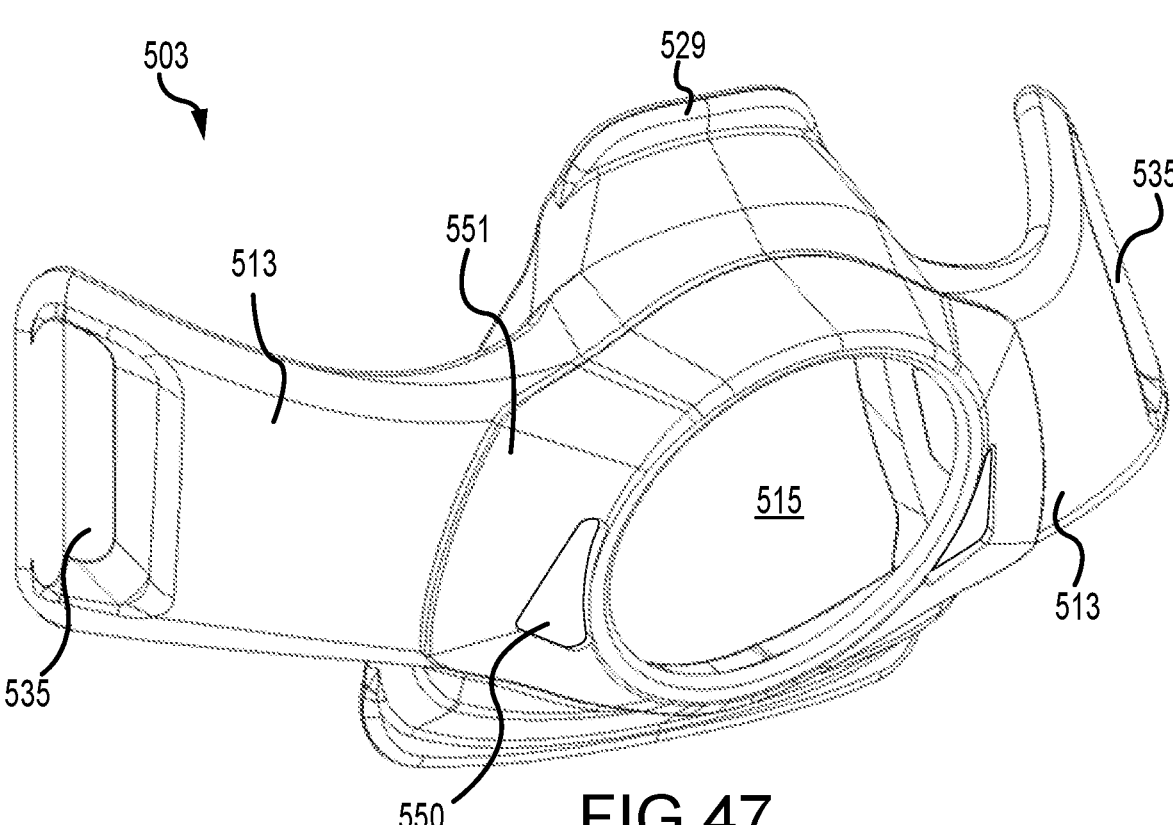
FIG. 47 is a front perspective view of a seventh embodiment nasal seal support frame.
Figure 48:
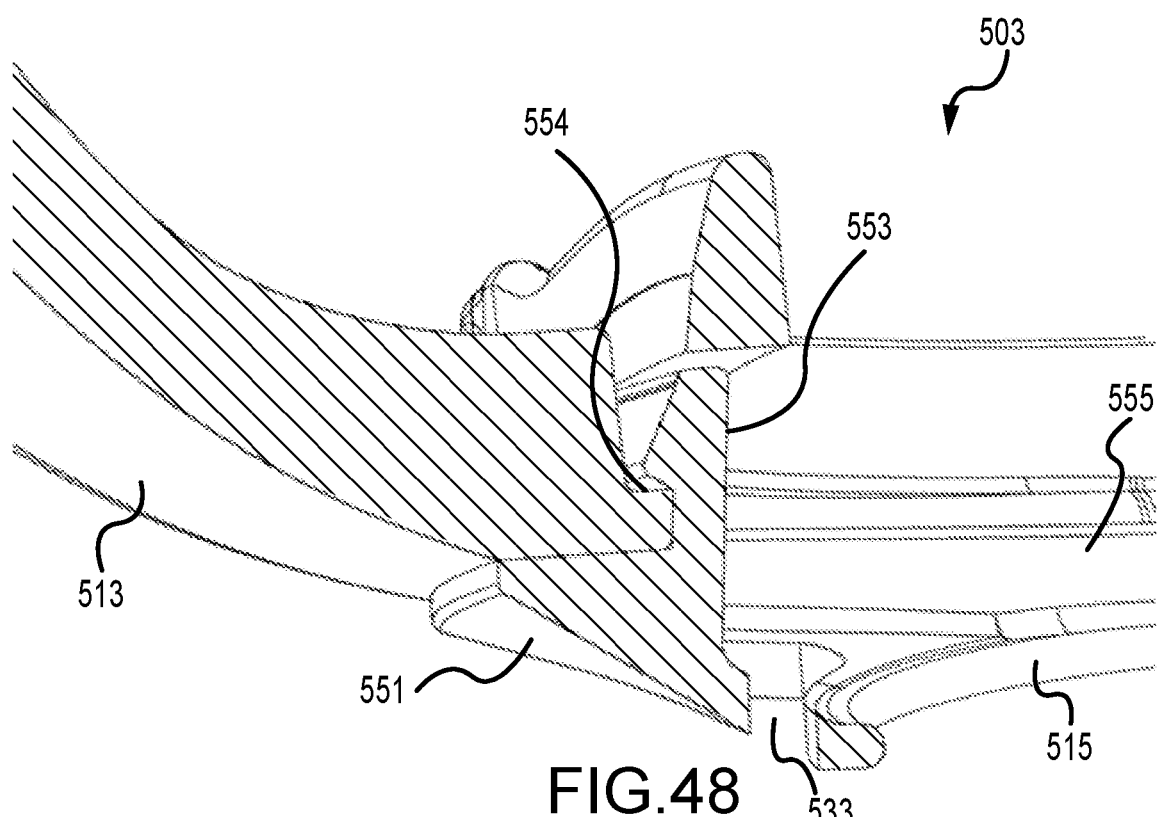
FIG. 48 is a cut-away detail section view showing the connection between the diffuser clip and the support frame body.
Figures 49, 50A, 50B:
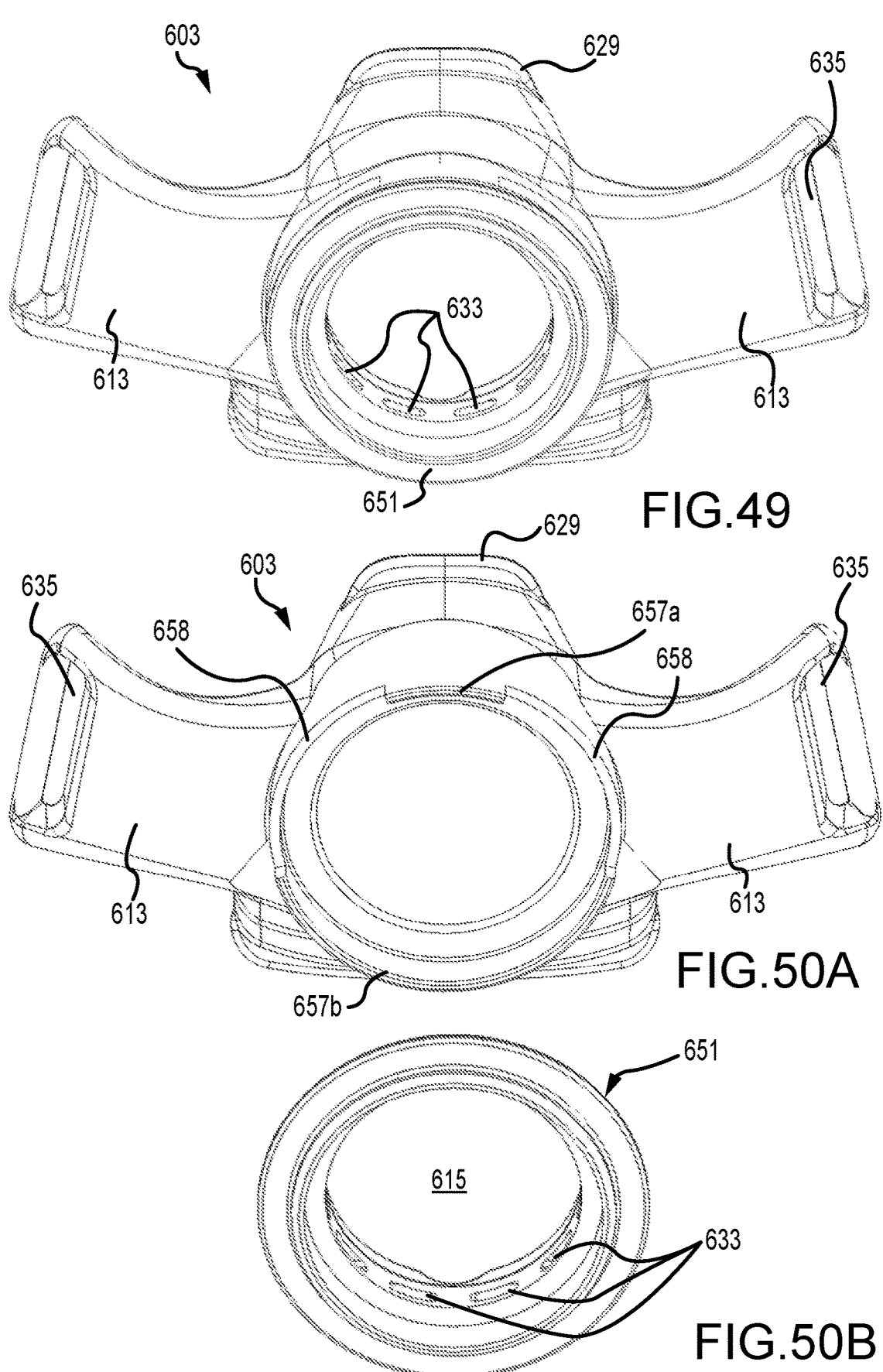
FIG. 49 is a front perspective view of an eighth embodiment nasal seal support frame with an attached conduit connector.
FIG. 50A is a front perspective view of the nasal seal support frame of FIG. 49.
FIG. 50B is a front perspective view of the conduit connector of FIG. 49.
Figures 51, 52:
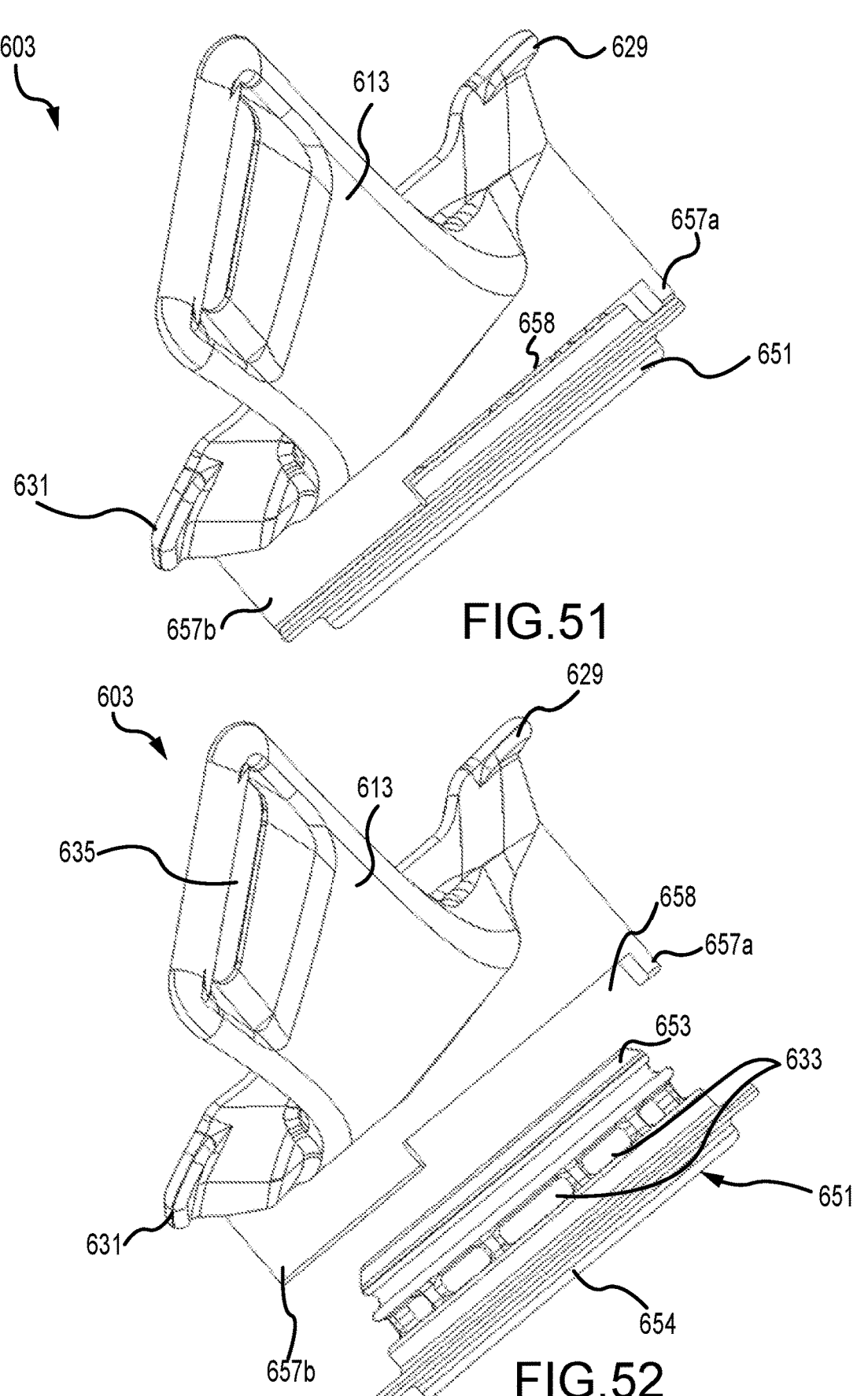
FIG. 51 is a side view of the nasal support frame and attached conduit connector of FIG. 49.
FIG. 52 is an exploded side view of the nasal support frame and attached conduit connector of FIGS. 49 to 51.
Figure 53:
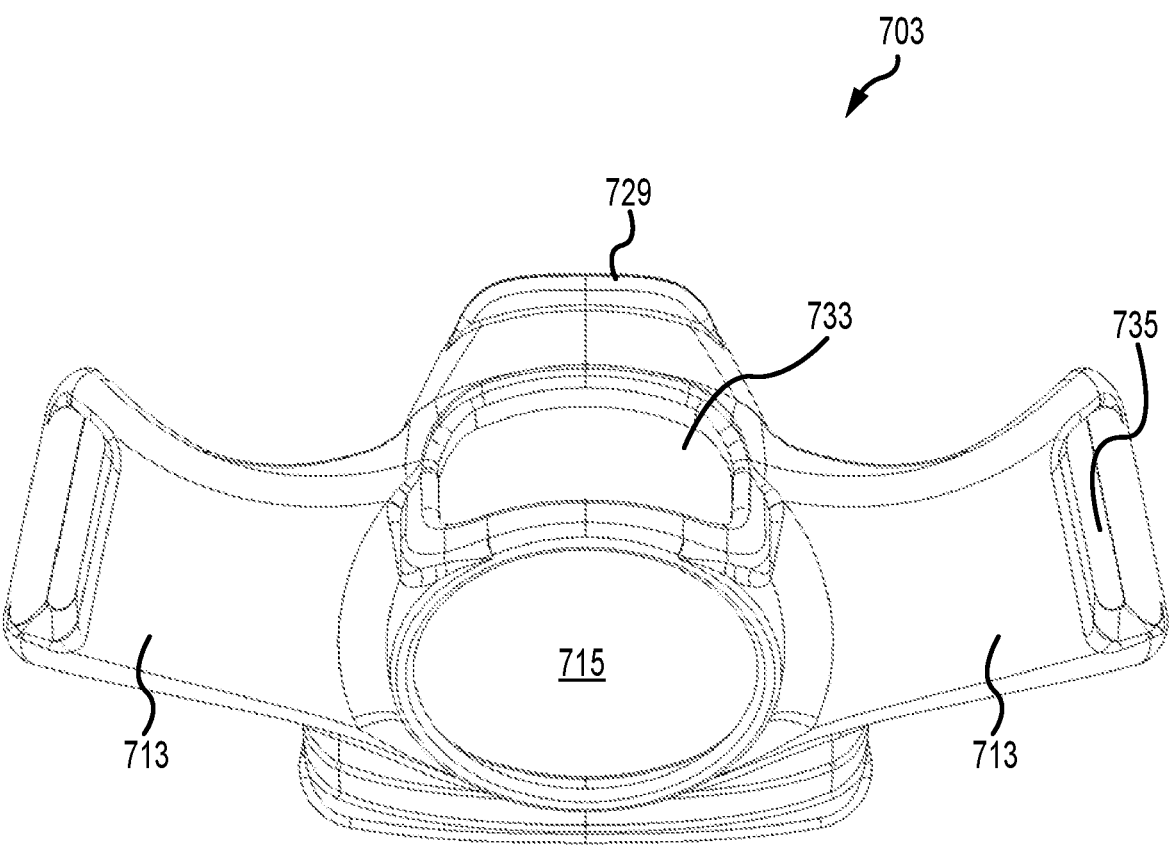
FIG. 53 is a front view of an eighth embodiment nasal seal support frame.

FIGS. 43A and 43B illustrate a further respiratory interface 401 in which the diffuser is provided at the connection between the frame 403 and the fluid conduit 409. The frame 403 is otherwise substantially as described in relation to the first embodiment frame 3 unless described below. Like numbers are used to indicate like parts, but with the addition of 400.

In this embodiment, the conduit 409 is overmoulded to a connector 451 or otherwise permanently or removably attached to the connector. The connector 451 has an engagement feature 453 for removably connecting to the inlet 415 of the frame 403, for example by way of a snap-fit engagement. In the embodiment shown, the engagement feature comprises a snap-fit flange that engages a complementary annular recess provided on the frame inlet 415. The connector 451 is substantially rigid compared to the conduit 409, for example, it may comprise nylon, another plastic, or a composite material.

The conduit 409 is overmoulded to the front portion of the connector 451 or otherwise permanently or removably attached to the connector. The connector 451 is substantially rigid compared to the conduit, for example, it may comprise Nylon, another plastic, or a suitable composite material.

A plurality of diffusion apertures 433 are provided on the connector 451, adjacent to the engagement feature 453. In the embodiment shown, the diffusion apertures 433 comprise a row of elongate slots arranged annularly around the connector. However, alternatively shaped or arranged diffusion apertures are possible. When the connector 451 is engaged with the frame inlet 415, the diffusion apertures sit in front of the frame 405 and are not covered by the frame inlet 415. This allows exhaled air to escape out through the diffusion apertures 433.

A ring-shaped air permeable diffuser mat 450 is positioned over the connector 451 at the diffusion apertures 433, such that the mat 450 covers the diffusion apertures to diffuse air flow out the apertures. As shown in FIG. 43B, when assembled, the diffuser mat 450 is sandwiched between the mask frame inlet 415 and overmoulded conduit connection, to diffuse airflow from the diffusion apertures.

FIGS. 44 to 48 illustrate a further embodiment frame 503 for a respiratory interface. In this embodiment, the frame 503 is a two-part member comprising a main body and a removable diffuser clip 551. The ability to separate the diffuser clip and the main body of the frame allows for easy replacement of the diffuser material by replacing the diffuser clip 551. The frame 503 is otherwise substantially as described in relation to the first embodiment frame 3 unless described below. Like numbers are used to indicate like parts, but with the addition of 500.

The diffuser clip 551 forms a front portion of the mask frame 503, including defining the frame inlet 515. Rearward extending attachment clips 553 are provided on the left and right sides of the diffuser clip 551 to removably engage the diffuser clip 551 to the front side of the main body of the frame 503. The two attachment clips 553 each comprise a protruding angled lip to engage a complementary recess or lip 554 on the frame body and are spaced in from the outer edge of the diffuser clip 551. In the embodiment shown, slots 557 are provided in the arms of the frame 513 (see FIG. 46A) for receiving the attachment clips 553, each slot defining a complementary recess or lip 554 for engagement of the respective attachment clip 553. The slots are positioned on the left and right sides of the perimeter of the breathing chamber defined by the frame, such that the slots 553 are not in direct fluid communication with the chamber.

When the diffuser clip is engaged with the main body of the frame, the rear surface of the diffuser clip 551 adjacent the clip perimeter sits substantially flush with the front surface of the main body to form a tight seal between the two parts, minimizing any air leaks.

The diffuser clip 551 comprises diffusion apertures 533 located on the left and right sides of the mask frame inlet 515. In the embodiment shown, the apertures 533 are substantially triangular, however, in other embodiments the diffusion apertures may be otherwise shaped, for example they may be round, rectangular, irregularly shaped, or may comprise a plurality of slots.

The diffusion apertures 533 are in fluid communication with the fluid chamber defined by the support frame 503, to allow air exhaled by a user into the chamber flow out through the diffusion apertures. An air permeable diffuser mat 550 extends across each diffusion aperture 553 to diffuse the air flowing through the diffusion apertures 553 and to reduce noise levels. The diffuser mat material may be attached to the diffuser clip 551 by over-moulding, or otherwise permanently or removably attached to the diffuser clip 551.

FIGS. 49 to 52 illustrate a further embodiment frame 603 and conduit connector 651 for a respiratory interface. The frame 603 is otherwise substantially as described in relation to the first embodiment frame 3 unless described below. Like numbers are used to indicate like parts, but with the addition of 600.

In this embodiment, the diffusion features are provided on a connector 651, which attaches the conduit (not shown) to the frame 603. The connector 651 has an engagement feature 653 at a rear of the connector, for removably or permanently coupling to the inlet 615 of the frame 603, for example by way of a snap-fit engagement. In the embodiment shown, the engagement feature comprises an annular snap-fit flange that engages a complementary annular recess provided internally on the frame, adjacent the frame inlet 615. When engaged, the connector 651 is rotatable about a central axis.

The conduit (not shown) is overmoulded to the front portion 654 of the connector 651 or otherwise permanently or removably attached to the connector. The connector 651 is substantially rigid compared to the conduit, for example, it may comprise Nylon, another plastic, or a suitable composite material.

A plurality of diffusion apertures 633 are provided on connector 651, adjacent to the engagement feature 653. In the embodiment shown, the diffusion apertures 633 comprise a row of elongate slots arranged annularly around the connector. However, alternatively shaped or arranged diffusion apertures are possible. A ring-shaped air permeable diffuser mat (not shown) is positioned over the connector 653 at the diffusion apertures 633, such that the mat covers the diffusion apertures to diffuse air flow out the apertures.

The frame 605 comprises one or more air barrier tabs 657a, 657b extending forward from the frame, adjacent the inlet 615. When the connector 653 is engaged with the frame inlet 615, the diffusion apertures 633 sit in forward of the inlet 615, but rear of the front edge of the air barrier tabs 657a, 657b and are not covered by the frame inlet 615. The diffuser mat is sandwiched between the mask frame inlet 615 and tube overmoulded connection, to diffuse airflow from the diffusion apertures.

The air barrier tabs 657a, 657b are arc shaped tabs with a curvature concentric with the frame inlet 615. The tabs are spaced apart, defining radial cut-out gaps 657 between adjacent tabs. When the connector 653 is engaged with the frame inlet 615, some of the diffusion apertures 633 are positioned behind an air barrier tab 657a, 657b, while other apertures 633 are positioned in the gaps 657. The air barrier tabs 657a, 657b extend over the respective diffusion apertures to prevent air flow out of those apertures. The diffusion apertures 633 positioned in the gaps 657 between tabs remain exposed such that air can flow freely out the apertures and frame 603.

The air barrier tabs 657a, 657b prevent exhaled air being directed in directions likely to cause annoyance or discomfort to a user, for example towards the user's face. The embodiment shown comprises an upper air barrier tab 657a that blocks upwards air flow that may otherwise be directed towards the user's face, and a lower air barrier tab 657b that blocks downwards air flow that may otherwise be directed towards the user's neck, torso, and possibly their hands during adjustment of the interface. The lower air barrier tab 657b is longer than the upper air barrier tab 657a (for example, 2 to 4 times as long), and extends partly up the left and right sides of the inlet 615.

FIGS. 53 to 57 illustrate a further embodiment frame 703 for a respiratory interface. The frame 703 is otherwise substantially as described in relation to the first embodiment frame 3 unless described below. Like numbers are used to indicate like parts, but with the addition of 700.

The frame comprises a diffusion aperture 733 positioned directly above the mask frame inlet 715.

The diffusion aperture 733 is generally rectangular and provided centrally on the frame 703, directly above the inlet 715 with the long dimension of the rectangle orientated horizontally. The diffusion aperture 733 may be otherwise shaped, for example it may be oval, circular, trapezoidal, or any other suitable shape. Compared to previously described embodiments, the upper region of the mask frame where the diffusion aperture 733 is located is enlarged to allow for a larger diffusion aperture 733 to achieve higher flow rates compared to those with a smaller frame and a smaller diffusion aperture. In the embodiment shown, the diffusion aperture 733 has a length of about 15 mm and a width of about 8.5 mm.

Figure 57:
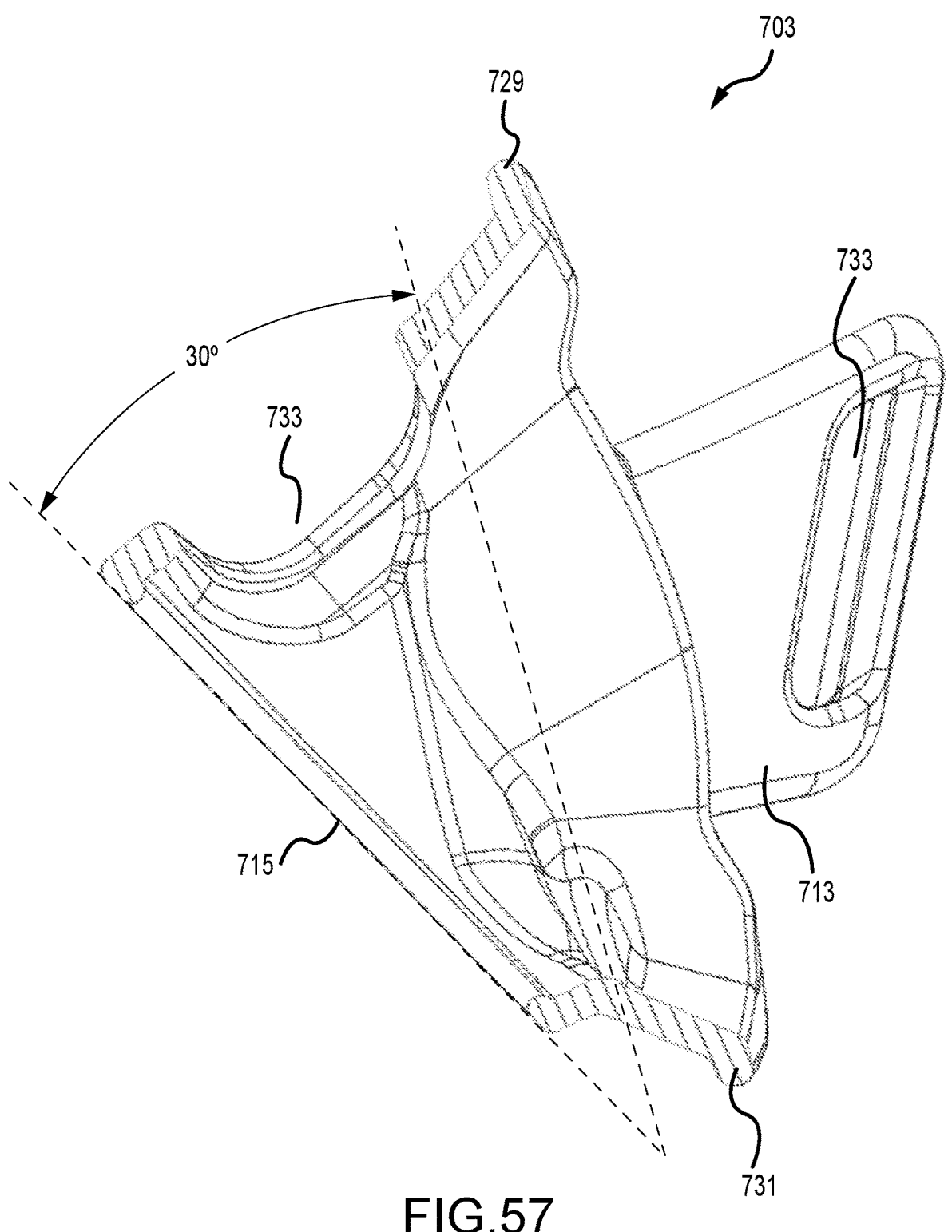
FIG. 57 is a side section view of the nasal seal support frame of FIG. 53.

Referring to FIG. 57, the larger upper region of the mask frame is provided by an increased angle between the frame inlet 715 and the frame's outlet flanges 729, 731. In the embodiment shown, this angle is about 30 degrees. In previously described embodiments, the angle was around 15 degrees. The larger angle brings the upper region of the mask frame about the inlet 715 forward, increasing the depth of the frame and thereby the area available in the region of the mask frame above the inlet 715 and forward of the upper flange 729.

Figure 61:
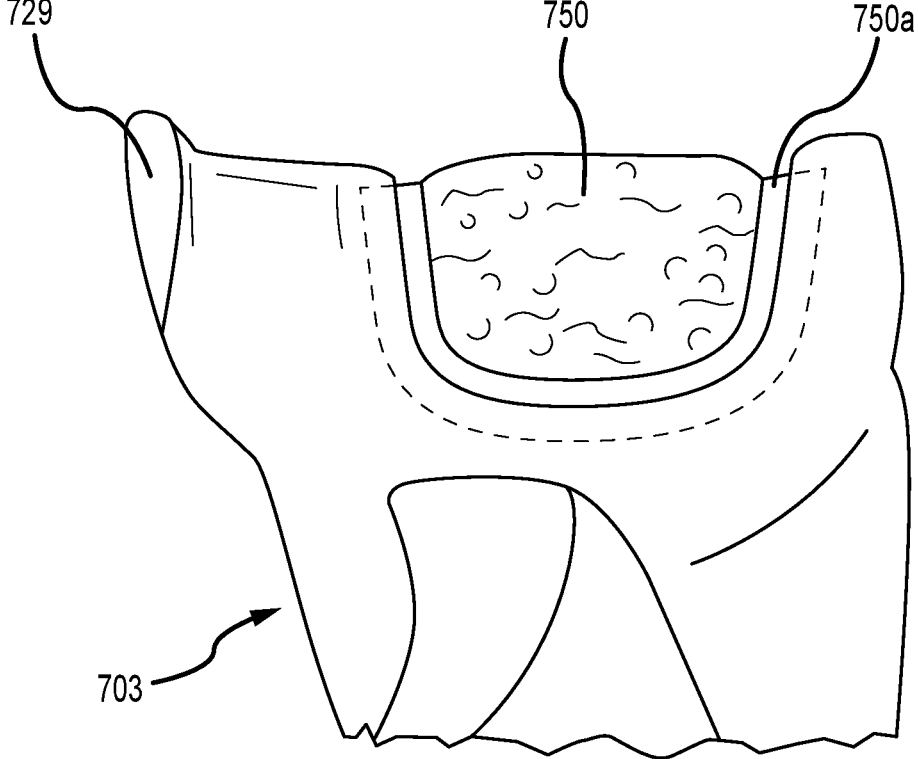
FIG. 61 is a perspective view showing a diffuser mat overmoulded to the nasal support frame of FIGS. 53 to 57.

A diffuser mat 750 (FIG. 61) extends across the diffusion aperture 733 to diffuse air flowing through the diffusion aperture 233 and to reduce noise. The diffuser mat material may be attached to the frame by over-moulding, or otherwise permanently or removably attached to the frame 703.

Optionally the entire frame may be formed together with the diffuser mats using an over-moulding process and a two-part mould.

Figure 54:
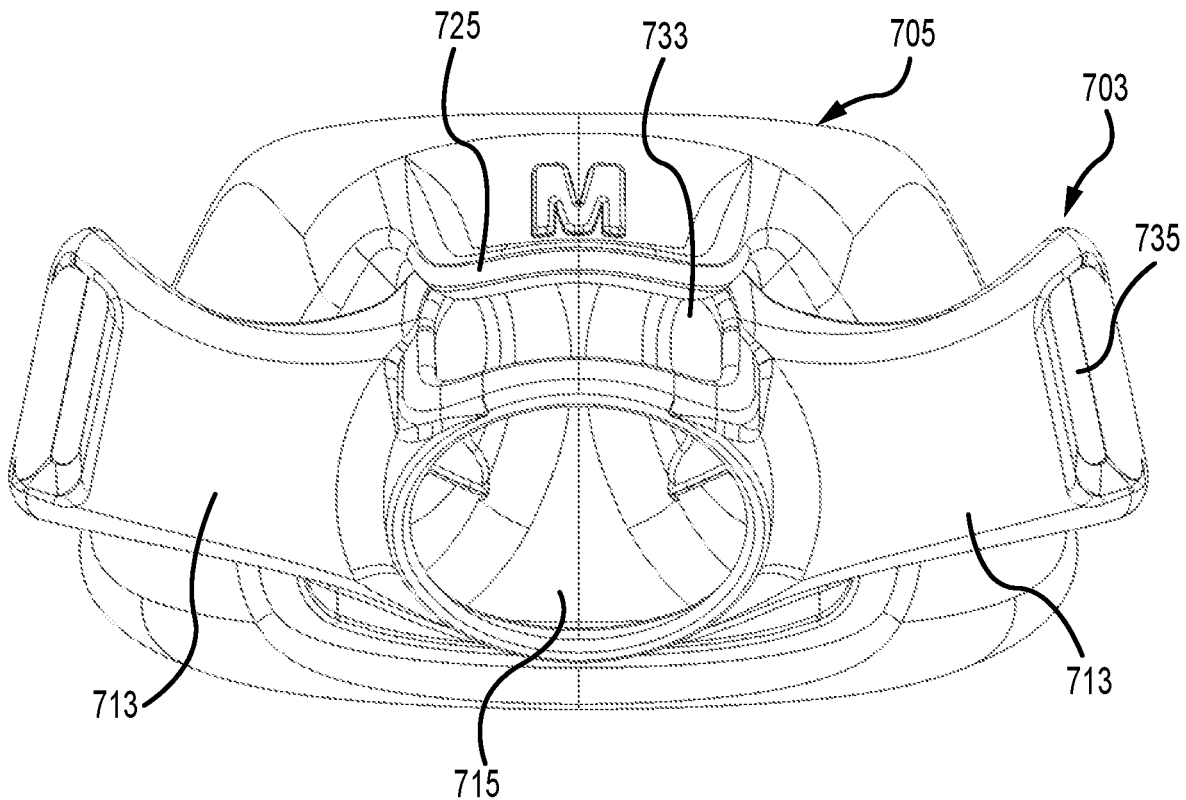
FIG. 54 is a front view of the nasal seal support frame of FIG. 53 and a nasal seal attached.
Figure 55:
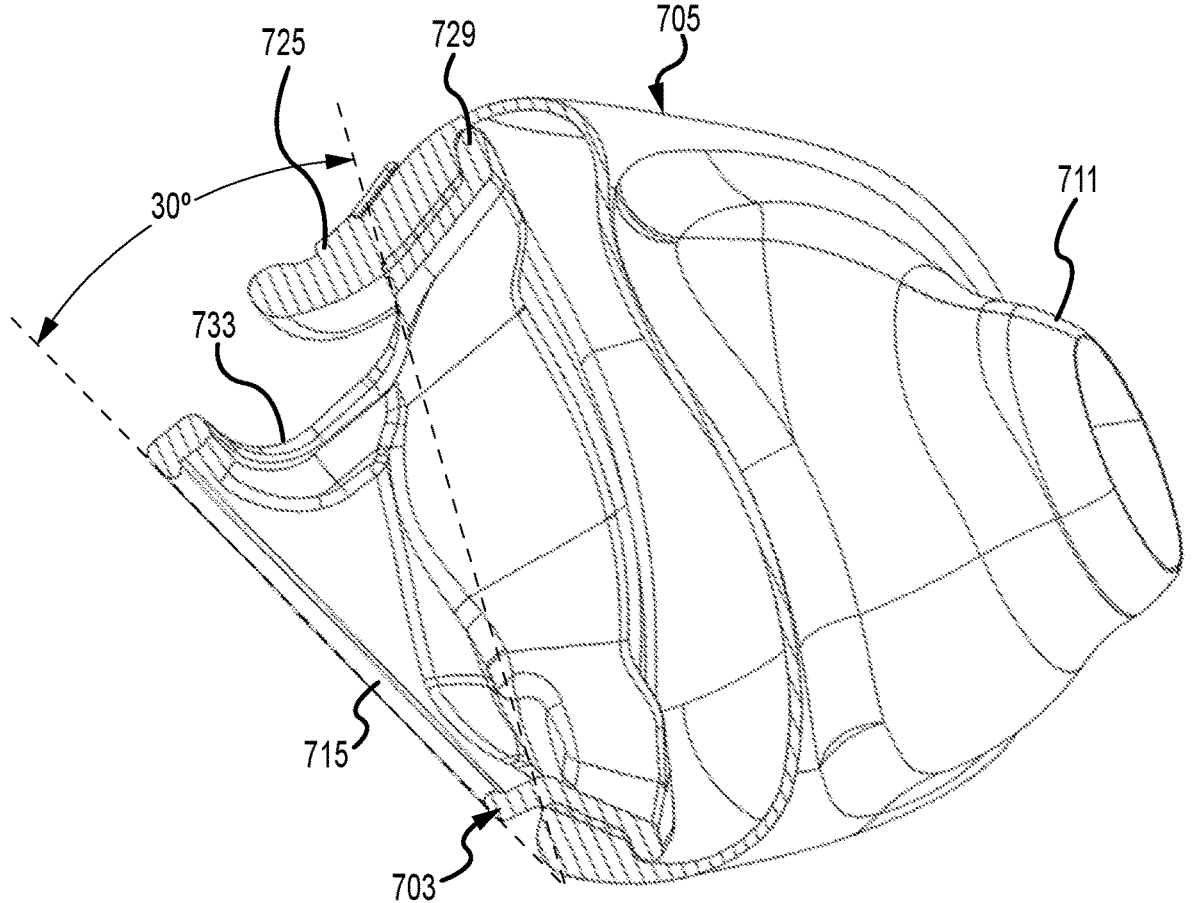
FIG. 55 is a side section view of the nasal seal support frame and seal of FIG. 54, taken through a centreline of the frame.
Figure 56:
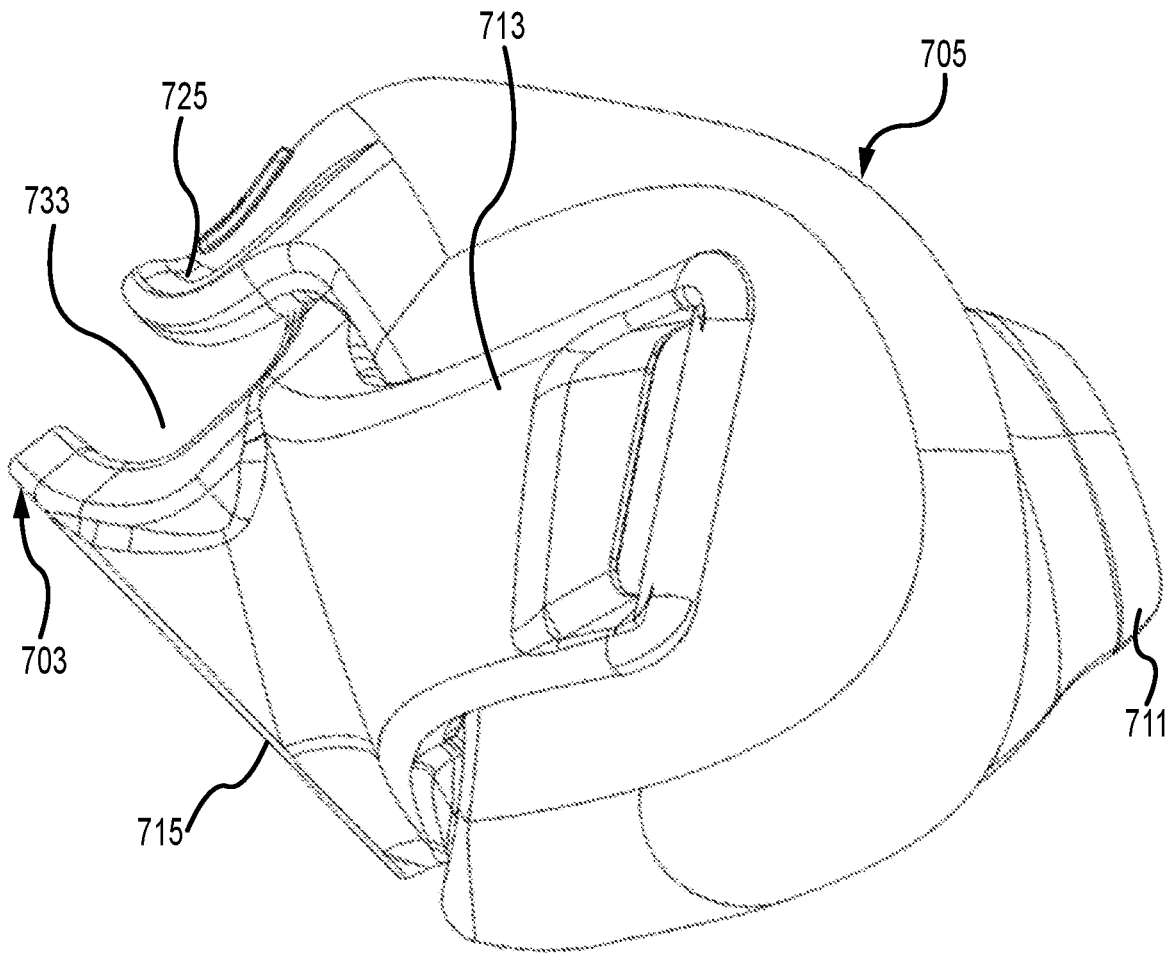
FIG. 56 is a side view of the nasal seal support frame and seal of FIGS. 54 and 55.

FIGS. 54 to 56 illustrate the frame 703 assembled with a nasal seal 705. The pull tab 725 on the nasal seal covers a rear portion of the diffusion aperture 733 and diffuser mat. However, the front edge of the diffusion aperture 733 is located further forward of the front edge of the nasal seal pull tab 725 such that the pull tab does not completely cover the diffusion aperture so as not to fully obstruct gas flow. Preferred embodiments of the invention have been described by way of example only and modifications may be made thereto without departing from the scope of the invention. For example, the dimensions mentioned above are provided as examples only and may vary in masks or seals of different sizes or constructed from different materials to account for different material properties. In the present embodiment, the nasal seal comprises silicone, and the mask frame is composed of rigid Nylon. However, it will be apparent to those skilled in the art that other elastomers or rigid materials such as other plastics or composite materials may be substituted without departing from the scope of the invention.

The invention claimed is:

1. A nasal seal for a respiratory therapy mask for contacting the face of a user, the nasal seal comprising:
    a main body defining a cavity and a fluid inlet;
    two nasal prongs projecting from the main body for the delivery of fluid to the user's nares; and
    a transition fillet around a base of each prong, the transition fillet defining a transition between the main body and the base of each prong, the transition fillet extending in a radially outward direction from the base of each prong between a first edge of the transition fillet at the nasal prong and a second edge of the transition fillet at the main body, the second edge positioned radially outward from the first edge, an outer surface of the transition fillet defining a concave surface in the radial outward direction extending from the first edge and the second edge;
    wherein the transition fillet has a chord length from the first edge to the second edge, wherein the chord length of each transition fillet is constant around the base of each prong.

2. A nasal seal as claimed in claim 1, wherein the nasal seal comprises a resilient material.

3. A nasal seal as claimed in claim 1, wherein a terminal region of each nasal prong has a wall thickness that tapers towards a tip of the nasal prong.

4. A nasal seal as claimed in claim 3, wherein the wall thickness at the nasal prongs' tips is less than 20% of the wall thickness of the nasal prong wall in a major part of the nasal prong.

5. A nasal seal as claimed in claim 3, wherein in the terminal region, the nasal prong wall thickness gradually decreases over a length of about 2 mm.

6. A nasal seal as claimed in claim 3, wherein, in the terminal regions, the taper has a varying chord length and a varying radius of curvature.

7. A nasal seal as claimed in claim 3, wherein each nasal prong defines a cavity wherein the cross sectional area of each cavity decreases from a maximum area at the base of the prong to a minimum area at the tip of the prong.

8. A nasal seal as claimed in claim 3, wherein each nasal prong comprises a nare sealing region between the terminal region and the base of the respective prong, the nare sealing region having a concave transition region adjacent the terminal region, the transition region having a height that is constant around a perimeter of the prong.

9. A nasal seal as claimed in claim 3, wherein each nasal prong comprises a nare sealing region between the terminal region and the base of the respective prong, at least a major part of the nare sealing region having a wall thickness at least twice the wall thickness of a user contacting rear part of the seal main body.

10. A nasal seal as claimed in claim 9, wherein a user-contacting portion of the seal main body has a wall thickness in the range of about 0.4 mm to about 0.6 mm.

11. A nasal seal as claimed in claim 9, wherein side walls of the seal main body have a wall thickness in the range of about 1.8 mm to about 2.2 mm.

12. A nasal seal as claimed in claim 1, wherein each nasal prong defines a non-cylindrical cavity.

13. A nasal seal as claimed in claim 12, wherein the cavity in each nasal prong has a cross-section with a major dimension and a minor dimension, both the major and minor dimensions decreasing from the base of the respective prong to the tip.

14. A nasal seal as claimed in claim 1, wherein the fluid inlet is a substantially D-shaped opening, being widest at a bottom of the opening and narrowest at the top of the opening.

15. A nasal seal as claimed in claim 1, comprising an inwardly extending lip at the fluid inlet for engaging a support frame.

16. A nasal seal as claimed in claim 15, wherein the lip is arcuate in side profile, and concave relative to a front of the seal.

17. A nasal seal as claimed in claim 16, wherein the lip side profile has a radius of about 25 mm.

18. A nasal seal as claimed in claim 1, wherein a radius of each transition fillet varies around the base of each prong.

19. The nasal seal as claimed in claim 1, wherein the transition fillet extends radially outward from the first edge.

20. The nasal seal as claimed in claim 1, wherein the main body comprises side walls and a concave user contacting surface, wherein the two nasal prongs project from the concave user contacting surface, wherein the transition fillet is defined between the concave user contacting surface and the base of each prong, wherein the concave user contacting surface extends towards the cavity.

21. The nasal seal as claimed in claim 20, wherein the side walls comprise a wall thickness that is greater than a wall thickness of the concave user contacting surface.

* * * * *